United States Patent
Beatch

(10) Patent No.: US 11,135,214 B2
(45) Date of Patent: *Oct. 5, 2021

(54) METHODS FOR ENHANCING THE BIO AVAILABILITY AND EXPOSURE OF A VOLTAGE-GATED POTASSIUM CHANNEL OPENER

(71) Applicant: Xenon Pharmaceuticals Inc., Burnaby (CA)

(72) Inventor: Gregory N. Beatch, West Vancouver (CA)

(73) Assignee: Xenon Pharmaceuticals Inc., Burnaby (CA)

( * ) Notice: Subject to any disclaimer, the term of this patent is extended or adjusted under 35 U.S.C. 154(b) by 1 day.

This patent is subject to a terminal disclaimer.

(21) Appl. No.: 16/410,851

(22) Filed: May 13, 2019

(65) Prior Publication Data

US 2019/0343823 A1 Nov. 14, 2019

Related U.S. Application Data

(60) Provisional application No. 62/670,253, filed on May 11, 2018.

(51) Int. Cl.
| | | |
|---|---|---|
| *A01N 37/00* | (2006.01) | |
| *A61K 31/215* | (2006.01) | |
| *A01N 37/12* | (2006.01) | |
| *A01N 37/44* | (2006.01) | |
| *A61K 31/24* | (2006.01) | |
| *A01N 25/00* | (2006.01) | |
| *A61K 31/472* | (2006.01) | |
| *A61P 25/08* | (2006.01) | |
| *A61K 9/00* | (2006.01) | |

(52) U.S. Cl.
CPC .......... *A61K 31/472* (2013.01); *A61K 9/0053* (2013.01); *A61P 25/08* (2018.01)

(58) Field of Classification Search
None
See application file for complete search history.

(56) References Cited

U.S. PATENT DOCUMENTS

| | | | |
|---|---|---|---|
| 8,119,602 | B2 | 2/2012 | Zhang et al. |
| 8,236,861 | B2 | 8/2012 | Anttila |
| 8,293,911 | B2 | 10/2012 | Vernier et al. |
| 8,993,593 | B2 | 3/2015 | Vernier et al. |
| 2009/0318507 | A2 | 12/2009 | Rundfeldt et al. |
| 2013/0131030 | A1 | 5/2013 | Belanoff et al. |

FOREIGN PATENT DOCUMENTS

| | | | |
|---|---|---|---|
| EP | 1713458 | B1 | 3/2008 |
| EP | 1891089 | B1 | 11/2014 |
| WO | 2008024398 | A2 | 2/2008 |
| WO | 2011094186 | A1 | 8/2011 |
| WO | 2019217924 | A1 | 11/2019 |

OTHER PUBLICATIONS

Marzo et al. (Pharmacokinetics and pharmacodynamics of safinamide, a neuroprotectant with antiparkinsonian and anticonvulsant activity. Pharmacological Research, (2004) 50 (1) , pp. 77-85).*
Johannessen et al. (Management of Focal-Onset Seizures. Drugs, 2006, vol. 66, No. 13, p. 1701).*
Aycardi et al., "A First-in-Human Study to Assess the Safety, Tolerability, Pharmacokinetics and Preliminary Pharmacodynamics of a Novel Small Molecule KV7.2/7.3 Positive Allosteric Modulator (XEN1101) in Healthy Subjects," Presented at the 72nd Annual Meeting of the American Epilepsy Society, New Orleans, LA (Dec. 3, 2018).
Beatch, et al., "A Phase 1 Study Utilizing Transcranial Magnetic Stimulation to Assess the Pharmacodynamic Effects of a Novel Potassium Channel Opener (XEN1101) on Human Cortical Excitability," Presented at the 72nd Annual Meeting of the American Epilepsy Society, New Orleans, LA (Dec. 3, 2018).
Bialer, et al., "Progress report on new antiepileptic drugs: A summary of the Thirteenth Eilat Conference on New Antiepileptic Drugs and Devices (EILAT XIII)", EPILEPSIA, vol. 58, No. 2, Jan. 23, 2017 (Jan. 23, 2017), p. 181-221.
Bialer, et al., "Progress report on new antiepileptic drugs: A summary of the Fourteenth Eilat Conference on New Antiepileptic Drugs and Devices (EILAT XIV). I. Drugs in preclinical and early clinical development," EPILEPSIA,vol. 59, No. 10, Oct. 1, 2018 (Oct. 1, 2018), p. 1811-1841.
Brown, D.A. et al., "Muscarinic suppression of a novel voltage-sensitive K+ current in a vertebrate neurone" Nature (1980), 283:673-676.
Carlisle et al., "Estimation of total hepatic blood flow by duplex ultrasound" Gut 1992, 33:92-97.
Darmani, et al., "Effects of antiepileptic drugs on cortical excitability in humans: A TMS-EMG and TMS-EEG study," Hum Brain Mapp. 2018;1-14.
Elger, C.E. et al., "Modern management of epilepsy: A practical approach" Epilepsy Behav. (2008), 12:501-539.
Friedman, et al., "KCNQ channel openers reverse depressive symptoms via an active resilience mechanism," Nature Comm. (2016), 7:1-7.

(Continued)

*Primary Examiner* — Layla Soroush
(74) *Attorney, Agent, or Firm* — Dechert LLP

(57) ABSTRACT

In certain embodiments, the present disclosure is directed to methods and uses for treating seizure disorders in a human, wherein the methods and uses comprise orally administering a therapeutically effective amount of the voltage-gated potassium channel allosteric modulator, N-[4-(6-fluoro-3,4-dihydro-1H-isoquinolin-2-yl)-2,6-dimethylphenyl]-3,3-dimethylbutanamide (Compound A), to the human in need thereof, for example, under fed conditions. The present disclosure is further directed to various improved methods of therapy and administration of Compound A.

26 Claims, 9 Drawing Sheets

(56) References Cited

OTHER PUBLICATIONS

Goldberg, The Epilepsy Foundation Pipeline Conference: "XEN1101, a Novel Modulator of Kv7.2/3 for the Treatment of Epilepsy" presentation held on Feb. 23, 2018.

Goldberg, "XEN1101: A Novel, Next-Generation KCNQ2 Modulator for the Treatment of Epilepsy," EILAT XIV Meeting held on May 15, 2018.

Goldberg, "XEN1101, a Novel Modulator of Kv7.2/3 for the Treatment of Epilepsy", Feb. 22, 2018, p. 1-10.

Harris, J.A. et al., "Retigabine (ezogabine) as add-on therapy for partial onset seizures: an update for clinicians", Therapeutic Advances in Chronic Disease (2011), 2(6), pp. 371-376).

Heimbach, T. et al., "Case Studies for Practical Food Effect Assessments across BCS/BDDCS Class Compounds using In Silico, In Vitro, and Preclinical In Vivo Data", The AAPS Journal (2012), vol. 15, No. 1, pp. 143-158.

Hiriz, D. et al., "How common are the "common" neurologic disorders?" Neurology (2007), 68:326-337.

Hitiris, N. et al., "Mortality in epilepsy" Epilepsy and Behavior (2007), 10:363-376.

International Search Report and Written Opinion for International Application No. PCT/US2019/031872 dated Aug. 6, 2019.

Kupferberg, H., "Antiepileptic drug development program: a cooperative effort of government and industry" Epilepsia (1989), 30 (Suppl. 1):S51-S56.

Lang, et al., "Effects of lacosamide and carbamazepine on human motor cortex excitability: A double-blind, placebo-controlled transcranial magnetic stimulation study," Seizure 22 (2013) 726-730.

Marvanova, "Pharmacokinetic characteristics of antiepileptic drugs (AEDs)", Mental Health Clinician, vol. 6, No. 1, Jan. 1, 2016 (Jan. 1, 2016), p. 8-20.

Ossemann et al., "Effect of a single dose of retigabine in cortical excitability parameters:A cross-over, double-blind placebo-controlled TMS study," Epilepsy Research (2016), 126:78-82.

Premoli, et al., "Lamotrigine and Levetiracetam Exert a Similar Modulation of Tms-Evoked Eeg Potentials," Epilepsia, 58(1):42-50, 2017 DOI: 10.1111/EPI.13599.

Premoli, et al., "TMS as a pharmacodynamic indicator of cortical activity of a novel anti-epileptic drug, XEN1101," The Authors. Annals of Clinical and Translational Neurology published by Wiley Periodicals, Inc on behalf of American Neurological Association (2019).

Tan, et al., "Effects of the KCNQ channel opener ezogabine on functional connectivity of the ventral striatum and clinical symptoms in patients with major depressive disorder," Mol Psychiatry. Author manuscript; available in PMC 2019, 1-21.

Ziemann, et al., "TMS and drugs revisited 2014," J. Int. Fed. Clinical Neurophysiology (2015) 126:1847-1868.

Cheng, et al., "Food Effects on Oral Drug Absorption: Application of Physiologically-Based Pharmacokinetic Modeling as a Predictive Tool," Pharmaceutics (2020) 12, 672, pp. 1-18.

International Preliminary Report on Patentability and Written Opinion for International Application No. PCT/US2019/031872 dated Nov. 17, 2020.

Pithavala, et al., "Evaluation of the effect of food on the pharmacokinetics of axitinib in healthy volunteers," Cancer Chemother Pharmacol (2012) 70:103-112.

POTIGA (ezogabine) Tablets, CV, FDA Approved Labeling (2012), NDA 022345/S-001.

Welling, P.G., "Effects of Food on Drug Absorption," Annu. Rev. Nutr. (1996) 16:383-415.

* cited by examiner

METHODS FOR ENHANCING THE BIO AVAILABILITY AND EXPOSURE OF A VOLTAGE-GATED POTASSIUM CHANNEL OPENER

1. BACKGROUND

Epilepsy is a common neurological disorder, with a worldwide estimated prevalence of 0.7% of the population (50 million people) (see Hirtz, D. et al., *Neurology*. (2007), 68:326-337). It is characterized by abnormal electrical activities in the brain leading to seizures. For epidemiological purposes, the definition requires more than one unprovoked seizure of any type.

Patients with epilepsy have an increased mortality risk compared with the general population due primarily to the etiology of the disease. However, in patients with uncontrolled epilepsy, the greatest seizure-related risk of mortality is due to sudden unexpected death in epilepsy (SUDEP) (see, Hitiris, N. et al., *Epilepsy and Behavior* (2007), 10:363-376. Patients who participate in clinical trials of investigational antiepileptic drugs (AEDs) generally have had epilepsy for more than 10 years and have failed multiple AED therapies.

The pathophysiology of most forms of epilepsy remains poorly understood, but it is known that epileptic seizures arise from an excessively synchronous and sustained firing of a group of neurons. Persistent increase in neuronal excitability is common to all epileptic syndromes. The therapeutic strategy in treating epilepsy involves reducing neuronal excitability through various mechanistic pathways. Over the past two decades, several new AEDs were developed and marketed to expand the therapeutic spectrum by targeting different mechanisms of action and to improve the risk/benefit profile. Currently available AEDs are considered to act by inhibition of synaptic vesicle glycoprotein, potentiation of the inhibitory GABAergic neurotransmission, reduction of glutamate-mediated excitatory neurotransmission, or inhibition of voltage-gated sodium or calcium channels. Despite this, up to 30% of patients remain refractory to conventional treatment and continue to have uncontrolled seizures (see Brown, D. A. et al., *Nature* (1980), 283:673-676, and Elger, C. E. et al., *Epilepsy Behav*. (2008), 12:501-539. The quality of life in refractory patients is poor; they cannot drive a car, and they have difficulty working or living independently. Additionally, many patients have behavioral, neurological, and/or intellectual disturbances as sequalae of their seizure disorder. Current agents have minimal to no effects on neuronal potassium-gated channels, in spite of the fact that these channels have a major role in the control of neuronal excitability. Medicines with novel mechanisms of action, or medicines that improve on the already marketed AEDs are therefore needed to address the significant unmet clinical need for seizure control in patients with treatment-resistant epilepsy.

N-[4-(6-Fluoro-3,4-dihydro-1H-isoquinolin-2-yl)-2,6-dimethylphenyl]-3,3-dimethylbutanamide (herein referred to as "Compound A") is a small molecule currently being developed for the treatment of seizure disorders. Compound A and its use as a potassium channel modulator is disclosed in U.S. Pat. Nos. 8,293,911 and 8,993,593, the disclosures of which are hereby incorporated by reference in their entireties.

The voltage-gated potassium channels Kv7.2 and Kv7.3 (Kv7.2/Kv7.3) are important in controlling neuronal excitability. Kv7.2/Kv7.3 underlie the neuronal "M-current", named according to its initial characterization as a neuronal current decreased in response to muscarinic/cholinergic agonists (see Brown, D. A. et al., *Nature* (1980), 283:673-676). The M-current is a non-inactivating, hyperpolarizing current known to act as a brake on neuronal hyperexcitability. Consequently, a decrease in the Kv7.2-mediated M-current, for example through genetic loss-of-function, can cause neuronal depolarization and an increase in membrane and neuronal excitability that can lead to action potential bursts that manifest as epileptic seizures. In contrast, an increase in the Kv7.2-mediated M-current can hyperpolarize the cell membrane and thereby reduce neuronal excitability and prevent the initiation and propagation of action potential bursts and the resultant seizures. Enhancing the open state of Kv7.2/Kv7.3 channels in neurons favors a hyperpolarized resting state, which reduces rapid action potential spiking (i.e., burst firing). Such enhancement can provide a stabilizing effect on excitable, particularly hyper-excitable, neurons and therefore be useful in treating certain seizure disorders. This enhancement has been clinically proven to be effective for treatment of seizure disorders, such as partial onset seizures in adults with epilepsy, with retigabine (ezogabine), a known Kv7.2/Kv7.3 opener.

Retigabine has the following structure:

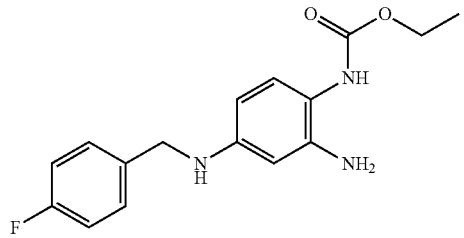 [SMILES: CCOC(=O)Nc1ccc(NCc2ccc(F)cc2)cc1N]

Retigabine was first identified as an analogue of the analgesic compound flupirtine in the late 1980s. Retigabine demonstrated broad spectrum activity in studies designed to identify novel anti-convulsant agents using a battery of rodent seizure models (see Kupferberg, H., *Epilepsia* (1989), 30 (Suppl. 1):S51-S56). It was approved for partial onset seizures in 2011, but was removed from the market in 2017 for commercial reasons following black-box warnings related to discoloration of skin, lips, nails and retinal pigmentary changes which appear to be related to formation of chromophoric retigabine dimers after long term use (Prescott, J. S. and Evans, C. A., "Pigmentary abnormalities (discoloration) associated with ezogabine/retigabine treatment: nonclinical aspects, Poster 2.324 presented at the 68th Annual Meeting of the American Epilepsy Society (AES), Seattle, Wash., U.S.A., Dec. 5-9, 2014).

While significant advances have been made in this field, particularly in the context of Compound A and its use in treating seizure disorders, there remains a substantial need for improved methods to increase the bioavailability and exposure of Compound A when orally administered to humans having seizure disorders, such as epilepsy.

2. SUMMARY

In some embodiments, the present disclosure is directed to a method of treating a disease, disorder, or condition associated with Kv7 potassium channel dysfunction in a human in need thereof, comprising orally administering a therapeutically effective amount of Compound A to the human under fed conditions or from between 30 minutes prior to consuming food until 2 hours after consuming food. In certain instances, the disease, disorder, or condition associated with Kv7 potassium channel dysfunction is a seizure disorder, such as focal onset epilepsy.

In some embodiments, the present disclosure is directed to a compound for use in treating a disease, disorder, or condition associated with Kv7 potassium channel dysfunction in a human in need thereof, wherein the compound is Compound A and a therapeutically effective amount of the compound is orally administered to the human under fed conditions or from between 30 minutes prior to consuming food until 2 hours after consuming food. In certain instances, the disease, disorder, or condition associated with Kv7 potassium channel dysfunction is a seizure disorder, such as focal onset epilepsy.

In one embodiment, the present disclosure provides a method of treating a seizure disorder in a human in need thereof, comprising orally administering an amount of Compound A to the human under fed conditions or from between 30 minutes prior to consuming food until 2 hours after consuming food, wherein the amount of Compound A is sufficient to treat the seizure disorder in the human.

In one embodiment, the present disclosure provides a compound for use in treating a seizure disorder in a human in need thereof, wherein the compound is Compound A and the compound is orally administered to the human under fed conditions or from between 30 minutes prior to consuming food until 2 hours after consuming food.

In one embodiment, the present disclosure provides a method of treating a seizure disorder in a human in need thereof, comprising orally administering an amount of Compound A to the human under fed conditions or from between 30 minutes prior to consuming food until 2 hours after consuming food, wherein the amount of Compound A is from 2 to 200 mg.

In one embodiment, the present disclosure provides a method of increasing one or more of the $C_{max}$, $AUC_{inf}$, $T_{max}$, or $t\frac{1}{2}_{\lambda z}$ of Compound A in a human receiving an oral administration of Compound A, comprising orally administering an amount of Compound A to the human under fed conditions or from between 30 minutes prior to consuming food until 2 hours after consuming food, wherein the method increases one or more of $C_{max}$, $AUC_{inf}$, $T_{max}$, or $t\frac{1}{2}_{\lambda z}$ as compared to when the same amount of Compound A is orally administered to the human under fasted conditions.

In one embodiment, the present disclosure provides a compound for use in increasing one or more of the $C_{max}$, $AUC_{inf}$, $T_{max}$, or $t\frac{1}{2}_{\lambda z}$ of the compound in a human receiving an oral administration of the compound, wherein the compound is Compound A and the compound is orally administered to the human under fed conditions or from between 30 minutes prior to consuming food until 2 hours after consuming food, and wherein the oral administration increases one or more of $C_{max}$, $AUC_{inf}$, $T_{max}$, or $t\frac{1}{2}_{\lambda z}$ as compared to when the same amount of Compound A is orally administered to the human under fasted conditions.

In certain embodiments, the present disclosure provides a method of increasing bioavailability or one or more of the $C_{max}$, $AUC_{inf}$, $T_{max}$, or $t\frac{1}{2}_{\lambda z}$ of Compound A in a human receiving an oral administration of Compound A, comprising (a) informing the human that orally administering Compound A under fed conditions or from between 30 minutes prior to consuming food until 2 hours after consuming food increases the bioavailability or one or more of the $C_{max}$, $AUC_{inf}$, $T_{max}$, or $t\frac{1}{2}_{\lambda z}$ of Compound A; and (b) in reliance on step (a), orally administering Compound A under fed conditions or from between 30 minutes prior to consuming food until 2 hours after consuming food.

In certain such embodiments, the probability that (b) occurs (i.e., the administration occurs under fed conditions or from between 30 minutes prior to consuming food until 2 hours after consuming food) is increased relative to the method in the absence of step (a).

In one embodiment, the present disclosure provides a method of orally administering Compound A to a human in need thereof, comprising orally administering Compound A to the human under fed conditions or from between 30 minutes prior to consuming food until 2 hours after consuming food, wherein the method increases one or more of $C_{max}$, $AUC_{inf}$, $T_{max}$, or $t\frac{1}{2}_{\lambda z}$ of Compound A as compared to when the same amount of Compound A is orally administered to the human under fasted conditions.

In one embodiment, the present disclosure provides a method of reducing a dose of Compound A that is orally administered to a human in need thereof as part of a treatment regimen, comprising orally administering a reduced dose of Compound A to the human under fed conditions or from between 30 minutes prior to consuming food until 2 hours after consuming food, wherein the reduced dose is a lower dose than would be needed to achieve one of more of the same $C_{max}$, $AUC_{inf}$, $T_{max}$, or $t\frac{1}{2}_{\lambda z}$ of Compound A when orally administered to the human under fasted conditions.

In one embodiment, the present disclosure provides a compound for use in reducing a dose of the compound that is orally administered to a human in need thereof as part of a treatment regimen, wherein the compound is Compound A and the compound is orally administered to the human under fed conditions or from between 30 minutes prior to consuming food until 2 hours after consuming food, and wherein the reduced dose is a lower dose than would be needed to achieve one of more of the same $C_{max}$, $AUC_{inf}$, $T_{max}$, or $t\frac{1}{2}_{\lambda z}$ of Compound A when orally administered to the human under fasted conditions.

In one embodiment, the present disclosure provides a method of treating a seizure disorder in a human in need thereof, comprising orally administering a therapeutically effective amount of Compound A to the human. In certain embodiments, the method produces, for Compound A, one or more of:
  a $C_{max}$ of at least 40 ng/mL,
  an $AUC_{inf}$ of at least 2500 h·ng/mL,
  a $T_{max}$ of at least 3.25 h, or
  a $t\frac{1}{2}_{\lambda z}$ of at least 130 h.

In one embodiment, the present disclosure provides a compound for use in treating a seizure disorder in a human in need thereof, wherein the compound is Compound A and the compound is orally administered to the human. In certain embodiments, the oral administration produces, for Compound A, one or more of:
  a $C_{max}$ of at least 40 ng/mL;
  an $AUC_{inf}$ of at least 2500 h·ng/mL,
  a $T_{max}$ of at least 3.25 h, or
  a $t\frac{1}{2}_{\lambda z}$ of at least 130 h.

In one embodiment, the present disclosure provides a method of increasing resting motor threshold (RMT) or active motor threshold (AMT) in a human in need thereof, comprising orally administering an amount of Compound A to the human, optionally under fed conditions or from between 30 minutes prior to consuming food until 2 hours after consuming food, wherein the amount of Compound A is sufficient to increase RMT or AMT in the human or the amount of Compound A is from 2 to 200 mg.

In one embodiment, the present disclosure provides a compound for use in increasing RMT or AMT in a human in need thereof, wherein the compound is Compound A and an amount of the compound is orally administered to the human, optionally under fed conditions or from between 30 minutes prior to consuming food until 2 hours after consuming food, and wherein the amount of Compound A is sufficient to increase RMT or AMT in the human or the amount of Compound A is from 2 to 200 mg.

In one embodiment, the present disclosure provides a method of decreasing corticospinal or cortical excitability in a human in need thereof, comprising orally administering an amount of Compound A to the human, optionally under fed conditions or from between 30 minutes prior to consuming food until 2 hours after consuming food, wherein the amount of Compound A is sufficient to increase corticospinal or cortical excitability in the human or the amount of Compound A is from 2 to 200 mg.

In one embodiment, the present disclosure provides a compound for use in decreasing corticospinal or cortical excitability in a human in need thereof, wherein the compound is Compound A and an amount of the compound is orally administered to the human, optionally under fed conditions or from between 30 minutes prior to consuming food until 2 hours after consuming food, and wherein the amount of Compound A is sufficient to increase corticospinal or cortical excitability in the human or the amount of Compound A is from 2 to 200 mg.

In certain embodiments, the present disclosure generally provides methods for enhancing the bioavailability and exposure of Compound A when orally administered.

Accordingly, one aspect of this disclosure is a method of treating a seizure disorder in a human, wherein the method comprises orally administering a therapeutically effective amount of Compound A to the human in need thereof under fed conditions.

Another aspect of this disclosure is a method of enhancing the bioavailability and exposure of Compound A in a human receiving an oral administration of a therapeutically effective amount of Compound A for the treatment of a seizure disorder, wherein the method comprises orally administering a therapeutically effective amount of Compound A to the human under fed conditions.

Another aspect of this disclosure is a method of enhancing the extent of Compound A's absorption and exposure in a human after oral administration of Compound A to the human, wherein the method comprises orally administering a therapeutically effective amount of Compound A to the human under fed conditions.

These and other aspects of this disclosure will be apparent upon reference to the following detailed description. To this end, various references are set forth herein which describe in more detail certain background information and procedures and are each hereby incorporated by reference in their entirety.

3. BRIEF DESCRIPTION OF THE DRAWINGS

Figure 3:
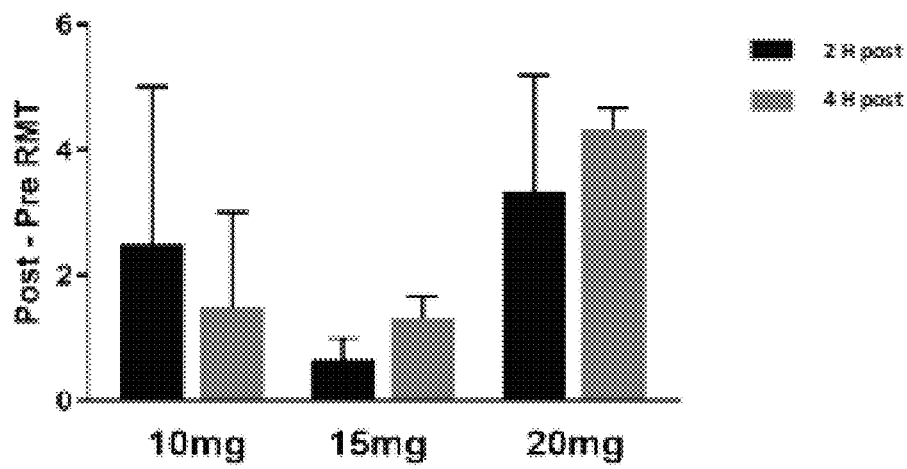
Figure 3:
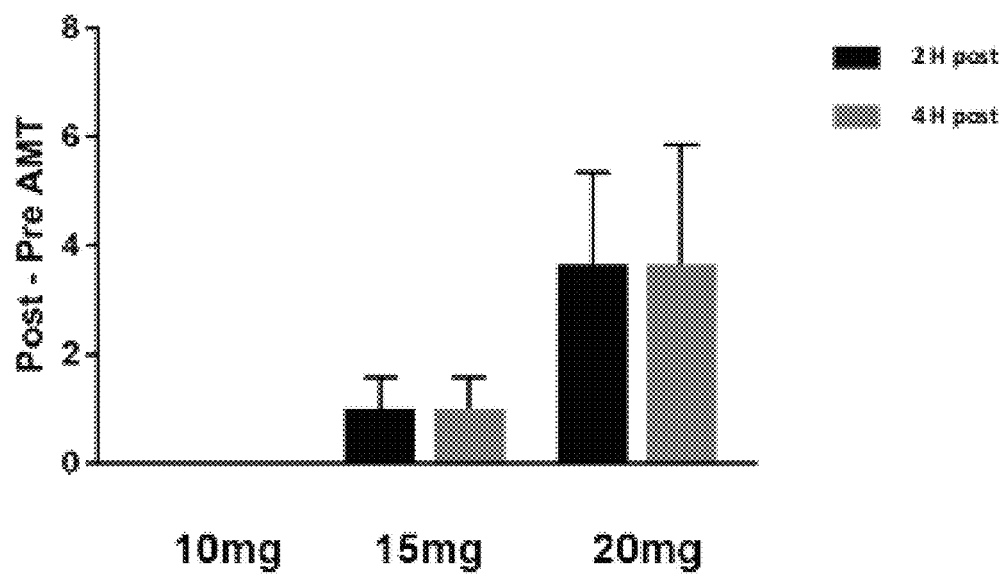

FIG. 3 includes graphical images depicting Compound A induced modulation of resting motor threshold showing post-pre RMT (y-axis) over 3 doses (10 mg, 15 mg, and 20 mg) at 2 and 4 hours post-drug intake (x-axis) (A); and Compound A induced modulation of active motor threshold showing post-pre AMT (y-axis) over 3 doses (10 mg, 15 mg, and 20 mg) at 2 and 4 hours post-drug intake (x-axis) (B).

Figure 4:
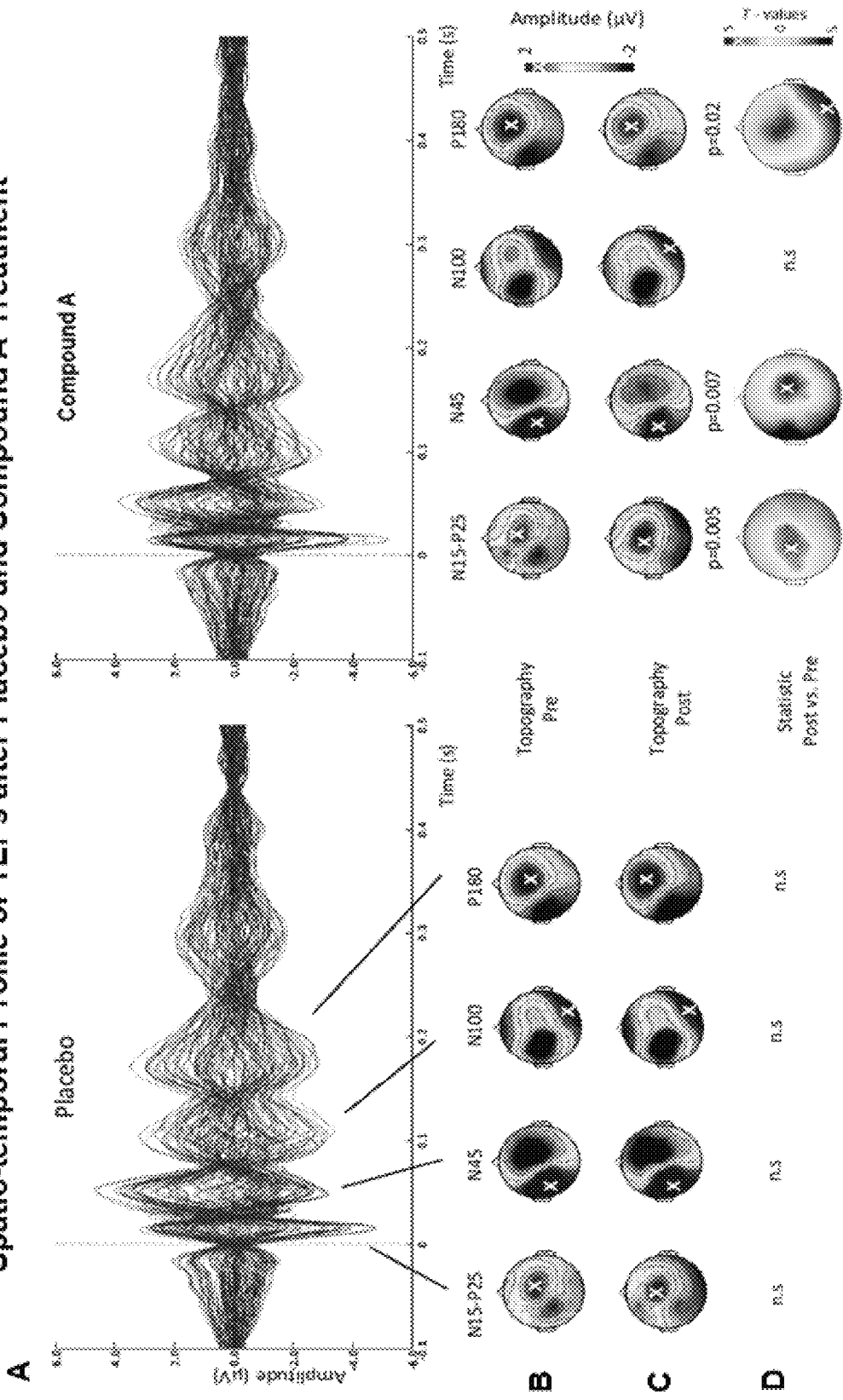

FIG. 4 includes graphical images depicting the spatiotemporal profile of TEPs after placebo and Compound A treatment. Panel A shows grand-average (n=16) butterfly plots before (Pre) and after (Post) intake of placebo (left) and Compound A (right). Each line represents TEPs recorded at a single EEG channel. Topographical scalp distributions of the amplitude (μV) of the main TEP components (N15-P25, N45, N100 and P180) before and after drug intake are shown in panel B and C respectively. Panel D represents t-statistic maps of the TEP amplitude showing post-dose versus pre-dose differences. "n.s" stands for non-significant results and the white "x"s on the topographic scalp distributions indicate regions of positive amplitude and t-statistics, whereas the dark regions without "x"s indicate negative amplitude and t-statistics.

Figure 5:
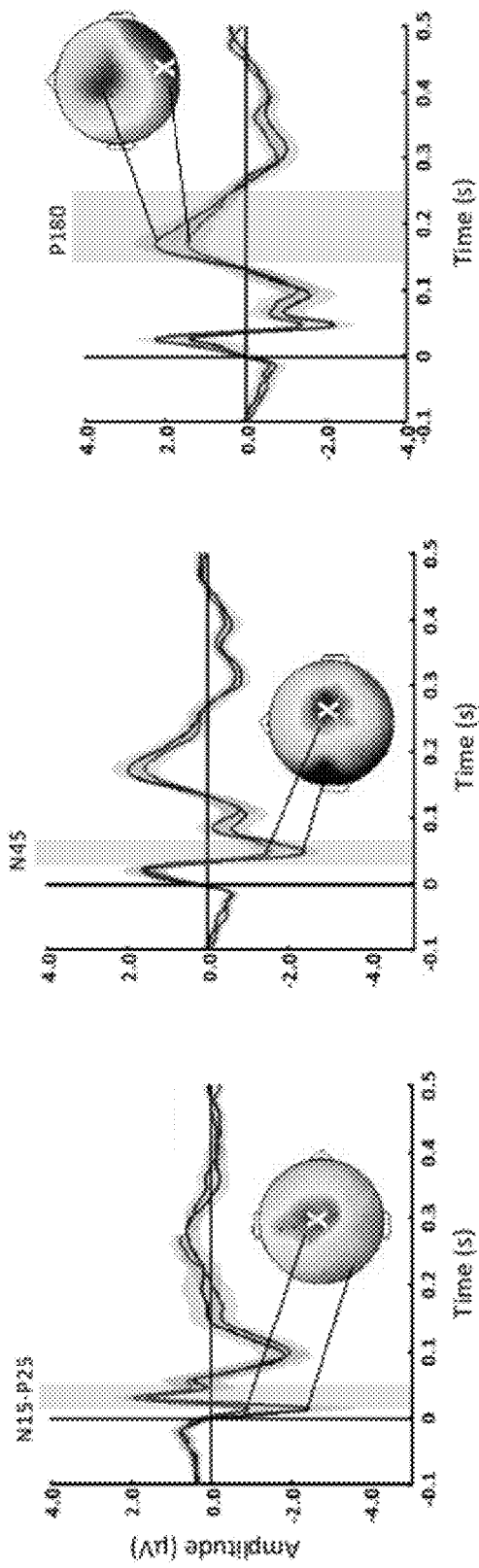

FIG. 5 includes graphical images depicting Compound A modulation of TEPs amplitude at highest concentration. TEPs grand-averaged over channels which showed significant drug-induced effects. Compared to pre-dose, Compound A induced suppression of the N15-P25 component, N45 and P180 components. TEP data are averaged over 16 participants with post-dose conditions selected at highest drug exposure during TMS evaluation. White "x"s on the topographic scalp distributions indicate regions of positive t-statistics, whereas the dark regions without "x"s indicate negative t-statistics.

Figure 6:
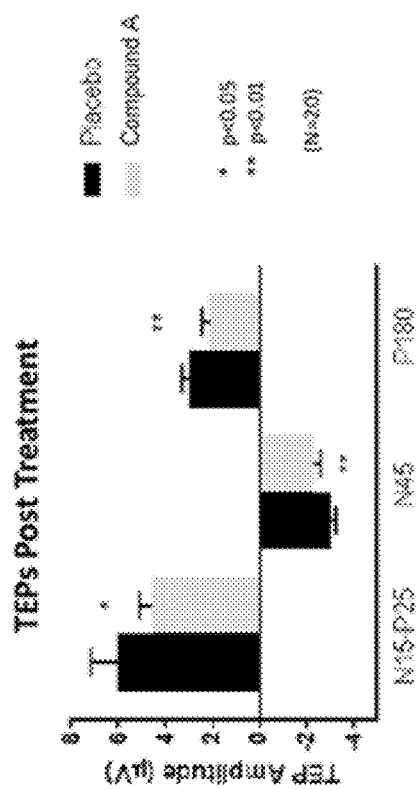

FIG. 6 is a graphical image of TEPs post treatment with Compound A and placebo showing TEP amplitude (μV) (y-axis) at N15-P25, N45, and P180 time points after TMS pulse (x-axis).

Figure 7:
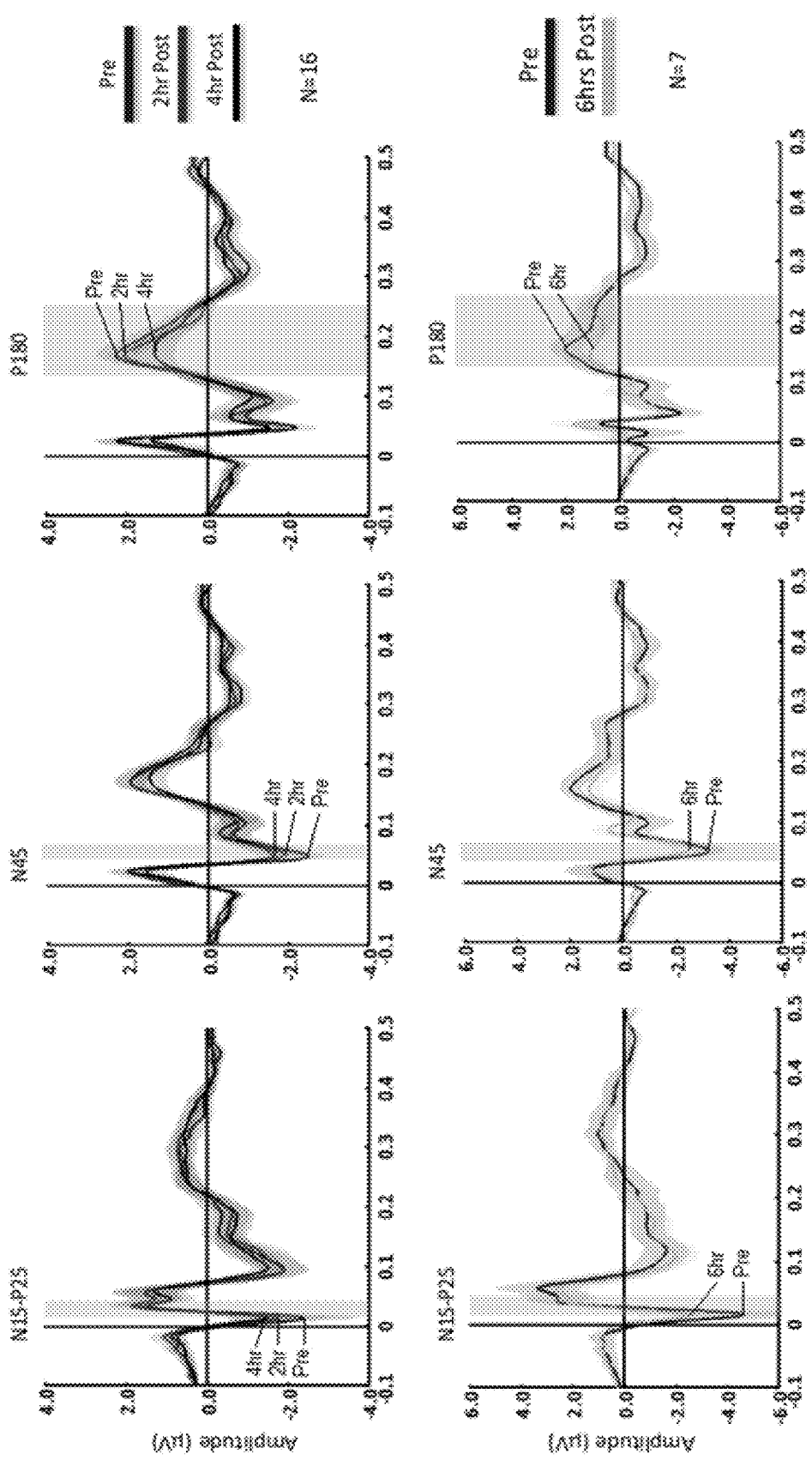

FIG. 7 includes graphical images depicting the effect of Compound A on TEPs at 2, 4, and 6 hours after dosing. Shown are grand-averaged TEPs recorded before dosing (Pre) and at 2 h post dosing (2 hr), 4 h post dosing (4 hr), and 6 h post dosing (6 hr). Compound A fingerprints which include the reduction of the N15-P25, N45 and P180 components reflect increasing plasma exposure over time.

Figure 8:
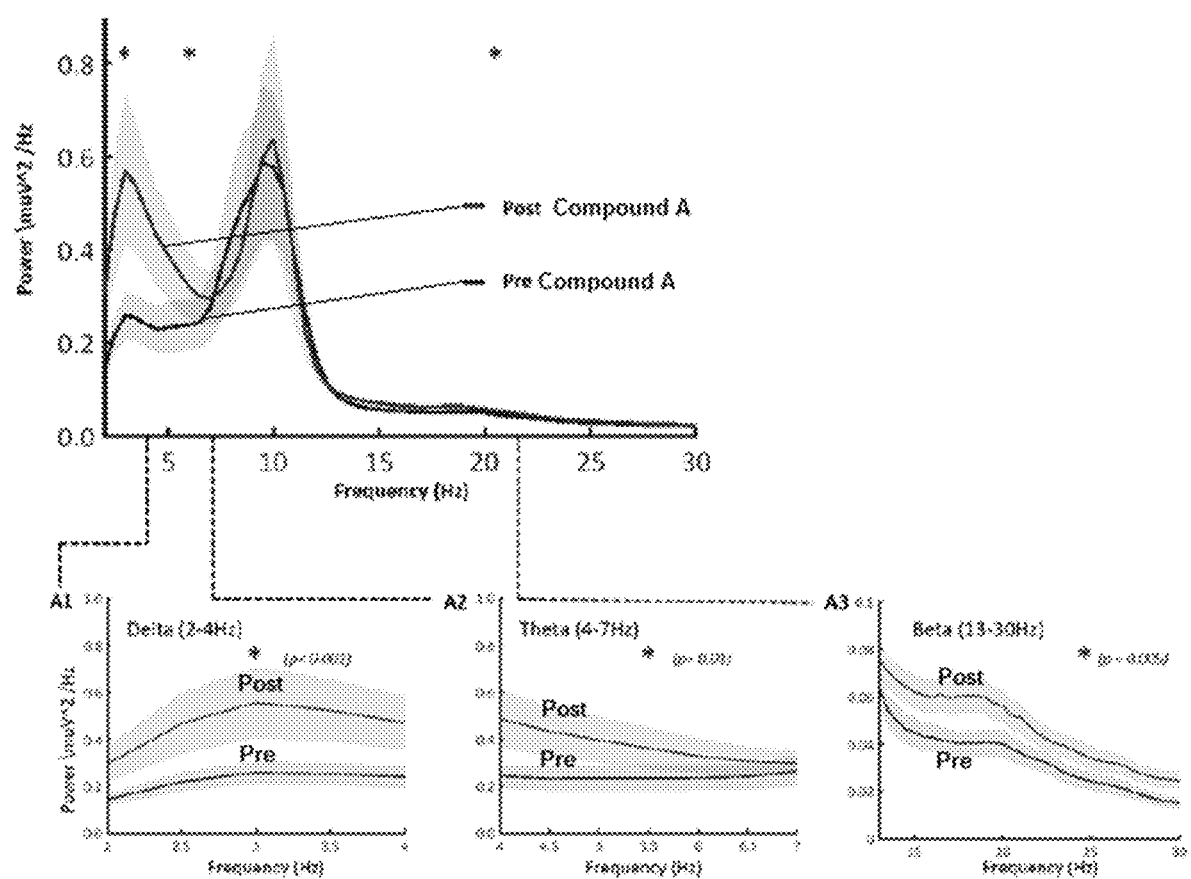

FIG. 8 illustrates drug-induced modulations of spontaneous brain oscillations before and after treatment with Compound A. Panel A shows the grand-averaged power spectrum (n=16) before (Pre) and after (Post) intake of Compound A. The significant increase of delta, theta and beta power are indicated by asterisk and shown for each specific frequency band in the lower panels A1, A2 and A3, respectively.

Figure 9:
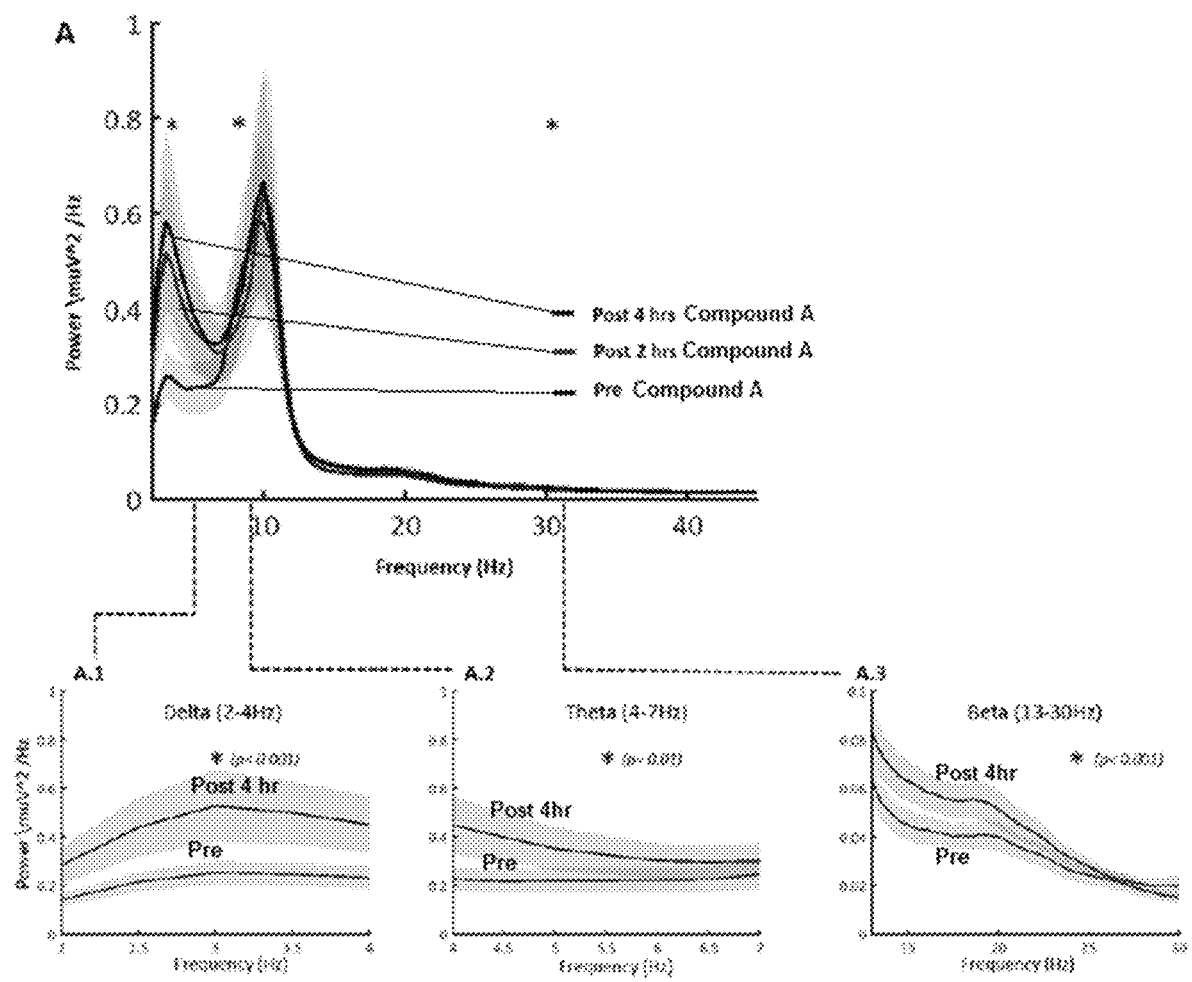

FIG. 9 illustrates drug-induced modulations of spontaneous brain oscillations over time after Compound A intake. Panel A shows the grand-averaged (n=16) power spectrum (n=16) before (Pre), at 2 h (Post 2 hr) and at 4 h (Post 4 hr) after intake of Compound A. The significant increase of delta, theta and beta power are indicated by asterisk and shown for each specific frequency band in the lower panels A1, A2 and A3, respectively.

Figure 10:
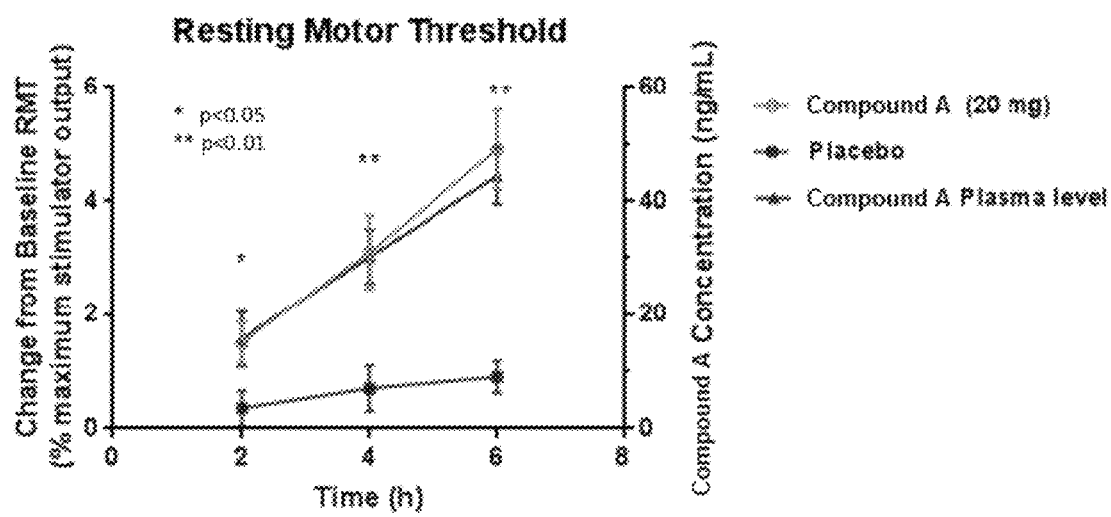

FIG. 10 is a graphical image depicting the Compound A time effect of resting motor threshold showing change from baseline RMT (% maximum stimulator output [% MSO]) (left y-axis) and Compound A concentration (ng/mL) (right y-axis) over time (hours) (x-axis). For Compound A, n=19, 20 and 16 at 2, 4, and 6 h post-dose, respectively. For placebo, n=20, 20, and 16 at 2, 4, and 6 h post-dose, respectively. Mean±SEM is shown.

Figure 11:
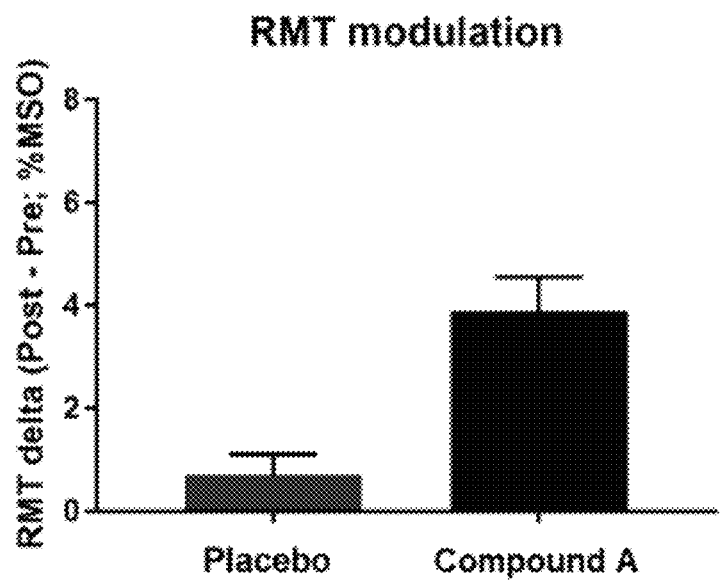

FIG. 11 is a graphical image depicting the Compound A concentration effect of RMT modulation showing RMT delta (Post-Pre; % MSO) (y-axis) and Compound A and placebo (x-axis). Average high concentration of Compound A=45 ng/mL.

Figure 12:
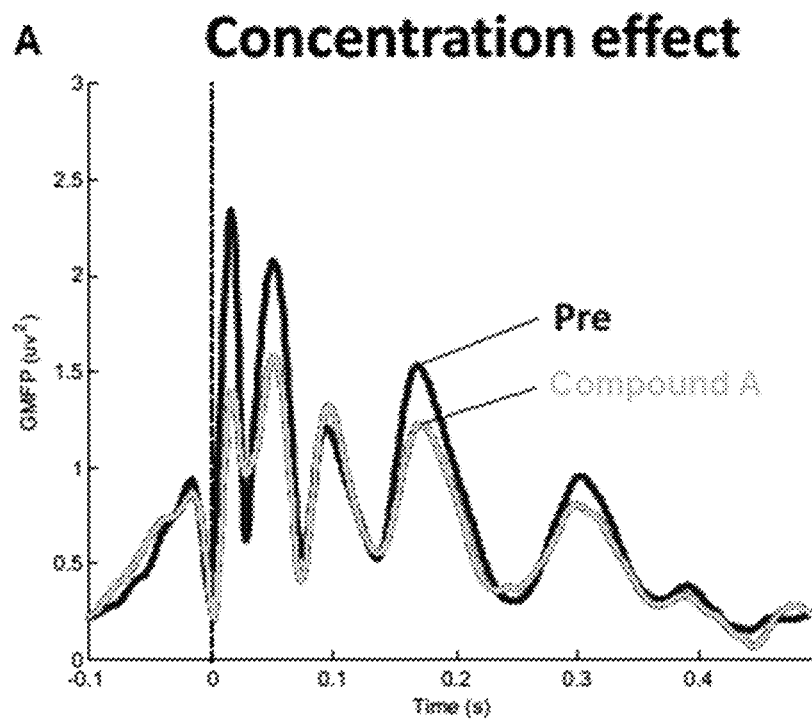
Figure 12:
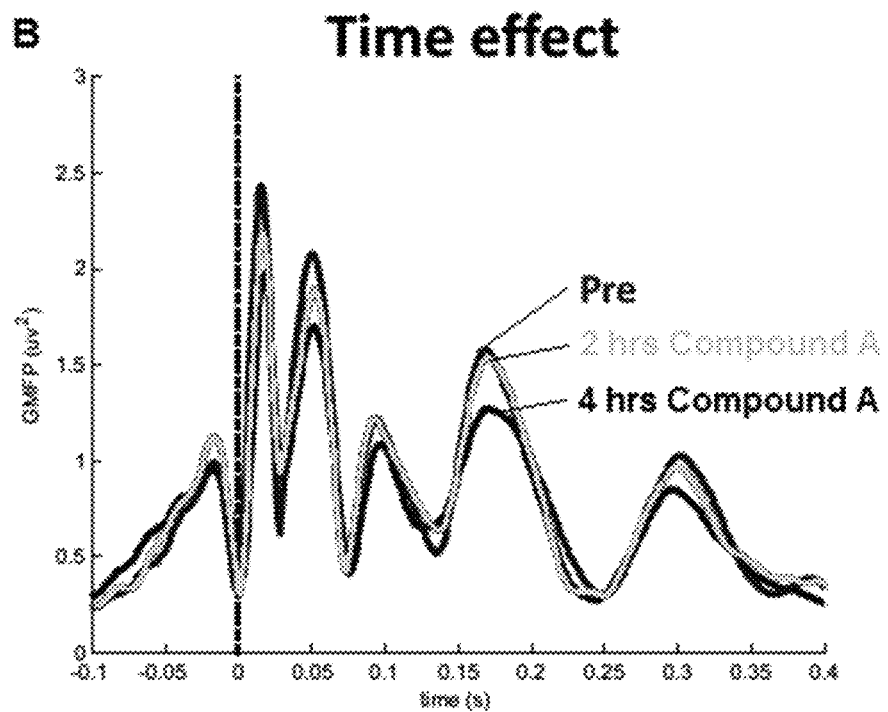

FIG. 12 includes graphical images depicting the concentration effect of pre-dose (Pre) versus post-dose Compound A showing global mean field power (GMFP) (uv2) (y-axis) over time (seconds) (x-axis) (A) and time effect of pre-dose (Pre) versus post-dose at 2 and 4 hours of Compound A showing GMFP (uv2) (y-axis) over time (seconds) (x-axis) (B). Average high concentration of Compound A=45 ng/mL.

4. DETAILED DESCRIPTION

The effect of food on a drug can significantly impact patient outcomes by affecting the pharmacokinetics and pharmacodynamics of the drug. This interaction can potentially lead to reduced drug absorption and decreased efficacy or increased drug absorption and increased efficacy. Food can also have either a positive or negative effect on the incidence and severity of adverse events associated with drug use. Whether a drug's bioavailability and or exposure to a patient is affected by the intake of food is not predictable without extensive testing. See, for example, Heimbach, T. et al., "Case Studies for Practical Food Effect Assessments across BCS/BDDCS Class Compounds using In Silico, In Vitro, and Preclinical In Vivo Data", *The AAPS Journal* (2012), Vol. 15, No. 1, pp. 143-158.

In certain embodiments, the present disclosure provides improved methods of therapy and administration that are based on the application of the unexpected finding that oral administration of Compound A to a human under fed conditions (i.e., with food or in temporal proximity to the ingestion of food) significantly enhances the bioavailability and exposure of Compound A as compared to the oral administration of Compound A to a human under fasted conditions (i.e., without food or in temporal proximity to the ingestion of food). This finding is unexpected in view of the results of a non-human primate study wherein the bioavailability and exposure of Compound A were not enhanced when Compound A was orally administered under fed conditions as compared to fasted conditions.

This finding is also unexpected in view of the lack of food effect on the bioavailability and exposure of retigabine, another potassium channel opener, as described above, after oral administration (see, e.g. page 2 of the United States Food and Drug Administration (FDA) Approved Labeling Text, dated Mar. 15, 2012, for Potiga, the trade name for retigabine; and Harris, J. A and Murphy, J. A., "Retigabine (ezogabine) as add-on therapy for partial onset seizures: an update for clinicians", *Therapeutic Advances in Chronic Disease* (2011), 2(6), pp. 371-376).

In addition, Compound A cannot form chromophoric dimers analogous to the chromophoric dimers formed by retigabine. Therefore, the blue-grey discoloration of the skin, lips or nails and changes in retinal pigmentation in human patients appearing after long term use of retigabine would not be expected to occur after long term use of Compound A.

In the following disclosure, certain specific details are set forth in order to provide a thorough understanding of various embodiments. However, one skilled in the art will understand that the methods and uses described herein may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, the term "about" as used herein means±20% of the stated value, and in more specific embodiments means±10%, ±5%, ±2%, and ±1% of the stated value.

4.1. Definitions

As used in the specification and appended claims, unless specified to the contrary, the following terms and abbreviations have the meaning indicated:

"Compound A" refers to the compound having the following formula:

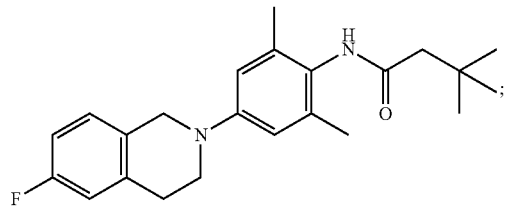 [SMILES: Cc1cc(N2CCc3cc(F)ccc3C2)cc(C)c1NC(=O)CC(C)(C)C]

and having a chemical name of N-[4-(6-fluoro-3,4-dihydro-1H-isoquinolin-2-yl)-2,6-dimethylphenyl]-3,3-dimethylbutanamide. Preparation of Compound A and its use as a Kv7.2/Kv7.3 (KCNQ2/3) opener is disclosed in U.S. Pat. Nos. 8,293,911 and 8,993,593. The mechanism of action of Compound A is different from most known AED's in that it involves potentiation or enhanced opening of the voltage-gated potassium channels Kv7.2 and Kv7.3 (Kv7.2/Kv7.3), which are important in controlling neuronal excitability. Compound A is used in the methods and uses described herein.

"AUC" refers to the area under the plasma concentration versus time curve. The AUC reflects the actual systemic exposure to Compound A after extravascular administration of a dose of Compound A and is expressed in the hours times the concentration of Compound A in the plasma. For purposes of the present disclosure, the AUC is expressed in hours times ng/mL.

"$AUC_{inf}$" refers to the AUC from time zero to infinity.

"$AUC_{infobs}$" refers to the AUC from time zero to infinity as observed.

"AUC$_{last}$" refers to the AUC from time zero to last detectable plasma concentration.

"% AUC$_{ext}$" refers to the AUC extrapolated from time zero to infinity as a percentage of total AUC.

"Bioavailability" refers to the rate and extent to which Compound A is absorbed and becomes available systemically for further distribution to the site of action.

"C$_{max}$" refers to the observed maximal plasma concentration.

"h" refers to hour or hours.

"High-fat meal" refers to any food product, solid or liquid, with approximately 50 percent of the total caloric content of the food product coming from fat.

"High-calorie meal" refers to any meal having approximately 800 to 1000 calories. A representative high-fat, high-calorie meal should derive approximately 150, 250, and 500-600 calories from protein, carbohydrate and fat, respectively.

"SD" refers to standard deviation.

"Seizure disorders" refers to seizures and disorders associated with seizures such as partial onset (focal) seizures, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia. In certain embodiments, the term "seizure disorder" refers to focal onset epilepsy, also known as partial onset (focal) epilepsy.

"t$\frac{1}{2}_{\lambda z}$" refers to the terminal elimination half-life of Compound A from plasma (i.e., the time required for the plasma concentration of Compound A to be reduced by one-half during the terminal elimination phase).

"T$_{max}$" refers to the time to reach maximum (peak) plasma concentration following extravascular administration of Compound A.

"Therapeutically effective amount" as used herein refers to an amount of Compound A that is sufficient to treat the indicated disease, disorder, or condition or have the desired stated effect, including ameliorating or preventing the disease, disorder, or condition or one or more mechanisms underlying the disease, disorder, or condition. In certain embodiments, when Compound A is administered for the treatment of a seizure disorder, therapeutically effective amount refers to a range of amounts of Compound A which, upon administration to a human, treats, ameliorates or prevents a seizure disorder in the human, or exhibits a detectable therapeutic or preventative effect in the human having a seizure disorder. The effect is detected by, for example, a reduction in seizures (frequency) or by the severity of seizures (quality). The precise therapeutically effective amount for a given human will depend upon the human's size and health, the nature and extent of the seizure disorder, the presence of any concomitant medications, and other variables known to those of skill in the art. The therapeutically effective amount for a given situation can be determined by routine experimentation and is within the capabilities of the clinician.

"Treatment" as used herein refers to therapeutic applications associated with administering Compound A that ameliorate or prevent the indicated disease, disorder, or condition or one or more underlying mechanisms of said disease, disorder, or condition, including slowing or stopping progression of the disease, disorder or condition or one or more of the underlying mechanisms. In certain embodiments, when Compound A is administered for the treatment of a seizure disorder, treatment refers to therapeutic applications to slow or stop progression of a seizure disorder, prophylactic application to prevent development of a seizure disorder, and/or reversal of a seizure disorder. Reversal of a seizure disorder differs from a therapeutic application which slows or stops a seizure disorder in that with a method of reversing, not only is progression of a seizure disorder completely stopped, cellular behavior is moved to some degree toward a normal state that would be observed in the absence of the seizure disorder.

"Under fed conditions" refers to the condition of having consumed food during the time period between from about 4 hours prior to the oral administration of an effective amount (e.g., within the therapeutically effective dose range) of Compound A to about 4 hours after the administration of Compound A. The food may be a solid, liquid, or mixture of solid and liquid food with sufficient bulk and fat content that it is not rapidly dissolved and absorbed in the stomach. In some instances, the food is a meal, such as breakfast, lunch, dinner or, alternatively, baby food (e.g., formula or breast milk). The therapeutically effective amount of Compound A may be orally administered to the subject, for example, between about 30 minutes prior to about 2 hours after eating a meal, most advantageously, the dosage unit of Compound A is orally administered during a meal or within 15 minutes after eating a meal.

"Under fasted conditions" refers to the condition of not having consumed food during the time period between from at least 4 hours prior to the oral administration of a therapeutically effective amount of Compound A to about 4 hours after administration of Compound A.

4.2. Embodiments

In some embodiments, the present disclosure is directed to a method of treating a disease, disorder, or condition associated with Kv7 potassium channel dysfunction in a human in need thereof, comprising orally administering a therapeutically effective amount of Compound A to the human under fed conditions. In certain instances, the disease, disorder, or condition associated with Kv7 potassium channel dysfunction is a seizure disorder, such as focal onset epilepsy.

In certain embodiments, the present disclosure is directed to a method of treating a disease, disorder, or condition associated with Kv7 potassium channel dysfunction in a human in need thereof, comprising orally administering a therapeutically effective amount of Compound A to the human from between 30 minutes prior to consuming food until 2 hours after consuming food. In certain instances, the disease, disorder, or condition associated with Kv7 potassium channel dysfunction is a seizure disorder, such as focal onset epilepsy.

In some embodiments, the present disclosure is directed to a compound for use in treating a disease, disorder, or condition associated with Kv7 potassium channel dysfunction in a human in need thereof, wherein the compound is Compound A and a therapeutically effective amount of the compound is orally administered to the human under fed conditions. In certain instances, the disease, disorder, or condition associated with Kv7 potassium channel dysfunction is a seizure disorder, such as focal onset epilepsy.

In certain embodiments, the present disclosure is directed to a compound for use in treating a disease, disorder, or condition associated with Kv7 potassium channel dysfunction in a human in need thereof, wherein the compound is Compound A and a therapeutically effective amount of the compound is orally administered to the human from between 30 minutes prior to consuming food until 2 hours after consuming food. In certain instances, the disease, disorder, or condition associated with Kv7 potassium channel dysfunction is a seizure disorder, such as focal onset epilepsy.

In embodiments directed to a disease, disorder, or condition associated with Kv7 potassium channel dysfunction, in some instances, the method enhances opening of a Kv7 potassium channel, such as one or more of Kv7.2, Kv7.3, Kv7.4, and Kv7.5. In certain instances, the method or use is selective for enhancing the opening of a Kv7 potassium channel selected from one or more of Kv7.2, Kv7.3, Kv7.4, and Kv7.5 over Kv7.1. In some embodiments, the method or use is selective for Kv7.2, optionally over Kv7.1. In other embodiments, the method or use is selective for Kv7.3, optionally over Kv7.1. In yet other embodiments, the method or use is selective for Kv7.4, optionally over Kv7.1. In yet further other embodiments, the method or use is selective for Kv7.5, optionally over Kv7.1. In certain embodiments, the method or use is selective for Kv7.2 and Kv7.3, optionally over Kv7.1.

In one embodiment, the present disclosure provides a method of treating a seizure disorder in a human in need thereof, comprising orally administering an amount of Compound A to the human under fed conditions, wherein the amount of Compound A is sufficient to treat the seizure disorder in the human. In certain embodiments, the amount is sufficient to reduce the severity of seizures, the frequency of seizures, or both.

In one embodiment, the present disclosure provides a compound for use in treating a seizure disorder in a human in need thereof, wherein the compound is Compound A and the compound is orally administered to the human under fed conditions. In certain embodiments, the amount is sufficient to reduce the severity of seizures, the frequency of seizures, or both.

In one embodiment, the present disclosure provides a method of treating a seizure disorder in a human in need thereof, comprising orally administering an amount of Compound A to the human from between 30 minutes prior to consuming food until 2 hours after consuming food, wherein the amount of Compound A is sufficient to treat the seizure disorder in the human. In certain embodiments, the amount is sufficient to reduce the severity of seizures, the frequency of seizures, or both.

In one embodiment, the present disclosure provides a compound for use in treating a seizure disorder in a human in need thereof, wherein the compound is Compound A and the compound is orally administered to the human from between 30 minutes prior to consuming food until 2 hours after consuming food. In certain embodiments, the amount is sufficient to reduce the severity of seizures, the frequency of seizures, or both.

In one embodiment, the present disclosure provides a method of treating a seizure disorder in a human in need thereof, comprising orally administering an amount of Compound A to the human under fed conditions, wherein the amount of Compound A is from 2 to 200 mg.

In one embodiment, the present disclosure provides a method of treating a seizure disorder in a human in need thereof, comprising orally administering an amount of Compound A to the human from between 30 minutes prior to consuming food until 2 hours after consuming food, wherein the amount of Compound A is from 2 to 200 mg.

In one embodiment, the present disclosure provides a method of increasing one or more of the $C_{max}$, $AUC_{inf}$, $T_{max}$, or $t\frac{1}{2}_{\lambda z}$ of Compound A in a human receiving an oral administration of Compound A, comprising orally administering an amount of Compound A to the human under fed conditions. In certain embodiments, the method increases one or more of $C_{max}$, $AUC_{inf}$, $T_{max}$, or $t\frac{1}{2}_{\lambda z}$ as compared to when the same amount of Compound A is orally administered to the human under fasted conditions.

In one embodiment, the present disclosure provides a compound for use in increasing one or more of the $C_{max}$, $AUC_{inf}$, $T_{max}$, or $t\frac{1}{2}_{\lambda z}$ of the compound in a human receiving an oral administration of the compound, wherein the compound is Compound A and the compound is orally administered to the human under fed conditions. In certain embodiments, the oral administration increases one or more of $C_{max}$, $AUC_{inf}$, $T_{max}$, or $t\frac{1}{2}_{\lambda z}$ as compared to when the same amount of Compound A is orally administered to the human under fasted conditions.

In one embodiment, the present disclosure provides a method of increasing one or more of the $C_{max}$, $AUC_{inf}$, $T_{max}$, or $t\frac{1}{2}_{\lambda z}$ of Compound A in a human receiving an oral administration of Compound A, comprising orally administering an amount of Compound A to the human from between 30 minutes prior to consuming food until 2 hours after consuming food. In certain embodiments, the method increases one or more of $C_{max}$, $AUC_{inf}$, $T_{max}$, or $t\frac{1}{2}_{\lambda z}$ as compared to when the same amount of Compound A is orally administered to the human under fasted conditions.

In one embodiment, the present disclosure provides a compound for use in increasing one or more of the $C_{max}$, $AUC_{inf}$, $T_{max}$, or $t\frac{1}{2}_{\lambda z}$ of the compound in a human receiving an oral administration of the compound, wherein the compound is Compound A and the compound is orally administered to the human from between 30 minutes prior to consuming food until 2 hours after consuming food. In certain embodiments, the oral administration increases one or more of $C_{max}$, $AUC_{inf}$, $T_{max}$, or $t\frac{1}{2}_{\lambda z}$ as compared to when the same amount of Compound A is orally administered to the human under fasted conditions.

In certain embodiments, the present disclosure provides a method of increasing bioavailability or one or more of the $C_{max}$, $AUC_{inf}$, $T_{max}$, or $t\frac{1}{2}_{\lambda z}$ of Compound A in a human receiving an oral administration of Compound A, comprising (a) informing the human that orally administering Compound A under fed conditions or from between 30 minutes prior to consuming food until 2 hours after consuming food increases the bioavailability or one or more of the $C_{max}$, $AUC_{inf}$, $T_{max}$, or $t\frac{1}{2}_{\lambda z}$ of Compound A; and (b) in reliance on step (a), orally administering Compound A under fed conditions or from between 30 minutes prior to consuming food until 2 hours after consuming food.

In certain such embodiments, the probability that (b) occurs (i.e., the administration occurs under fed conditions or from between 30 minutes prior to consuming food until 2 hours after consuming food) is increased relative to the method in the absence of step (a).

In one embodiment, the present disclosure provides a method of orally administering Compound A to a human in need thereof, comprising orally administering Compound A to the human under fed conditions. In certain embodiments, the method increases one or more of $C_{max}$, $AUC_{inf}$, $T_{max}$, or $t\frac{1}{2}_{\lambda z}$ of Compound A as compared to when the same amount of Compound A is orally administered to the human under fasted conditions.

In one embodiment, the present disclosure provides a method of orally administering Compound A to a human in need thereof, comprising orally administering Compound A to the human from between 30 minutes prior to consuming food until 2 hours after consuming food. In certain embodiments, the method increases one or more of $C_{max}$, $AUC_{inf}$, $T_{max}$, or $t\frac{1}{2}_{\lambda z}$ of Compound A as compared to when the same amount of Compound A is orally administered to the human under fasted conditions.

In one embodiment, the present disclosure provides a method of reducing a dose of Compound A that is orally administered to a human in need thereof as part of a treatment regimen, comprising orally administering a reduced dose of Compound A to the human under fed conditions. In certain embodiments, the reduced dose is a lower dose than would be needed to achieve one of more of the same $C_{max}$, $AUC_{inf}$, $T_{max}$, or $t\frac{1}{2}_{\lambda z}$ of Compound A when orally administered to the human under fasted conditions.

In one embodiment, the present disclosure provides a compound for use in reducing a dose of the compound that is orally administered to a human in need thereof as part of a treatment regimen, wherein the compound is Compound A and the compound is orally administered to the human under fed conditions. In certain embodiments, the reduced dose is a lower dose than would be needed to achieve one or more of the same $C_{max}$, $AUC_{inf}$, $T_{max}$, or $t\frac{1}{2}_{\lambda z}$ of Compound A when orally administered to the human under fasted conditions.

In one embodiment, the present disclosure provides a method of reducing a dose of Compound A that is orally administered to a human in need thereof as part of a treatment regimen, comprising orally administering a reduced dose of Compound A to the human from between 30 minutes prior to consuming food until 2 hours after consuming food. In certain embodiments, the reduced dose is a lower dose than would be needed to achieve one of more of the same $C_{max}$, $AUC_{inf}$, $T_{max}$, or $t\frac{1}{2}_{\lambda z}$ of Compound A when orally administered to the human under fasted conditions.

In one embodiment, the present disclosure provides a compound for use in reducing a dose of the compound that is orally administered to a human in need thereof as part of a treatment regimen, wherein the compound is Compound A and the compound is orally administered to the human from between 30 minutes prior to consuming food until 2 hours after consuming food. In certain embodiments, the reduced dose is a lower dose than would be needed to achieve one of more of the same $C_{max}$, $AUC_{inf}$, $T_{max}$, or $t\frac{1}{2}_{\lambda z}$ of Compound A when orally administered to the human under fasted conditions.

In one embodiment, the present disclosure provides a method of treating a seizure disorder in a human in need thereof, comprising orally administering a therapeutically effective amount of Compound A to the human. In certain embodiments, the method produces, for Compound A, one or more of:

a $C_{max}$ of at least 40 ng/mL, such at least 45, 50, 55, 60, 65, 70, 75, or 80 ng/mL, an $AUC_{inf}$ of at least 2500 h·ng/mL, such as at least 2600, 2700, 2800, 2900, 3000, 3100, 3300, 3500, 3700, or 4000 h·ng/mL, a $T_{max}$ of at least 3.25 h, such as at least 3.5, 3.75, 4, 4.25, or 4.5 h, or a $t\frac{1}{2}_{\lambda z}$ of at least 130 h, such as at least 150, 170, 190, or 210.

In one embodiment, the present disclosure provides a compound for use in treating a seizure disorder in a human in need thereof, wherein the compound is Compound A and the compound is orally administered to the human. In certain embodiments, the oral administration produces, for Compound A, one or more of:

a $C_{max}$ of at least 40 ng/mL, such at least 45, 50, 55, 60, 65, 70, 75, or 80 ng/mL;

an $AUC_{inf}$ of at least 2500 h·ng/mL, such as at least 2600, 2700, 2800, 2900, 3000, 3100, 3300, 3500, 3700, or 4000 h·ng/mL, a $T_{max}$ of at least 3.25 h, such as at least 3.5, 3.75, 4, 4.25, or 4.5 h, or a $t\frac{1}{2}_{\lambda z}$ of at least 130 h, such as at least 150, 170, 190, or 210.

In certain embodiments, the increase in one or more of the $C_{max}$, $AUC_{inf}$, $T_{max}$, or $t\frac{1}{2}_{\lambda z}$ of Compound A effected by the present methods and uses is not dependent on the type of food consumed by the human, e.g., the food may include a high-fat or high-calorie meal or may not.

In one embodiment, the present disclosure provides a method of increasing resting motor threshold (RMT) or active motor threshold (AMT) in a human in need thereof, comprising orally administering an amount of Compound A to the human, optionally under fed conditions or from between 30 minutes prior to consuming food until 2 hours after consuming food. In certain embodiments, the amount of Compound A is sufficient to increase RMT or AMT in the human.

In one embodiment, the present disclosure provides a compound for use in increasing resting motor threshold (RMT) or active motor threshold (AMT) in a human in need thereof, wherein the compound is Compound A and an amount of the compound is orally administered to the human, optionally under fed conditions or from between 30 minutes prior to consuming food until 2 hours after consuming food. In certain embodiments, the amount of Compound A is sufficient to increase RMT or AMT in the human. In certain embodiments, the amount of Compound A is from 2 to 200 mg.

In one embodiment, the present disclosure provides a method of increasing resting motor threshold (RMT) or active motor threshold (AMT) in a human in need thereof, comprising orally administering an amount of Compound A to the human, optionally under fed conditions or from between 30 minutes prior to consuming food until 2 hours after consuming food. In certain embodiments, the amount of Compound A is from 2 to 200 mg.

In one embodiment, the present disclosure provides a method of decreasing corticospinal or cortical excitability in a human in need thereof, comprising orally administering an amount of Compound A to the human, optionally under fed conditions or from between 30 minutes prior to consuming food until 2 hours after consuming food, wherein the amount of Compound A is sufficient to increase corticospinal or cortical excitability in the human.

In one embodiment, the present disclosure provides a compound for use in decreasing corticospinal or cortical excitability in a human in need thereof, wherein the compound is Compound A and an amount of the compound is orally administered to the human, optionally under fed conditions or from between 30 minutes prior to consuming food until 2 hours after consuming food, wherein the amount of Compound A is sufficient to increase corticospinal or cortical excitability in the human. In certain embodiments, the amount of Compound A is from 2 to 200 mg.

In one embodiment, the present disclosure provides a method of decreasing corticospinal or cortical excitability in a human in need thereof, comprising orally administering an amount of Compound A to the human, optionally under fed conditions or from between 30 minutes prior to consuming food until 2 hours after consuming food, wherein the amount of Compound A is from 2 to 200 mg.

In one embodiment of the present disclosure, the oral administration of Compound A to a human under fed conditions enhances the bioavailability and exposure of Compound A upon oral administration. Such conditions have surprisingly been found to significantly increase the bioavailability and exposure of Compound A in humans upon oral administration. In more specific embodiments, under fed conditions comprises the consumption of a food product simultaneously with, or in close proximity to, the oral administration of Compound A.

In some, but not all, embodiments of the present disclosure, the food product is a high-fat, high calorie meal. Representative high-fat meals have approximately 50 percent of total caloric content of the meal coming from fat and representative high-calorie meals have approximately 800 to 1000 calories. A representative meal should derive approximately 150, 250, and 500-600 calories from protein, carbohydrate, and fat, respectively. The amount of food product consumed with, or in temporal proximity to, the oral administration of Compound A should be sufficient such that enhanced bioavailability and exposure of Compound A is achieved.

In some embodiments, the oral administration of Compound A to a human in need thereof according to the methods and uses described herein is from between 30 minutes prior to consuming food until 2 hours after consuming food. In some aspects, oral administration can occur from about 60, 45, 30, 25, 20, 15, 10, or 5 minutes prior to consuming food to about 5, 10, 15, 30, 45, 60, 75, 90, 105, 120, 135, 150, 165, 180, 195, 210, 225, or 240 minutes after consuming food. In some aspects, Compound A can be administered concurrently with the consumption of food, or up to 15 minutes of having consumed food.

In some embodiments, the oral administration of Compound A to a human in need thereof according to the methods described herein increases one or more of the $C_{max}$, $AUC_{inf}$, $T_{max}$, or $t^{1}/_{2\lambda z}$ of Compound A as compared to when the same amount of Compound A is orally administered to the human under fasted conditions. In some embodiments, the oral administration of Compound A to the human increases the $C_{max}$ of Compound A as compared to when the same amount of Compound A is orally administered to the human under fasted conditions. In some aspects, the oral administration increases $AUC_{inf}$ compared to fasted conditions. In some aspects, the oral administration increases $T_{max}$ compared to fasted conditions. In some aspects, the oral administration increases $t^{1}/_{2\lambda z}$ compared to fasted conditions. In some aspects, the oral administration increases $C_{max}$ and $AUC_{inf}$ compared to fasted conditions. In some aspects, the oral administration increases $C_{max}$ and $T_{max}$ compared to fasted conditions. In some aspects, the oral administration increases $C_{max}$ and $t^{1}/_{2\lambda z}$ compared to fasted conditions. In some aspects, the oral administration increases $AUC_{inf}$ and $T_{max}$ compared to fasted conditions. In some aspects, the oral administration increases $AUC_{inf}$ and $t^{1}/_{2\lambda z}$ compared to fasted conditions. In some aspects, the oral administration increases $T_{max}$ and $t^{1}/_{2\lambda z}$ compared to fasted conditions. In some aspects, the oral administration increases $C_{max}$, $AUC_{inf}$, and $T_{max}$ compared to fasted conditions. In some aspects, the oral administration increases $C_{max}$, $AUC_{inf}$, and $t^{1}/_{2\lambda z}$ compared to fasted conditions. In some aspects, the oral administration increases $C_{max}$, $T_{max}$, and $t^{1}/_{2\lambda z}$ compared to fasted conditions. In some aspects, the oral administration increases $AUC_{inf}$, $T_{max}$, and $t^{1}/_{2\lambda z}$ compared to fasted conditions. In some aspects, the oral administration increases $C_{max}$, $AUC_{inf}$, $T_{max}$, and $t^{1}/_{2\lambda z}$ compared to fasted conditions.

In some embodiments, the oral administration of Compound A to a human in need thereof according to the methods described herein increases the $C_{max}$ of Compound A as compared to when the same amount of Compound A is orally administered to the human under fasted conditions. In some aspects, the increase in $C_{max}$ is at least 50%, such as at least 60%, 75%, 85%, 100%, 125%, 150%, 200%, 250%, or 300%. In some aspects, the increase in $C_{max}$ is at least 100%, 150%, or 200%, such at least 100%. In some aspects, the increase in $C_{max}$ can range of from about 50% to about 500%, e.g., from about 50% to about 400%, from about 60% to about 350%, from about 70% to about 300%, from about 80% to about 250%, or from about 100% to about 200%, such as from about 50%, 60%, 70%, 80%, 90%, or 100% to about 200%, 250%, 300%, 350%, 400%, 450%, or 500%, including about or at least about 60%, 70%, 80%, 90%, 100%, 110%, 120%, 130%, 140%, 150%, 160%, 170%, 180%, 190%, or 200%.

In one embodiment of the present disclosure, the ratio of the Cmax following oral administration of Compound A under fed conditions to the $C_{max}$ following oral administration of Compound A under fasted conditions is greater than 1.2. In specific embodiments, the ratio is greater than 1.3, greater than 1.5, greater than 2.0, greater than 2.5, greater than 3.0, greater than 3.5, greater than 4.0, greater than 4.5, greater than 5.0, greater than 5.5, greater than 6.0 or greater than 6.5.

In some embodiments, the $C_{max}$ of Compound A is increased to at least 40 ng/mL. In some aspects, the $C_{max}$ of Compound A can increase to a range of from 20 ng/mL to about 200 ng/mL, e.g., from about 25 to about 200 ng/mL, from about 30 to about 200 ng/mL, from about 35 to about 200 ng/mL, from about 40 to about 175 ng/mL, from about 40 to about 150 ng/mL, from about 40 to about 125 ng/mL, from about 40 to about 100 ng/mL, from about 40 to about 90 ng/mL, from about 40 to about 80 ng/mL, from about 40 to about 70 ng/mL, from about 40 to about 60 ng/mL, or from about 40 to about 50 ng/mL, such as about 40 ng/mL, 41 ng/mL, 42 ng/mL, 43 ng/mL, 44 ng/mL, 45 ng/mL, 46 ng/mL, 47 ng/mL, 48 ng/mL, 49 ng/mL, 50 ng/mL, 51 ng/mL, 52 ng/mL, 53 ng/mL, 54 ng/mL, 55 ng/mL, 56 ng/mL, 57 ng/mL, 58 ng/mL, 59 ng/mL, 60 ng/mL, 61 ng/mL, 62 ng/mL, 63 ng/mL, 64 ng/mL, 65 ng/mL, 66 ng/mL, 67 ng/mL, 68 ng/mL, 69 ng/mL, 70 ng/mL, 71 ng/mL, 72 ng/mL, 73 ng/mL, 74 ng/mL, 75 ng/mL, 76 ng/mL, 77 ng/mL, 78 ng/mL, 79 ng/mL, 80 ng/mL, 81 ng/mL, 82 ng/mL, 83 ng/mL, 84 ng/mL, 85 ng/mL, 86 ng/mL, 87 ng/mL, 88 ng/mL, 89 ng/mL, 90 ng/mL, 91 ng/mL, 92 ng/mL, 93 ng/mL, 94 ng/mL, 95 ng/mL, 96 ng/mL, 97 ng/mL, 98 ng/mL, 99 ng/mL, or 100 ng/mL.

In some embodiments, the oral administration of Compound A to a human in need thereof according to the methods disclosed herein increases the $AUC_{inf}$ of Compound A as compared to when the same amount of Compound A is orally administered to the human under fasted conditions. In some aspects, the increase in $AUC_{inf}$ is at least 50%, such as at least 60%, 75%, 85%, 100%, 125%, 150%, 200%, or 250%. In some aspects, the increase in $AUC_{inf}$ is at least 75% or 100%. In some aspects, the increase in $AUC_{inf}$ can range of from about 50% to about 500%, e.g., from about 50% to about 400%, from about 60% to about 350%, from about 70% to about 300%, from about 80% to about 250%, or from about 100% to about 200%, such as from about 50%, 60%, 70%, 80%, 90%, or 100% to about 200%, 250%, 300%, 350%, 400%, 450%, or 500%, including about or at least about 60%, 70%, 75%, 80%, 85%, 90%, 95%, 100%, 110%, 120%, 130%, 140%, 150%, 160%, 170%, 180%, 190%, or 200%.

In some embodiments, the ratio of the $AUC_{inf}$ following oral administration of Compound A under fed conditions to the $AUC_{inf}$ following oral administration of Compound A under fasted conditions is greater than 1.2. In specific embodiments, the ratio is greater than 1.3, greater than 1.5, greater than 1.8, greater than 2.0, greater than 2.5, greater than 3.0, greater than 3.5, greater than 4.0, greater than 4.5, greater than 5.0, greater than 5.5, greater than 6.0 or greater than 6.5.

In one embodiment of the present disclosure, the ratio of the AUC following oral administration of Compound A under fed conditions to the AUC following oral administration of Compound A under fasted conditions is greater than 1.2. In specific embodiments, the ratio is greater than 1.3, greater than 1.5, greater than 2.0, greater than 2.5, greater than 3.0, greater than 3.5, greater than 4.0, greater than 4.5, greater than 5.0, greater than 5.5, greater than 6.0 or greater than 6.5.

In some embodiments, the $AUC_{inf}$ of Compound A is increased to at least 2500 h·ng/mL. In some aspects the $AUC_{inf}$ of Compound A can increase to a range of from 2000 h·ng/mL to about 5000 h·ng/mL, e.g., from about 2500 to about 5000 h·ng/mL, from about 2500 to about 4500 h·ng/mL, from about 2500 to about 4250 h·ng/mL, from about 2500 to about 4000 h·ng/mL, from about 2500 to about 3750 h·ng/mL, from about 2500 to about 3500 h·ng/mL, from about 2500 to about 3250 h·ng/mL, from about 2500 to about 3000 h·ng/mL, or from about 2500 to about 2750 h·ng/mL, such as about 2500 h·ng/mL, 2600 h·ng/mL, 2700 h·ng/mL, 2800 h·ng/mL, 2900 h·ng/mL, 3000 h·ng/mL, 3100 h·ng/mL, 3200 h·ng/mL, 3300 h·ng/mL, 3400 h·ng/mL, 3500 h·ng/mL, 3600 h·ng/mL, 3700 h·ng/mL, 3800 h·ng/mL, 3900 h·ng/mL, 4000 h·ng/mL, 4100 h·ng/mL, 4200 h·ng/mL, 4300 h·ng/mL, 4400 h·ng/mL, 4500 h·ng/mL, 4600 h·ng/mL, 4700 h·ng/mL, 4800 h·ng/mL, 4900 h·ng/mL, or 5000 h·ng/mL.

In some embodiments, the oral administration of Compound A to a human in need thereof according to the methods disclosed herein increases the $T_{max}$ of Compound A as compared to when the same amount of Compound A is orally administered to the human under fasted conditions. In some aspects, the increase in $T_{max}$ is at least 50%, such as at least 60%, 75%, 85%, 100%, 125%, 150%, 200%, or 250%. In some aspects, the increase in $T_{max}$ is at least 75% or 100%. In some aspects, the increase in $T_{max}$ can range of from about 50% to about 500%, e.g., from about 50% to about 400%, from about 60% to about 350%, from about 70% to about 300%, from about 80% to about 250%, or from about 100% to about 200%, such as from about 50%, 60%, 70%, 80%, 90%, or 100% to about 200%, 250%, 300%, 350%, 400%, 450%, or 500%, including about or at least about 60%, 70%, 75%, 80%, 85%, 90%, 95%, 100%, 110%, 120%, 130%, 140%, 150%, 160%, 170%, 180%, 190%, or 200%.

In some embodiments, the ratio of the $T_{max}$ following oral administration of Compound A under fed conditions to the $T_{max}$ following oral administration of Compound A under fasted conditions is greater than 1.2. In specific embodiments, the ratio is greater than 1.3, greater than 1.5, greater than 1.8, greater than 2.0, greater than 2.5, greater than 3.0, greater than 3.5, greater than 4.0, greater than 4.5, greater than 5.0, greater than 5.5, greater than 6.0 or greater than 6.5.

In some embodiments, the $T_{max}$ of Compound A is increased to at least 3.25 hr. In some aspects the $T_{max}$ of Compound A can increase to a range of from 3 hr to about 15 hr, e.g., from about 3.25 hr to about 15 hr, from about 3.25 hr to about 14.5 hr, from about 3.25 hr to about 14 hr, from about 3.25 hr to about 13.5 hr, from about 3.25 hr to about 13 hr, from about 3.25 hr to about 12.5 hr, from about 3.25 hr to about 12 hr, from about 3.25 hr to about 11.5 hr, from about 3.25 hr to about 11 hr, from about 3.25 hr to about 10.5 hr, from about 3.25 hr to about 10 hr, from about 3.25 hr to about 9.5 hr, from about 3.25 hr to about 9 hr, from about 3.25 hr to about 8.5 hr, from about 3.25 hr to about 8 hr, from about 3.25 hr to about 7.5 hr, from about 3.25 hr to about 7 hr, from about 3.25 hr to about 6.5 hr, from about 3.25 hr to about 6 hr, from about 3.25 hr to about 5.5 hr, from about 3.25 hr to about 5 hr, or from about 3.25 hr to about 4.5 hr, such as about 3.25 hr, 3.5 hr, 3.75 hr, 4 hr, 4.25 hr, 4.5 hr, 4.75 hr, 5 hr, 5.25 hr, 5.5 hr, 5.75 hr, 6 hr, 6.25 hr, 6.5 hr, 6.75 hr, 7 hr, 7.25 hr, 7.5 hr, 7.75 hr, 8 hr, 8.25 hr, 8.5 hr, 8.75 hr, 9 hr, 9.25 hr, 9.5 hr, 9.75 hr, or 10 hr.

In some embodiments, the oral administration of Compound A to a human in need thereof according to the methods disclosed herein increases the $t^{1}\!/\!2_{\lambda z}$ of Compound A as compared to when the same amount of Compound A is orally administered to the human under fasted conditions by at least 40% or 50%, such as at least 60%, 75%, or 100%. In some aspects, the increase in $t^{1}\!/\!2_{\lambda z}$ is at least 75%. In some aspects, the increase in $t^{1}\!/\!2_{\lambda z}$ can range of from about 50% to about 500%, e.g., from about 50% to about 400%, from about 60% to about 350%, from about 70% to about 300%, from about 80% to about 250%, or from about 100% to about 200%, such as from about 50%, 60%, 70%, 80%, 90%, or 100% to about 200%, 250%, 300%, 350%, 400%, 450%, or 500%, including about or at least about 60%, 70%, 75%, 80%, 85%, 90%, 95%, 100%, 110%, 120%, 130%, 140%, 150%, 160%, 170%, 180%, 190%, or 200%.

In some embodiments, the ratio of the $t^{1}\!/\!2_{\lambda z}$ following oral administration of Compound A under fed conditions to the $t^{1}\!/\!2_{\lambda z}$ following oral administration of Compound A under fasted conditions is greater than 1.2. In specific embodiments, the ratio is greater than 1.3, greater than 1.5, greater than 1.8, greater than 2.0, greater than 2.5, greater than 3.0, greater than 3.5, greater than 4.0, greater than 4.5, greater than 5.0, greater than 5.5, greater than 6.0 or greater than 6.5.

In some embodiments, the $t^{1}\!/\!2_{\lambda z}$ of Compound A is increased to at least 130 hr. In some aspects the $t^{1}\!/\!2_{\lambda z}$ of Compound A can increase to a range of from 100 hr to about 500 hr, e.g., from about 110 hr to about 500 hr, from about 120 hr to about 500 hr, from about 130 hr to about 500 hr, from about 130 hr to about 490 hr, from about 130 hr to about 480 hr, from about 130 hr to about 470 hr, from about 130 hr to about 460 hr, from about 130 hr to about 450 hr, from about 130 hr to about 440 hr, from about 130 hr to about 430 hr, from about 130 hr to about 420 hr, from about 130 hr to about 410 hr, from about 130 hr to about 400 hr, from about 130 hr to about 390 hr, from about 130 hr to about 380 hr, from about 130 hr to about 370 hr, from about 130 hr to about 360 hr, from about 130 hr to about 350 hr, from about 130 hr to about 340 hr, from about 130 hr to about 330 hr, from about 130 hr to about 320 hr, from about 130 hr to about 310 hr, from about 130 hr to about 300 hr, from about 130 hr to about 290 hr, from about 130 hr to about 280 hr, from about 130 hr to about 270 hr, from about 130 hr to about 260 hr, from about 130 hr to about 250 hr, from about 130 hr to about 240 hr, from about 130 hr to about 230 hr, from about 130 hr to about 220 hr, from about 130 hr to about 210 hr, or from about 130 hr to about 200 hr, such as about 130 hr, 140 hr, 150 hr, 160 hr, 170 hr, 180 hr, 190 hr, 200 hr, 210 hr, 220 hr, 230 hr, 240 hr, 250 hr, 260 hr, 270 hr, 280 hr, 290 hr, 300 hr, 310 hr, 320 hr, 330 hr, 340 hr, 350 hr, 360 hr, 370 hr, 380 hr, 390 hr, or 400 hr.

In one embodiment, Compound A is provided in a dosage unit form suitable for oral administration. Compound A is present in the dosage unit form at a level ranging from about of 0.05 mg/kg to about 2.0 mg/kg. More specific representative levels include 0.05 mg/kg, 0.10 mg/kg, 0.20 mg/kg, 0.30 mg/kg, 0.40 mg/kg, 0.5 mg/kg, 0.6 mg/kg, 0.7 mg/kg, 0.80 mg/kg, 0.90 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg and 2.0 mg/kg. In some aspects, the method includes orally administering 0.1-1.0 mg/kg of Compound A. In some aspects, the method includes orally administering 0.2-0.5 mg/kg of Compound A.

In some embodiments, the methods and uses described herein, such as the method of or use in treating a seizure disorder in a human in need thereof according to the methods and uses described herein, is achieved by orally administering 2 to 200 mg of Compound A. For example, the method can include orally administering about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, about 110 mg, about 111 mg, about 112 mg, about 113 mg, about 114 mg, about 115 mg, about 116 mg, about 117 mg, about 118 mg, about 119 mg, about 120 mg, about 121 mg, about 122 mg, about 123 mg, about 124 mg, about 125 mg, about 126 mg, about 127 mg, about 129 mg, about 130 mg, about 131 mg, about 132 mg, about 133 mg, about 134 mg, about 135 mg, about 136 mg, about 137 mg, about 138 mg, about 139 mg, about 140 mg, about 141 mg, about 142 mg, about 143 mg, about 144 mg, about 145 mg, about 146 mg, about 147 mg, about 148 mg, about 149 mg, about 150 mg, about 151 mg, about 152 mg, about 153 mg, about 154 mg, about 155 mg, about 156 mg, about 157 mg, about 158 mg, about 159 mg, about 160 mg, about 161 mg, about 162 mg, about 163 mg, about 164 mg, about 165 mg, about 166 mg, about 167 mg, about 168 mg, about 169 mg, about 170 mg, about 171 mg, about 172 mg, about 173 mg, about 174 mg, about 175 mg, about 176 mg, about 177 mg, about 178 mg, about 179 mg, about 180 mg, about 181 mg, about 182 mg, about 183 mg, about 184 mg, about 185 mg, about 186 mg, about 187 mg, about 188 mg, about 189 mg, about 190 mg, about 191 mg, about 192 mg, about 193 mg, about 194 mg, about 195 mg, about 196 mg, about 197 mg, about 198 mg, about 199 mg, or about 200 mg. In some aspects, the oral administration includes 5 to 50 mg of Compound A. In some aspects, the oral administration includes 10, 20, or 25 mg of Compound A. In some aspects, the oral administration includes 20 mg of Compound A. In some aspects, the oral administration includes at least 20 mg of Compound A.

In some embodiments, the methods and uses described herein, such as the method of or use in treating a seizure disorder in a human in need thereof according to the methods and uses described herein, is achieved by orally administering 5 to 1000 mg of Compound A per day, such as 5 to 500 mg or 5 to 250 mg of Compound A per day. For example, the method can include orally administering about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, or about 1000 mg per day. In some aspects, the oral administration includes orally administering 10-200 mg of Compound A per day, such as 10, 15, 20, 25, 30, 35, or 40 mg to 75, 100, 125, 150, 175, or 200 mg of Compound A per day, including 20 to 150 mg per day. In some aspects, the oral administration includes 50, 75, 100, or 125 mg of Compound A per day, such as 100 mg per day.

In certain instances, the above daily doses of Compound A are orally administered as multiple doses per day, such as in two, three, four or five doses per day. For Example, a daily dose of 100 mg, maybe administered in four 25 mg doses throughout the day.

In some embodiments, the above daily doses of Compound A are orally administered as a single dose. For example, about 5, 10, 15, 20, 25, or 30 mg to about 50, 65, 75, 100, 125, or 150 mg of Compound A per day can be orally administered as a single dose, including 10-25 mg, 10-30 mg, and 10-40 mg per day as a single dose, such as 10-25 mg per day as a single dose.

In certain embodiments, the methods and uses described herein, when using the daily dosing disclosed herein, achieve a steady state for Compound A within 6 to 9 days, such as in about 1 week.

In some instances, the present disclosure provides a method of increasing serum levels of Compound A in a human in need thereof, comprising orally administering Compound A to the human under fed conditions or from between 30 minutes prior to consuming food until 2 hours after consuming food. In similar embodiments, the present disclosure provides Compound A for use in increasing serum levels of Compound A in a human in need thereof, wherein Compound A is administered to the human under fed conditions or from between 30 minutes prior to consuming food until 2 hours after consuming food.

In one embodiment of the present disclosure, administration of Compound A, such as for treating a seizure disorder, that would benefit from the opening of the Kv7.2/Kv7.3 (KCNQ2/3) potassium channel. Compound A is a Kv7.2/Kv7.3 (KCNQ2/3) opener. In certain embodiments, the present disclosure provides a method of opening of the Kv7.2/Kv7.3 (KCNQ2/3) potassium channel in a human in need thereof comprising administering an amount of Compound A. In similar embodiments, the present disclosure provides Compound A for use in opening of the Kv7.2/Kv7.3 (KCNQ2/3) potassium channel in a human in need thereof.

In some embodiments, the present disclosure provides a method of treating, ameliorating, or preventing a disease, disorder, or condition affected by modulation of at least one potassium channel selected from Kv7.2, Kv7.3, Kv7.4 (KCNQ4), and Kv7.5 (KCNQ5) in a human in need thereof, such as by opening one or more of said potassium channels, comprising orally administering Compound A to the human, optionally under fed conditions or from between 30 minutes prior to consuming food until 2 hours after consuming food. In similar embodiments, the present disclosure provides Compound A for use in treating, ameliorating, or preventing a disease, disorder, or condition affected by modulation of at least one potassium channel selected from Kv7.2, Kv7.3, Kv7.4, and Kv7.5 in a human in need thereof, such as by opening one or more of said potassium channels, wherein Compound A is orally administered to the human, optionally under fed conditions or from between 30 minutes prior to consuming food until 2 hours after consuming food. In certain embodiments, oral administration of Compound A does not open potassium channel Kv7.1 (KCNQ1). In other words, in certain instances, Compound A is selective for one or more of Kv7.2, Kv7.3, Kv7.4, and Kv7.5 over Kv7.1.

In some embodiments, the oral administration of Compound A to a human in need thereof according the methods described herein increases the resting motor threshold (RMT) or active motor threshold (AMT). In some embodiments, the increase in RMT or AMT is in proportion to plasma concentration of Compound A. In some embodiments, the oral administration of Compound A to a human in need thereof decreases corticospinal or cortical excitability as determined using transcranial magnetic stimulation (TMS).

In certain embodiments, the present disclosure provides a method of orally administering Compound A to a human exhibiting decreased RMT or AMT relative to an average human, comprising orally administering Compound A, optionally under fed conditions or from between 30 minutes prior to consuming food until 2 hours after consuming food, thereby increasing the RMT or AMT in the human exhibiting decreased RMT or AMT.

In some embodiments, the oral administration of Compound A according to the methods and uses described herein can modulate TMS-evoked electroencephalography (EEG) potentials (TEPs) and decrease cortical excitability. In some aspects, at certain plasma concentrations (e.g., 50 ng/mL or higher), Compound A decreases the amplitude of one or more early TEP components including 15 to 35 ms (N15-P25), 45 ms (N45), or 180 ms (P180) after TMS pulse (e.g, by 50% or more) compared to placebo. In some aspects, at 2, 4, and 6 hrs post-dose, Compound A decreases the amplitude of one or more early TEP components, including 15 to 35 ms (N15-P25), 45 ms (N45), or 180 ms (P180) after TMS pulse (e.g., by 30% or more) compared to placebo.

In some embodiments, the oral administration of Compound A according to the methods and uses described herein can modulate TMS-induced oscillations and ongoing oscillatory activity. In some aspects, at certain plasma concentrations (e.g., 50 ng/mL or higher), Compound A decreases early theta (4-7 Hz) TMS-induced oscillations (30 to 390 ms) or alpha (8-12 Hz) TMS-induced oscillations (220 to 400 ms) (e.g., by 40% or more), and/or increases beta (13-30 Hz) TMS-induced power (220 to 310 ms) after TMS pulse (e.g., by 40% or more) compared to placebo. In some aspects, at 2 hrs post-dose, Compound A decreases early theta TMS-induced oscillations after TMS pulse (e.g., by 30% or more) compared to placebo. In some aspects, at 4 hrs post-dose, Compound A decreases alpha TMS-induced oscillations after TMS pulse (e.g., by 30% or more) compared to placebo. In some aspects, at 6 hrs post-dose, Compound A decreases theta TMS-induced oscillations after TMS pulse (e.g., by 30% or more) compared to placebo.

In some embodiments, the oral administration of Compound A according to the methods and uses described herein can modulate resting state EEG. In some aspects, at certain plasma concentrations (e.g., 50 ng/mL or higher), Compound A increases the power of one or more of delta, theta, or beta band (e.g., by 50% or more) compared to placebo. In some aspects, at 2, 4, and 6 hrs post-dose, Compound A increases the power of one or more delta, theta, delta, beta, or alpha band (e.g., by 40% or more) compared to placebo.

In certain embodiments, the methods and uses described herein administer Compound A in the form of a pharmaceutically acceptable oral composition that comprises Compound A and one or more pharmaceutically acceptable carriers or excipients. The amount of Compound A included in these compositions correspond to one or more of the amounts described herein. In some embodiments, the compositions are a unit dose.

Examples of pharmaceutically acceptable oral compositions that comprise Compound A include solid formulations (such as tablets, capsules, lozenges, dragées, granules, powders, multi-particulates, and films) and liquid formulations (such as aqueous solutions, elixirs, tinctures, suspensions, and dispersions). In one embodiment, a pharmaceutically acceptable oral composition of Compound A includes a pediatric suspension or granulate. All above-noted amounts of Compound A may be included in such formulations, e.g., a capsule comprising 5, 10, 15, 10, 25, 30, or 35 mg of Compound A.

In another embodiment, kits are provided for oral administration of Compound A under fed conditions to enhance the bioavailability and exposure of Compound A upon oral administration. Such kits comprise a plurality of oral dosage unit forms of Compound A in combination with instructions for orally administering of Compound A under fed conditions.

In one embodiment of the present disclosure, the oral administration of a therapeutically effective amount of Compound A results in an increase of the maximum plasma concentration ($C_{max}$) of Compound A and an increase in the exposure (AUC) of Compound A as compared to $C_{max}$ of Compound A and AUC of Compound A when orally administered under fasted conditions.

In one embodiment of the present disclosure, the ratio of the $C_{max}$ following oral administration of a therapeutically effective amount of Compound A under fed conditions to the $C_{max}$ following oral administration of a therapeutically effective amount of Compound A under fasted conditions is greater than 1.3.

In one embodiment of the present disclosure, the ratio of the AUC following oral administration of a therapeutically effective amount of Compound A under fed conditions to the AUC following oral administration of a therapeutically effective amount of Compound A under fasted conditions is greater than 1.3.

In one embodiment of the present disclosure, the therapeutically effective amount of Compound A is from about 0.05 mg/kg to about 2.0 mg/kg.

In certain embodiments herein, wherein a comparison is made involving a human orally administered Compound A under fasted conditions, an analogous comparison can be made involving a human who has not consumed food during a time period between about 4 hours prior to the oral administration of Compound A to about 4 hours after the oral administration of Compound A, such as between about 4, 3, 2, 1.5, 1, or 0.5 hours prior to the oral administration of Compound A to about 0.5, 1, 1.5, 2, 3, or 4 hours after the oral administration of Compound A.

In certain embodiments when a seizure disorder is treated herein, the seizure disorder is selected from partial onset (focal) seizures, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia. In certain embodiments, the seizure disorder is focal onset epilepsy, also known as partial onset (focal) epilepsy.

Additional embodiments and examples of the present disclosure are described herein. These embodiments and examples are illustrative and should not be construed as limiting the scope of the claimed invention.

4.3. Numbered Embodiments

Embodiment 1

A method of treating a disease, disorder, or condition associated with Kv7 potassium channel dysfunction in a human in need thereof, comprising orally administering a therapeutic amount of Compound A to the human under fed conditions; wherein Compound A is N-[4-(6-fluoro-3,4-dihydro-1H-isoquinolin-2-yl)-2,6-dimethylphenyl]-3,3-dimethylbutanamide.

Embodiment 2

A method of treating a disease, disorder, or condition associated with Kv7 potassium channel dysfunction in a human in need thereof, comprising orally administering a therapeutic amount of Compound A to the human from between 30 minutes prior to consuming food until 2 hours after consuming food; wherein Compound A is N-[4-(6-fluoro-3,4-dihydro-1H-isoquinolin-2-yl)-2,6-dimethylphenyl]-3,3-dimethylbutanamide.

Embodiment 3

The method of embodiment 1 or embodiment 2, wherein the method enhances opening of a Kv7 potassium channel.

Embodiment 4

The method of embodiment 3, wherein the Kv7 potassium channel is selected from one or more of Kv7.2, Kv7.3, Kv7.4, and Kv7.5.

Embodiment 5

The method of embodiment 4, wherein the method is selective for enhancing the opening of a Kv7 potassium channel selected from one or more of Kv7.2, Kv7.3, Kv7.4, and Kv7.5 over Kv7.1.

Embodiment 6

The method of any one of embodiments 1-5, wherein the disease, disorder, or condition is a seizure disorder.

Embodiment 7

The method of embodiment 6, wherein the seizure disorder is focal onset epilepsy.

Embodiment 8

A method of treating a seizure disorder in a human in need thereof, comprising orally administering an amount of Compound A to the human under fed conditions; wherein Compound A is N-[4-(6-fluoro-3,4-dihydro-1H-isoquinolin-2-yl)-2,6-dimethylphenyl]-3,3-dimethylbutanamide; and wherein the amount of Compound A is sufficient to treat the seizure disorder in the human.

Embodiment 9

A method of treating a seizure disorder in a human in need thereof, comprising orally administering an amount of Compound A to the human from between 30 minutes prior to consuming food until 2 hours after consuming food; wherein Compound A is N-[4-(6-fluoro-3,4-dihydro-1H-isoquinolin-2-yl)-2,6-dimethylphenyl]-3,3-dimethylbutanamide; and wherein the amount of Compound A is sufficient to treat the seizure disorder in the human.

Embodiment 10

A method of treating a seizure disorder in a human in need thereof, comprising orally administering an amount of Compound A to the human under fed conditions; wherein Compound A is N-[4-(6-fluoro-3,4-dihydro-1H-isoquinolin-2-yl)-2,6-dimethylphenyl]-3,3-dimethylbutanamide; and wherein the amount of Compound A is from 2 to 200 mg.

Embodiment 11

A method of treating a seizure disorder in a human in need thereof, comprising orally administering an amount of Compound A to the human from between 30 minutes prior to consuming food until 2 hours after consuming food; wherein Compound A is N-[4-(6-fluoro-3,4-dihydro-1H-isoquinolin-2-yl)-2,6-dimethylphenyl]-3,3-dimethylbutanamide; and wherein the amount of Compound A is from 2 to 200 mg.

Embodiment 12

In a method of treating a seizure disorder in a human in need thereof, comprising orally administering Compound A to the human, wherein Compound A is N-[4-(6-fluoro-3,4-dihydro-1H-isoquinolin-2-yl)-2,6-dimethylphenyl]-3,3-dimethylbutanamide; the improvement comprising orally administering said Compound A to said human under fed conditions.

Embodiment 13

In a method of treating a seizure disorder in a human in need thereof, comprising orally administering Compound A to the human, wherein Compound A is N-[4-(6-fluoro-3,4-dihydro-1H-isoquinolin-2-yl)-2,6-dimethylphenyl]-3,3-dimethylbutanamide; the improvement comprising orally administering said Compound A to said human from between 30 minutes prior to consuming food until 2 hours after consuming food.

Embodiment 14

In a method of orally administering Compound A to a human in need thereof, wherein Compound A is N-[4-(6-fluoro-3,4-dihydro-1H-isoquinolin-2-yl)-2,6-dimethylphenyl]-3,3-dimethylbutanamide; the improvement comprising orally administering said Compound A to said human under fed conditions.

Embodiment 15

In a method of orally administering Compound A to a human in need thereof, wherein Compound A is N-[4-(6-fluoro-3,4-dihydro-1H-isoquinolin-2-yl)-2,6-dimethylphenyl]-3,3-dimethylbutanamide; the improvement comprising orally administering said Compound A to said human from between 30 minutes prior to consuming food until 2 hours after consuming food.

Embodiment 16

The method of any one of embodiments 8-15, wherein the method increases one or more of the $C_{max}$, $AUC_{inf}$, $T_{max}$, or $t\frac{1}{2}_{\lambda z}$ of Compound A as compared to when the same amount of Compound A is orally administered to the human under fasted conditions.

Embodiment 17

A method of increasing one or more of the $C_{max}$, $AUC_{inf}$, $T_{max}$, or $t\frac{1}{2}_{\lambda z}$ of Compound A in a human receiving an oral administration of Compound A, comprising orally administering an amount of Compound A to the human under fed conditions; wherein Compound A is N-[4-(6-fluoro-3,4-dihydro-1H-isoquinolin-2-yl)-2,6-dimethylphenyl]-3,3-dimethylbutanamide; and wherein the method increases the one or more of $C_{max}$, $AUC_{inf}$, $T_{max}$, or $t\frac{1}{2}_{\lambda z}$ as compared to when the same amount of Compound A is orally administered to the human under fasted conditions.

Embodiment 18

A method of increasing one or more of the $C_{max}$, $AUC_{inf}$, $T_{max}$, or $t\frac{1}{2}_{\lambda z}$ of Compound A in a human receiving an oral administration of Compound A, comprising orally administering an amount of Compound A to the human from between 30 minutes prior to consuming food until 2 hours after consuming food; wherein Compound A is N-[4-(6-fluoro-3,4-dihydro-1H-isoquinolin-2-yl)-2,6-dimethylphenyl]-3,3-dimethylbutanamide; wherein the method increases the one or more of $C_{max}$, $AUC_{inf}$, $T_{max}$, or $t\frac{1}{2}_{\lambda z}$ as compared to when the same amount of Compound A is orally administered to the human under fasted conditions.

Embodiment 19

A method of orally administering Compound A to a human in need thereof, comprising orally administering Compound A to the human under fed conditions; wherein Compound A is N-[4-(6-fluoro-3,4-dihydro-1H-isoquinolin-2-yl)-2,6-dimethylphenyl]-3,3-dimethylbutanamide; and wherein the method increases one or more of the $C_{max}$, $AUC_{inf}$, $T_{max}$, or $t\frac{1}{2}_{\lambda z}$ of Compound A as compared to when the same amount of Compound A is orally administered to the human under fasted conditions.

Embodiment 20

A method of orally administering Compound A to a human in need thereof, comprising orally administering Compound A to the human from between 30 minutes prior to consuming food until 2 hours after consuming food; wherein Compound A is N-[4-(6-fluoro-3,4-dihydro-1H-isoquinolin-2-yl)-2,6-dimethylphenyl]-3,3-dimethylbutanamide; and wherein the method increases one or more of the $C_{max}$, $AUC_{inf}$, $T_{max}$, or $t\frac{1}{2}_{\lambda z}$ of Compound A as compared to when the same amount of Compound A is orally administered to the human under fasted conditions.

Embodiment 21

A method of reducing a dose of Compound A that is orally administered to a human in need thereof as part of a treatment regimen, comprising orally administering a reduced dose of Compound A to the human under fed conditions; wherein Compound A is N-[4-(6-fluoro-3,4-dihydro-1H-isoquinolin-2-yl)-2,6-dimethylphenyl]-3,3-dimethylbutanamide; and wherein the reduced dose is a dose lower than would be needed to achieve one or more of the same $C_{max}$, $AUC_{inf}$, $T_{max}$, or $t\frac{1}{2}_{\lambda z}$ of Compound A when orally administered to the human under fasted conditions.

Embodiment 22

A method of reducing a dose of Compound A that is orally administered to a human in need thereof as part of a treatment regimen, comprising orally administering a reduced dose of Compound A to the human from between 30 minutes prior to consuming food until 2 hours after consuming food; wherein Compound A is N-[4-(6-fluoro-3,4-dihydro-1H-isoquinolin-2-yl)-2,6-dimethylphenyl]-3,3-dimethylbutanamide; and wherein the reduced dose is a dose lower than would be needed to achieve one or more of the same $C_{max}$, $AUC_{inf}$, $T_{max}$, or $t\frac{1}{2}_{\lambda z}$ of Compound A when orally administered to the human under fasted conditions.

Embodiment 23

The method of any one of embodiments 16-22, wherein the oral administration of Compound A to the human increases the $C_{max}$ of Compound A as compared to when the same amount of Compound A is orally administered to the human under fasted conditions.

Embodiment 24

The method of embodiment 23, wherein the ratio of the $C_{max}$ following the oral administration of Compound A to the $C_{max}$ following oral administration of Compound A under fasted conditions is greater than 1.3.

Embodiment 25

The method of embodiment 23, wherein the ratio of the $C_{max}$ following the oral administration of Compound A to the $C_{max}$ following oral administration of Compound A under fasted conditions is greater than 2.

Embodiment 26

The method of embodiment 23, wherein the ratio of the $C_{max}$ following the oral administration of Compound A to the $C_{max}$ following oral administration of Compound A under fasted conditions is greater than 3.

Embodiment 27

The method of embodiment 23, wherein the increase of the $C_{max}$ of Compound A is at least 50%.

Embodiment 28

The method of embodiment 23, wherein the increase of the $C_{max}$ of Compound A is at least 100%.

Embodiment 29

The method of any one of embodiments 16-28, wherein the oral administration of Compound A to the human increases the $AUC_{inf}$ of Compound A as compared to when the same amount of Compound A is orally administered to the human under fasted conditions.

Embodiment 30

The method of embodiment 29, wherein the ratio of the $AUC_{inf}$ following the oral administration of Compound A to the $AUC_{inf}$ following oral administration of Compound A under fasted conditions is greater than 1.3.

Embodiment 31

The method of embodiment 29, wherein the ratio of the $AUC_{inf}$ following the oral administration of Compound A to the $AUC_{inf}$ following oral administration of Compound A under fasted conditions is greater than 1.5.

Embodiment 32

The method of embodiment 29, wherein the ratio of the $AUC_{inf}$ following the oral administration of Compound A to the $AUC_{inf}$ following oral administration of Compound A under fasted conditions is greater than 1.8.

Embodiment 33

The method of embodiment 29, wherein the increase of the $AUC_{inf}$ of Compound A is at least 50%.

Embodiment 34

The method of embodiment 29, wherein the increase of the $AUC_{inf}$ of Compound A is at least 75%.

Embodiment 35

The method of any one of embodiments 16-34, wherein the oral administration of Compound A to the human increases the $T_{max}$ of Compound A as compared to when the same amount of Compound A is orally administered to the human under fasted conditions.

Embodiment 36

The method of embodiment 35, wherein the ratio of the $T_{max}$ following the oral administration of Compound A to the $T_{max}$ following oral administration of Compound A under fasted conditions is greater than 1.3.

Embodiment 37

The method of embodiment 35, wherein the ratio of the $T_{max}$ following the oral administration of Compound A to the $T_{max}$ following oral administration of Compound A under fasted conditions is greater than 1.8.

Embodiment 38

The method of embodiment 35, wherein the ratio of the $T_{max}$ following the oral administration of Compound A to the $T_{max}$ following oral administration of Compound A under fasted conditions is greater than 2.

Embodiment 39

The method of embodiment 35, wherein the increase of the $T_{max}$ of Compound A is at least 50%.

Embodiment 40

The method of embodiment 35, wherein the increase of the $T_{max}$ of Compound A is at least 75%.

Embodiment 41

The method of any one of embodiments 16-40, wherein the oral administration of Compound A to the human increases the $t\frac{1}{2}_{\lambda z}$ of Compound A as compared to when the same amount of Compound A is orally administered to the human under fasted conditions.

Embodiment 42

The method of embodiment 41, wherein the ratio of the $t\frac{1}{2}_{\lambda z}$ following the oral administration of Compound A to the $t\frac{1}{2}_{\lambda z}$ following oral administration of Compound A under fasted conditions is greater than 1.2.

Embodiment 43

The method of embodiment 41, wherein the ratio of the $t\frac{1}{2}_{\lambda z}$ following the oral administration of Compound A to the $t\frac{1}{2}_{\lambda z}$ following oral administration of Compound A under fasted conditions is greater than 1.4.

Embodiment 44

The method of embodiment 41, wherein the increase of the $t\frac{1}{2}_{\lambda z}$ of Compound A is at least 20%.

Embodiment 45

The method of embodiment 41, wherein the increase of the $t\frac{1}{2}_{\lambda z}$ of Compound A is at least 35%.

Embodiment 46

A method of treating a seizure disorder in a human in need thereof, comprising orally administering Compound A to the human; wherein Compound A is N-[4-(6-fluoro-3,4-dihydro-1H-isoquinolin-2-yl)-2,6-dimethylphenyl]-3,3-dimethylbutanamide; and wherein the method produces, for Compound A, one or more of
 a $C_{max}$ of at least 40 ng/mL,
 an $AUC_{inf}$ of at least 2500 h·ng/mL,
 a $T_{max}$ of at least 3.25 hr, or
 a $t_{1/2\lambda z}$ of at least 130 h.

Embodiment 47

A method of increasing resting motor threshold (RMT) or active motor threshold (AMT) in a human in need thereof, comprising orally administering an amount of Compound A to the human; wherein Compound A is N-[4-(6-fluoro-3,4-dihydro-1H-isoquinolin-2-yl)-2,6-dimethylphenyl]-3,3-dimethylbutanamide; and wherein the amount of Compound A is sufficient to increase RMT or AMT in the human.

Embodiment 48

A method of increasing resting motor threshold (RMT) or active motor threshold (AMT) in a human in need thereof, comprising orally administering an amount of Compound A to the human; wherein Compound A is N-[4-(6-fluoro-3,4-dihydro-1H-isoquinolin-2-yl)-2,6-dimethylphenyl]-3,3-dimethylbutanamide; and wherein the amount of Compound A is 2 to 200 mg.

Embodiment 49

The method of embodiment 47 or 48, wherein the increase in RMT or AMT is in proportion to plasma concentration of Compound A.

Embodiment 50

A method of decreasing corticospinal or cortical excitability in a human in need thereof, comprising orally administering an amount of Compound A to the human; wherein Compound A is N-[4-(6-fluoro-3,4-dihydro-1H-isoquinolin-2-yl)-2,6-dimethylphenyl]-3,3-dimethylbutanamide; and wherein the amount of Compound A is sufficient to decrease corticospinal or cortical excitability in the human.

Embodiment 51

A method of decreasing corticospinal or cortical excitability in a human in need thereof, comprising orally administering an amount of Compound A to the human; wherein Compound A is N-[4-(6-fluoro-3,4-dihydro-1H-isoquinolin-2-yl)-2,6-dimethylphenyl]-3,3-dimethylbutanamide; and wherein the amount of Compound A is 2 to 200 mg.

Embodiment 52

The method of any one of embodiments 1-7, comprising orally administering 2 to 200 mg of Compound A.

Embodiment 53

The method of any one of embodiments 8-52, comprising orally administering 2 to 100 mg of Compound A.

Embodiment 54

The method of embodiment 53, comprising orally administering 5 to 50 mg of Compound A.

Embodiment 55

The method of embodiment 53, comprising orally administering 10, 20, or 25 mg of Compound A.

Embodiment 56

The method of embodiment 53, comprising orally administering 20 mg of Compound A.

Embodiment 57

The method of any one of embodiments 8-54, comprising orally administering at least 20 mg of Compound A.

Embodiment 58

The method of any one of embodiments 8-57, comprising orally administering 5-500 mg of Compound A per day.

Embodiment 59

The method of embodiment 58, comprising orally administering 20-150 mg of Compound A per day.

Embodiment 60

The method of embodiment 58, comprising orally administering 100 mg of Compound A per day.

Embodiment 61

The method of any one of embodiments 1-60, comprising orally administering 0.05-2.0 mg/kg of Compound A.

Embodiment 62

The method of embodiment 61, comprising orally administering 0.1-1.0 mg/kg of Compound A.

Embodiment 63

The method of embodiment 61, comprising orally administering 0.2-0.5 mg/kg of Compound A.

Embodiment 64

A compound for use in treating a disease, disorder, or condition associated with Kv7 potassium channel dysfunction in a human in need thereof; wherein the compound is N-[4-(6-fluoro-3,4-dihydro-1H-isoquinolin-2-yl)-2,6-dimethylphenyl]-3,3-dimethylbutanamide; wherein the compound is orally administered to the human under fed conditions.

Embodiment 65

A compound for use in treating a disease, disorder, or condition associated with Kv7 potassium channel dysfunction in a human in need thereof; wherein the compound is N-[4-(6-fluoro-3,4-dihydro-1H-isoquinolin-2-yl)-2,6-dimethylphenyl]-3,3-dimethylbutanamide; wherein the compound is orally administered to the human from between 30 minutes prior to consuming food until 2 hours after consuming food.

Embodiment 66

The compound for use of embodiment 63 or embodiment 64, wherein the method enhances opening of a Kv7 potassium channel.

Embodiment 67

The compound for use of embodiment 65, wherein the Kv7 potassium channel is selected from one or more of Kv7.2, Kv7.3, Kv7.4, and Kv7.5.

Embodiment 68

The compound for use of embodiment 66, wherein the method is selective for enhancing the opening of a Kv7 potassium channel selected from one or more of Kv7.2, Kv7.3, Kv7.4, and Kv7.5 over Kv7.1.

Embodiment 69

The compound for use of any one of embodiments 63-67, wherein the disease, disorder, or condition is a seizure disorder.

Embodiment 70

The compound for use of embodiment 68, wherein the seizure disorder is focal onset epilepsy.

Embodiment 71

A compound for use in treating a seizure disorder in a human in need thereof; wherein the compound is N-[4-(6-fluoro-3,4-dihydro-1H-isoquinolin-2-yl)-2,6-dimethylphenyl]-3,3-dimethylbutanamide; and wherein the compound is orally administered to the human under fed conditions.

Embodiment 72

A compound for use in treating a seizure disorder in a human in need thereof; wherein the compound is N-[4-(6-fluoro-3,4-dihydro-1H-isoquinolin-2-yl)-2,6-dimethylphenyl]-3,3-dimethylbutanamide; and wherein the compound is orally administered to the human from between 30 minutes prior to consuming food until 2 hours after consuming food.

Embodiment 73

The compound for use of embodiment 56 or 57, wherein orally administering the compound increases one or more of the $C_{max}$, $AUC_{inf}$, $T_{max}$, or $t\frac{1}{2}_{\lambda z}$ of the compound as compared to when the same amount of the compound is orally administered to the human under fasted conditions.

Embodiment 74

A compound for use in increasing one or more of the $C_{max}$, $AUC_{inf}$, $T_{max}$, or $t\frac{1}{2}_{\lambda z}$ of the compound in a human receiving an oral administration of the compound; wherein the compound is N-[4-(6-fluoro-3,4-dihydro-1H-isoquinolin-2-yl)-2,6-dimethylphenyl]-3,3-dimethylbutanamide; wherein the compound is orally administered to the human under fed conditions; and wherein the oral administration of the compound increases the one or more of the $C_{max}$, $AUC_{inf}$, $T_{max}$, or $t\frac{1}{2}_{\lambda z}$ as compared to when the same amount of the compound is orally administered to the human under fasted conditions.

Embodiment 75

A compound for use in increasing one or more of the $C_{max}$, $AUC_{inf}$, $T_{max}$, or $t\frac{1}{2}_{\lambda z}$ of the compound in a human receiving an oral administration of the compound; wherein the compound is N-[4-(6-fluoro-3,4-dihydro-1H-isoquinolin-2-yl)-2,6-dimethylphenyl]-3,3-dimethylbutanamide; wherein the compound is orally administered to the human from between 30 minutes prior to consuming food until 2 hours after consuming food; and wherein the oral administration of the compound increases the one or more of the $C_{max}$, $AUC_{inf}$, $T_{max}$, or $t\frac{1}{2}_{\lambda z}$ as compared to when the same amount of the compound is orally administered to the human under fasted conditions.

Embodiment 76

A compound for use in reducing a dose of the compound that is orally administered to a human in need thereof as part of a treatment regimen; wherein the compound is N-[4-(6-fluoro-3,4-dihydro-1H-isoquinolin-2-yl)-2,6-dimethylphenyl]-3,3-dimethylbutanamide; wherein a reduced dose of the compound is orally administered to the human under fed conditions; and wherein the reduced dose is a dose lower than would be needed to achieve one or more of the same $C_{max}$, $AUC_{inf}$, $T_{max}$, or $t\frac{1}{2}_{\lambda z}$ of the compound when orally administered to the human under fasted conditions.

Embodiment 77

A compound for use in reducing a dose of the compound that is orally administered to a human in need thereof as part of a treatment regimen; wherein the compound is N-[4-(6-fluoro-3,4-dihydro-1H-isoquinolin-2-yl)-2,6-dimethylphenyl]-3,3-dimethylbutanamide; wherein a reduced dose of the compound is orally administered to the human from between 30 minutes prior to consuming food until 2 hours after consuming food; and wherein the reduced dose is a dose lower than would be needed to achieve one or more of the same $C_{max}$, $AUC_{inf}$, $T_{max}$, or $t^{1/2}_{\lambda z}$ of the compound when orally administered to the human under fasted conditions.

Embodiment 78

The compound for use of any one of embodiments 73-77, wherein the oral administration of the compound to the human increases the $C_{max}$ of the compound as compared to when the same amount of the compound is orally administered to the human under fasted conditions.

Embodiment 79

The compound for use of embodiment 78, wherein the ratio of the $C_{max}$ following the oral administration of the compound to the $C_{max}$ following oral administration of the compound under fasted conditions is greater than 1.3.

Embodiment 80

The compound for use of embodiment 78, wherein the ratio of the $C_{max}$ following the oral administration of the compound to the $C_{max}$ following oral administration of the compound under fasted conditions is greater than 2.

Embodiment 81

The compound for use of embodiment 78, wherein the ratio of the $C_{max}$ following the oral administration of the compound to the $C_{max}$ following oral administration of the compound under fasted conditions is greater than 3.

Embodiment 82

The compound for use of embodiment 78, wherein the increase of the $C_{max}$ of the compound is at least 50%.

Embodiment 83

The compound for use of embodiment 78, wherein the increase of the $C_{max}$ of the compound is at least 100%.

Embodiment 84

The compound for use of any one of embodiments 73-78, wherein the oral administration of the compound to the human increases the $AUC_{inf}$ of the compound as compared to when the same amount of the compound is orally administered to the human under fasted conditions.

Embodiment 85

The compound for use of embodiment 84, wherein the ratio of the $AUC_{inf}$ following the oral administration of the compound to the $AUC_{inf}$ following oral administration of the compound under fasted conditions is greater than 1.3.

Embodiment 86

The compound for use of embodiment 84, wherein the ratio of the $AUC_{inf}$ following the oral administration of the compound to the $AUC_{inf}$ following oral administration of the compound under fasted conditions is greater than 1.5.

Embodiment 87

The compound for use of embodiment 84, wherein the ratio of the $AUC_{inf}$ following the oral administration of the compound to the $AUC_{inf}$ following oral administration of the compound under fasted conditions is greater than 1.8.

Embodiment 88

The compound for use of embodiment 84, wherein the increase of the $AUC_{inf}$ of the compound is at least 50%.

Embodiment 89

The compound for use of embodiment 84, wherein the increase of the $AUC_{inf}$ of the compound is at least 75%.

Embodiment 90

The compound for use of any one of embodiments 73-89, wherein the oral administration of the compound to the human increases the $T_{max}$ of the compound as compared to when the same amount of the compound is orally administered to the human under fasted conditions.

Embodiment 91

The compound for use of embodiment 90, wherein the ratio of the $T_{max}$ following the oral administration of the compound to the $T_{max}$ following oral administration of the compound under fasted conditions is greater than 1.3.

Embodiment 92

The compound for use of embodiment 90, wherein the ratio of the $T_{max}$ following the oral administration of the compound to the $T_{max}$ following oral administration of the compound under fasted conditions is greater than 1.8.

Embodiment 93

The compound for use of embodiment 90, wherein the ratio of the $T_{max}$ following the oral administration of the compound to the $T_{max}$ following oral administration of the compound under fasted conditions is greater than 2.

Embodiment 94

The compound for use of embodiment 75, wherein the increase of the $T_{max}$ of the compound is at least 50%.

Embodiment 95

The compound for use of embodiment 90, wherein the increase of the $T_{max}$ of the compound is at least 75%.

Embodiment 96

The compound for use of any one of embodiments 73-95, wherein the oral administration of the compound to the human increases the $t^{1/2}_{\lambda z}$ of the compound as compared to when the same amount of the compound is orally administered to the human under fasted conditions.

Embodiment 97

The compound for use of embodiment 96, wherein the ratio of the $t^{1/2}_{\lambda z}$ following the oral administration of the compound to the $t^{1/2}_{\lambda z}$ following oral administration of the compound under fasted conditions is greater than 1.2.

Embodiment 98

The compound for use of embodiment 96, wherein the ratio of the $t^{1/2}_{\lambda z}$ following the oral administration of the compound to the $t\frac{1}{2}_{\lambda z}$ following oral administration of the compound under fasted conditions is greater than 1.4.

Embodiment 99

The compound for use of embodiment 96, wherein the increase of the $t\frac{1}{2}_{\lambda z}$ of the compound is at least 20%.

Embodiment 100

The compound for use of embodiment 96, wherein the increase of the $t\frac{1}{2}_{\lambda z}$ of the compound is at least 35%.

Embodiment 101

A compound for use in treating a seizure disorder in a human in need thereof; wherein the compound is N-[4-(6-fluoro-3,4-dihydro-1H-isoquinolin-2-yl)-2,6-dimethylphenyl]-3,3-dimethylbutanamide; wherein the compound is orally administered to the human; and wherein the oral administration of the compound produces, for the compound, one or more of
a $C_{max}$ of at least 40 ng/mL,
an $AUC_{inf}$ of at least 2500 h·ng/mL,
a $T_{max}$ of at least 3.25 hr, or
a $t\frac{1}{2}_{\lambda z}$ of at least 130 h.

Embodiment 102

A compound for use in increasing resting motor threshold (RMT) or active motor threshold (AMT) in a human in need thereof; wherein the compound is N-[4-(6-fluoro-3,4-dihydro-1H-isoquinolin-2-yl)-2,6-dimethylphenyl]-3,3-dimethylbutanamide; wherein the compound is orally administered to the human.

Embodiment 103

The compound for use of embodiment 102, wherein the increase in RMT or AMT is in proportion to plasma concentration of the compound.

Embodiment 104

A compound for use in decreasing corticospinal or cortical excitability in a human in need thereof; wherein the compound is N-[4-(6-fluoro-3,4-dihydro-1H-isoquinolin-2-yl)-2,6-dimethylphenyl]-3,3-dimethylbutanamide; wherein the compound is orally administered to the human.

Embodiment 105

The compound for use of any one of embodiments 64-89, wherein 2 to 200 mg of the compound is administered.

Embodiment 106

The compound for use of embodiment 105, wherein 2 to 100 mg of the compound is administered.

Embodiment 107

The compound for use of embodiment 105, wherein 5 to 50 mg of the compound is administered.

Embodiment 108

The compound for use of embodiment 105, wherein 10, 20, or 25 mg of the compound is administered.

Embodiment 109

The compound for use of embodiment 105, wherein 20 mg of the compound is administered.

Embodiment 110

The compound for use of any one of embodiments 64-107, wherein at least 20 mg of the compound is administered.

Embodiment 111

The compound for use of any one of embodiments 64-110, wherein 5-500 mg of the compound is administered per day.

Embodiment 112

The compound for use of embodiment 111, wherein 20-150 mg of the compound is administered per day.

Embodiment 113

The compound for use of embodiment 111, wherein 100 mg of the compound is administered per day.

Embodiment 114

The compound for use of any one of embodiments 64-113, wherein 0.05-2.0 mg/kg of the compound is administered.

Embodiment 115

The compound for use of embodiment 114, wherein 0.1-1.0 mg/kg of the compound is administered.

Embodiment 116

The compound for use of embodiment 114, wherein 0.2-0.5 mg/kg of the compound is administered.

4.4. Additional Numbered Embodiments

Embodiment 1a

A method of treating a seizure disorder in a human, wherein the method comprises orally administering a therapeutically effective amount of Compound A to the human in need thereof under fed conditions.

Embodiment 2a

The method of embodiment 1a wherein the oral administration of a therapeutically effective amount of Compound A to the human results in an enhancement of the bioavailability and exposure of Compound A, as compared to the bioavailability and exposure of Compound A when orally administered under fasted conditions.

Embodiment 3a

The method of embodiment 2a wherein the oral administration of a therapeutically effective amount of Compound A results in an increase of the maximum plasma concentration ($C_{max}$) of Compound A and an increase in the exposure (AUC) of Compound A, as compared to the $C_{max}$ of Compound A and the AUC of Compound A when orally administered under fasted conditions.

Embodiment 4a

The method of embodiment 3a wherein the ratio of the $C_{max}$ following oral administration of a therapeutically effective amount of Compound A under fed conditions to the $C_{max}$ following oral administration of a therapeutically effective amount of Compound A under fasted conditions is greater than 1.3.

Embodiment 5a

The method of embodiment 3a wherein the ratio of the AUC following oral administration of a therapeutically effective amount of Compound A under fed conditions to the AUC following oral administration of a therapeutically effective amount of Compound A under fasted conditions is greater than 1.3.

Embodiment 6a

The method of any one of embodiments 1a-5a wherein the therapeutically effective amount of Compound A is from about 0.05 mg/kg to about 2.0 mg/kg.

Embodiment 7a

A method of enhancing the bioavailability and exposure of Compound A in a human receiving an oral administration of a therapeutically effective amount of Compound A for the treatment of a seizure disorder, wherein the method comprises orally administering the therapeutically effective amount of Compound A to the human under fed conditions.

Embodiment 8a

The method of embodiment 7a wherein the oral administration of a therapeutically effective amount of Compound A results in an increase of the maximum plasma concentration ($C_{max}$) of Compound A and an increase in the exposure (AUC) of Compound A, as compared to $C_{max}$ of Compound A and AUC of Compound A when orally administered under fasted conditions.

Embodiment 9a

The method of embodiment 8a wherein the ratio of the $C_{max}$ following oral administration of a therapeutically effective amount of Compound A under fed conditions to the $C_{max}$ following oral administration of a therapeutically effective amount of Compound A under fasted conditions is greater than 1.3.

Embodiment 10a

The method of embodiment 8a wherein the ratio of the AUC following oral administration of a therapeutically effective amount of Compound A under fed conditions to the AUC following oral administration of a therapeutically effective amount of Compound A under fasted conditions is greater than 1.3.

Embodiment 11a

The method of any one of embodiments 7a-10a wherein the therapeutically effective amount of Compound A is from about 0.05 mg/kg to about 2.0 mg/kg.

5. EXAMPLES

The following studies were conducted to determine the food effect, if any, on the bioavailability and exposure of Compound A when Compound A is orally administered. Further studies were conducted to access the effect Compound A exhibited, if any, on cortical excitability using transcranial magnetic stimulation (TMS).

5.1. Example 1. Non-Human Primate Study

The following study was conducted to determine the effect of food when Compound A is orally administered to a non-human primate.

5.1.1. Study Animals

Three (n=3) Cynomolgus monkeys of Vietnamese origin were used in this study. At the time of initial dose administration, the monkeys weighed 4.7 to 5.1 kg and were about 4.5 years of age.

A certified primate diet (Teklad® Certified Diet 2050C) was fed during the study. For Group 1, the three monkeys were fasted overnight with food returned 4 hours post-dose. For Group 2, the same three monkeys were fasted overnight and offered food about 1 hour prior to dosing and food was returned at 4 hours post-dose. The following Table 1 gives the food consumption for Group 2:

TABLE 1

| Group 2 Food Consumption | | | |
| --- | --- | --- | --- |
| Group 2 | Animal #1 | Animal #2 | Animal #3 |
| Time food offered[1] | 8;19 | 8;19 | 8;19 |
| Biscuits offered | 7 | 7 | 7 |
| Biscuits remaining? | 7 | 7 | 4 |
| Banana Remaining? (Y/N) | N | N | N |
| Bread remaining? (Y/N) | Partial | N | N |
| Time food consumption recorded | 9.07 | 9.07 | 9.07 |
| Time dosed | 9.34 | 9.37 | 9.39 |

[1]All animals were fasted the evening prior to dosing. Approximately 1 hour prior to dosing, the animals were offered ½ banana, slice of bread and ½ daily ration of biscuits. Food consumption was recorded. Food was returned following the 4 hours post dose collections.

5.1.2. Oral Dosage Units

The oral dosage units consisted of about 3 mg/kg of Compound A in a capsule. The capsules were filled the morning of the dose administration and kept at room temperature until dosing. The remaining capsules were placed into the −20° C. storage.

5.1.3. Administration of Oral Dosage Units

The capsules were placed as far back in the animal's mouth as possible using a pill gun or a modified gavage tube. Approximately 10 mL of water was administered via syringe to ensure complete delivery of the intended dose. Each animal received 1 capsule per dose. The same animals were dosed twice with a 96 hour washout period between doses. See Table 2 below for details.

Group 1: All animals were weighed the afternoon prior to dose administration. Animal #2 struggled with dosing. After several attempts, the animal was given a short break and finally dosed successfully.

Group 2: All animals were weighed the morning of dose administration. All animals were dosed without incident.

TABLE 2

Oral Dosage Units

| Group # | Animal # | Animal weight (kg) | Dose Administered (mg) | Dosage Unit (mg/kg) |
|---|---|---|---|---|
| 1 | 1 | 4.695 | 14.30 | 3.05 |
| 1 | 2 | 5.116 | 15.40 | 3.01 |
| 1 | 3 | 5.217 | 16.40 | 3.14 |
| 2 | 1 | 4.698 | 14.30 | 3.04 |
| 2 | 2 | 5.057 | 15.40 | 3.05 |
| 2 | 3 | 5.133 | 15.30 | 2.98 |

5.1.4. Collection of Blood

Whole blood (~2.0 mL) was collected using syringe and needle from cephalic or saphenous veins and transferred into vacutainer tubes containing $K_2EDTA$ and kept on wet ice until processed for plasma. Blood samples were collected at time of dosing (0.0 hours, time zero) and at 0.5, 1, 2, 4, 8, 12, 24 and 48 hours post-dose.

5.1.5. Blood Sample Processing

The whole blood samples were placed in a $K_2EDTA$ tube and centrifuged at 3200 RPM for 10 minutes at approximately 5° C. Plasma samples were divided into 2 aliquots and each aliquot directly transferred to appropriately labeled, individual tubes containing study number, collection time point, animal ID number, and sample description. One aliquot was placed into storage at −20±5° C. until shipment for analysis. The other aliquot was retained at −20±5° C. Red blood cells were disposed.

All samples were processed per standard protocol for bioanalytical analysis.

5.1.6. Results

TABLE 3

Concentrations of Compound A in the Plasma of Fasted Male Cynomolgus Monkeys Following Oral Administration of a Unit Dose of 3 mg/kg of Compound A

| Group | Animal # | Time (h) | Concentration (ng/mL) |
|---|---|---|---|
| 1 | 1 | 0 | 0 |
|  |  | 0.5 | 0 |
|  |  | 1 | 0 |
|  |  | 2 | 6.00 |
|  |  | 4 | 12.6 |
|  |  | 8 | 38.4 |
|  |  | 12 | 38.3 |
|  |  | 24 | 22.5 |
|  |  | 48 | 3.13 |
|  | 2 | 0 | 0 |
|  |  | 0.5 | 0 |
|  |  | 1 | 15.6 |
|  |  | 2 | 23.5 |
|  |  | 4 | 19.2 |
|  |  | 8 | 63.1 |
|  |  | 12 | 75.1 |
|  |  | 24 | 53.2 |
|  |  | 48 | 12.5 |
|  | 3 | 0 | 0 |
|  |  | 0.5 | 0 |
|  |  | 1 | 5.07 |
|  |  | 2 | 16.4 |
|  |  | 4 | 18.1 |
|  |  | 8 | 48.1 |
|  |  | 12 | 53.7 |
|  |  | 24 | 51.8 |
|  |  | 48 | 11.2 |

TABLE 4

Concentrations of Compound A in the Plasma of Fed Male Cynomolgus Monkeys Following Capsule Administration at 3 mg/kg

| Group | Animal # | Time (h) | Concentration (ng/mL) |
|---|---|---|---|
| 1 | 1 | 0 | 0 |
|  |  | 0.5 | 0 |
|  |  | 1 | 1.48 |
|  |  | 2 | 11.8 |
|  |  | 4 | 34.8 |
|  |  | 8 | 50.4 |
|  |  | 12 | 48.8 |
|  |  | 24 | 24.2 |
|  |  | 48 | 4.26 |
|  | 2 | 0 | 0 |
|  |  | 0.5 | 1.05 |
|  |  | 1 | 1.05 |
|  |  | 2 | 0 |
|  |  | 4 | 19.9 |
|  |  | 8 | 52.2 |
|  |  | 12 | 67.5 |
|  |  | 24 | 61.9 |
|  |  | 48 | 16.9 |
|  | 3 | 0 | 0 |
|  |  | 0.5 | 0 |
|  |  | 1 | 1.21 |
|  |  | 2 | 11.4 |
|  |  | 4 | 78.2 |
|  |  | 8 | 63.7 |
|  |  | 12 | 42.2 |
|  |  | 24 | 48.8 |
|  |  | 48 | 13.5 |

TABLE 5

Summary of Pharmacokinetic Parameters for Compound A in the Plasma of Fasted versus Fed Male Cynomolgus Monkeys Following Capsule Administration at 3 mg/kg

| Group | Time (h) | Mean (ng/mL) | SD (ng/mL) | N |
|---|---|---|---|---|
| 1 | 0 | 0 | 0 | 3 |
|  | 0.5 | 0 | 0 | 3 |
|  | 1 | 6.89 | 7.96 | 3 |
|  | 2 | 15.3 | 8.8 | 3 |
|  | 4 | 16.6 | 3.54 | 3 |
|  | 8 | 49.9 | 12.4 | 3 |
|  | 12 | 55.7 | 18.5 | 3 |
|  | 24 | 42.5 | 17.3 | 3 |
|  | 48 | 8.94 | 5.08 | 3 |
| 2 | 0 | 0 | 0 | 3 |
|  | 0.5 | 0.35 | 0.61 | 3 |
|  | 1 | 1.25 | 0.22 | 3 |
|  | 2 | 7.73 | 6.7 | 3 |
|  | 4 | 44.3 | 30.3 | 3 |
|  | 8 | 55.4 | 7.22 | 3 |
|  | 12 | 52.8 | 13.1 | 3 |
|  | 24 | 45 | 19.1 | 3 |
|  | 48 | 11.6 | 6.54 | 3 |

TABLE 6

Summary of Pharmacokinetic Parameters for Compound A in the Plasma of Fasted vs Fed Male Cynomolgus Monkeys Following Capsule Administration at 3 mg/kg

| Group | Subject | $t_{1/2 \lambda z}$ (h) | $T_{max}$ (h) | $C_{max}$ (ng/mL) | $AUC_{last}$ (h × ng/mL) | $AUC_{infobs}$ (h × ng/mL) |
|---|---|---|---|---|---|---|
| 1 | 1 | 9.7 | 8 | 38.4 | 869 | 913 |
|  | 2 | — | 12 | 75.1 | 1940 | — |
|  | 3 | — | 12 | 53.7 | 1650 | — |

TABLE 6-continued

Summary of Pharmacokinetic Parameters for Compound A
in the Plasma of Fasted vs Fed Male Cynomolgus Monkeys
Following Capsule Administration at 3 mg/kg

| Group | Subject | $t_{1/2\lambda z}$ (h) | $T_{max}$ (h) | $C_{max}$ (ng/mL) | $AUC_{last}$ (h × ng/mL) | $AUC_{infobs}$ (h × ng/mL) |
|---|---|---|---|---|---|---|
| | Mean | 9.7 | 10.7 | 55.7 | 1490 | 913 |
| | SD | — | 2.3 | 18.4 | 556 | — |
| 2 | 1 | 10.1 | 8 | 50.4 | 1120 | 1180 |
| | 2 | — | 12 | 67.5 | 2010 | — |
| | 3 | — | 4 | 78.2 | 1790 | — |
| | Mean | 10.1 | 8 | 65.4 | 1640 | 1180 |
| | SD | — | 4 | 14 | 466 | — |

5.1.7. Discussion

Figure 1:
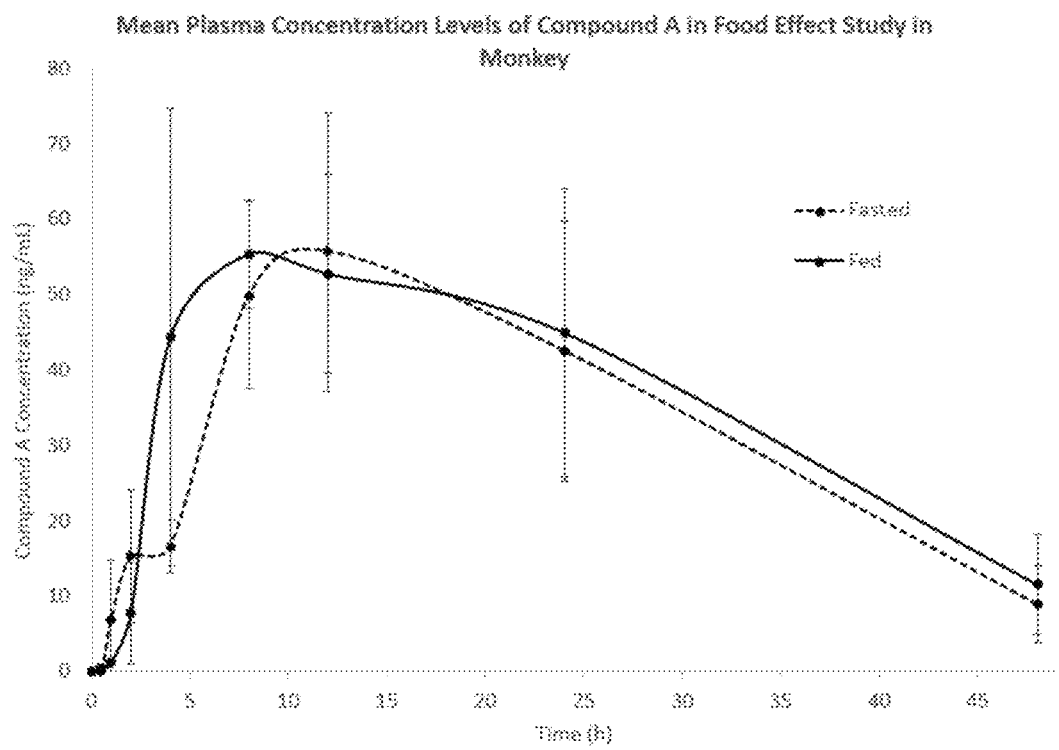
FIG. 1 illustrates the mean plasma concentration levels of Compound A in a food effect study in cynomolgus monkeys, as described below in Table 5 of Example 1, showing Compound A concentration (ng/mL) (y-axis) over time (hours) (x-axis).

No significant food effect on either the $C_{max}$ or the AUC of Compound A was observed in this study when Compound A was orally administered to a non-human primate. FIG. 1 shows the data in Table 5 in graphical form.

5.2. Example 2. Human Study

To evaluate the effects of food on the bioavailability and exposure of Compound A, an open-label, randomized, two-period, fed/fasted crossover study was carried out with nine healthy, adult, non-tobacco using male and female (non-childbearing potential only) human subjects, aged ≥18 to ≤55 years.

The study consisted of two Treatment Periods, Period 1 and Period 2. Each Treatment Period consisted of 7 days, with the dosing of Compound A occurring on Day 1. The two treatment periods were separated by a washout period of 10 days. The subjects were randomized into two groups. During Treatment Period 1, one group received an oral dose of Compound A while fasted and the other group received an oral dose of Compound A when fed. The group which fasted in Treatment Period 1 was fed in Treatment Period 2 and vice versa.

On Day 1 of each Treatment Period, each subject orally received 20 mg of Compound A (4 capsules with 5 mg of Compound A in each capsule).

During the fed period, following an overnight fast of at least 10 hours, a standard high fat, high calorie breakfast was given as per FDA guidance; the breakfast was given 30 minutes prior to the scheduled dosing time, and was completed 10 minutes before dosing. A representative breakfast included 2 slices of buttered toast, 2 fried eggs, 2 strips of bacon, 4 oz. of hash brown potatoes, and 8 oz. of whole milk. Subjects did not eat for at least 4 hours following dosing.

During the fasted period, dosing occurred after an overnight fast of at least 10 hours. No food was allowed for 4 hours post-dose in either the fed or fasted period. Water was allowed as desired except for one hour before and after dosing.

For all subjects, blood samples for the determination of Compound A plasma concentration were collected at dosing (0.0 hours (time zero)) and at 0.5, 1.0, 1.5, 2.0, 3.0, 4.0, 6.0, 8.0, 12.0, 24.0, 32.0, 48.0 and 144.0 hours post-dose.

5.2.1. Results

The plasma concentrations (ng/mL) of Compound A in the subjects receiving the oral dose of Compound A under fed conditions is shown below in Table 7.

The plasma concentrations (ng/mL) of Compound A in the subjects receiving the oral dose of Compound A under fasted conditions is shown below in Table 8.

Figure 2:
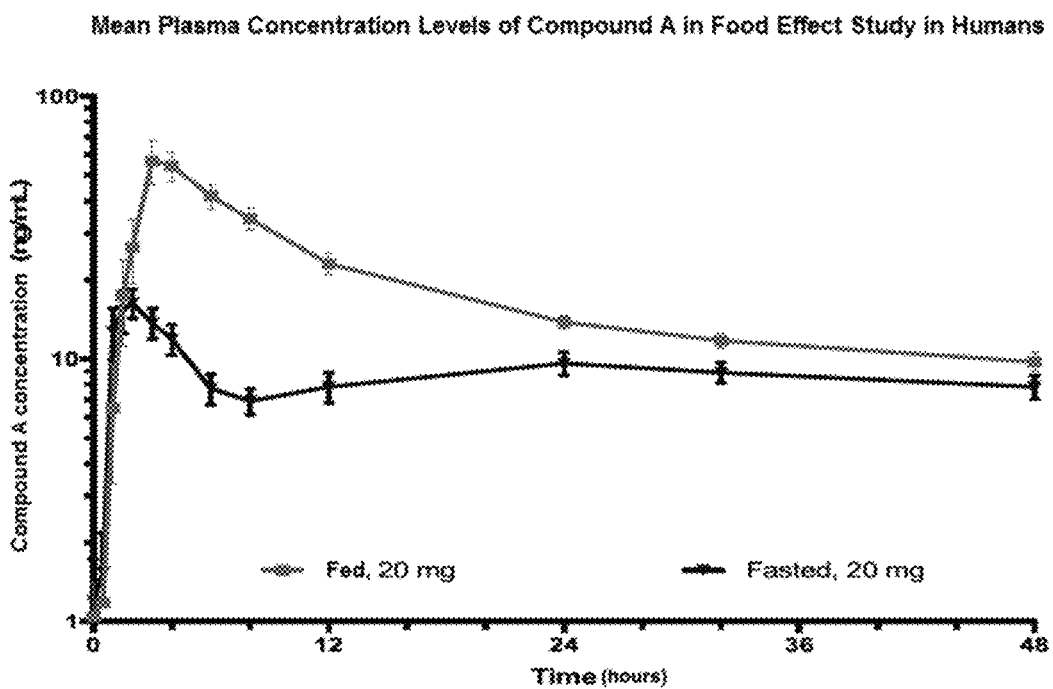
FIG. 2 illustrates the mean plasma concentration levels of Compound A in a food effect study in humans, as described below in Example 2, showing Compound A concentration (ng/mL) (y-axis) over time (hours) (x-axis).

The mean plasma concentrations (ng/mL) of Compound A in the subjects receiving the oral dose of Compound A under fed conditions versus the mean plasma concentrations (ng/mL) of Compound A in the subjects receiving the oral dose of Compound A under fasted conditions are illustrated in FIG. 2.

The pharmacokinetic parameters of subjects orally receiving 20 mg of Compound A under fed conditions are shown below in Table 9.

The pharmacokinetic parameters of subjects orally receiving 20 mg of Compound A under fasted conditions are shown below in Table 10.

TABLE 7

Blood Concentration of Subjects Orally Receiving 20 mg of Compound A under Fed Conditions

| Subject No. | Treatment Period | Condition | 0.00 | 0.50 | 1.0 | 1.5 | 2.0 | 3.0 | 4.0 | 6.0 | 8.0 | 12.0 | 24.0 | 32.0 | 48.0 | 144.0 |
|---|---|---|---|---|---|---|---|---|---|---|---|---|---|---|---|---|
| | | | | | | | Compound A Concentration (ng/mL) | | | | | | | | | |
| 1 | 1 | fed | 0.00 | 0.00 | 1.07 | 6.07 | 23.8 | 57.5 | 60.0 | 31.0 | 22.3 | 14.7 | 11.9 | 11.6 | 8.76 | 5.06 |
| 2 | 2 | fed | 1.28 | 1.16 | 4.66 | 11.7 | 23.7 | 70.6 | 77.5 | 63.6 | 41.9 | 24.5 | 12.5 | 10.6 | 7.89 | 3.68 |
| 3 | 2 | fed | 1.71 | 1.56 | 4.59 | 18.7 | 37.2 | 66.1 | 59.7 | 46.3 | 25.6 | 15.6 | 13.5 | 11.3 | 9.54 | 6.15 |
| 4 | 2 | fed | 2.92 | 2.56 | 2.74 | 4.34 | 5.63 | 12.1 | 39.2 | 38.1 | 52.0 | 35.6 | 15.8 | 12.6 | 12.3 | 8.82 |
| 5 | 1 | fed | 0.00 | 0.00 | 7.27 | 22.3 | 24.6 | 58.5 | 52.7 | 44.6 | 33.1 | 24.6 | 14.5 | 10.9 | 8.44 | 3.99 |
| 6 | 2 | fed | 2.05 | 4.06 | 30.6 | 58.3 | 57.7 | 104 | 81.0 | 56.7 | 36.5 | 23.0 | 17.4 | 15.6 | 13.6 | 7.91 |
| 7 | 1 | fed | 0.00 | 0.00 | 0.00 | 0.00 | 3.94 | 46.1 | 39.2 | 33.3 | 22.1 | 17.7 | 10.5 | 8.60 | 6.77 | 5.33 |
| 8 | 2 | fed | 1.43 | 1.30 | 1.62 | 1.91 | 2.90 | 7.50 | 14.7 | 16.4 | 39.2 | 24.0 | 11.4 | 10.0 | 8.03 | 5.56 |
| 9 | 1 | fed | 0.00 | 0.00 | 5.89 | 33.3 | 60.6 | 90.3 | 66.7 | 46.4 | 35.3 | 28.0 | 16.9 | 14.6 | 12.5 | 6.89 |
| Number of subjects | | | 9 | 9 | 9 | 9 | 9 | 9 | 9 | 9 | 9 | 9 | 9 | 9 | 9 | 9 |
| Mean | | | 1.04 | 1.18 | 6.49 | 17.4 | 26.7 | 57.0 | 54.5 | 41.8 | 34.2 | 23.1 | 13.8 | 11.8 | 9.76 | 5.93 |
| Standard Deviation | | | 1.09 | 1.41 | 9.34 | 18.8 | 21.7 | 32.0 | 20.9 | 14.1 | 9.82 | 6.53 | 2.48 | 2.21 | 2.42 | 1.71 |
| Standard Error | | | 0.36 | 0.47 | 3.11 | 6.26 | 7.24 | 10.7 | 6.97 | 4.71 | 3.27 | 2.18 | 0.83 | 0.74 | 0.81 | 0.57 |
| Minimum | | | 0.00 | 0.00 | 0.00 | 0.00 | 2.90 | 7.50 | 14.7 | 16.4 | 22.1 | 14.7 | 10.5 | 8.60 | 6.77 | 3.68 |
| Median | | | 1.28 | 1.16 | 4.59 | 11.7 | 23.8 | 58.5 | 59.7 | 44.6 | 35.3 | 24.0 | 13.5 | 11.3 | 8.76 | 5.56 |
| Maximum | | | 2.92 | 4.06 | 30.6 | 58.3 | 60.6 | 104 | 81.0 | 63.6 | 52.0 | 35.6 | 17.4 | 15.6 | 13.6 | 8.82 |
| Geometric Mean | | | | | | | 17.0 | 44.0 | 49.5 | 39.3 | 33.0 | 22.3 | 13.6 | 11.6 | 9.50 | 5.72 |
| CV % Geometric Mean | | | | | | | 166 | 113 | 56.1 | 41.7 | 29.9 | 29.1 | 18.1 | 18.6 | 24.6 | 29.7 |

TABLE 8

Blood Concentration of Subjects Orally Receiving 20 mg of Compound A under Fasted Conditions

| Subject No. | Treatment Period | Condition | 0.00 | 0.50 | 1.00 | 1.50 | 2.00 | 3.00 | 4.00 | 6.00 | 8.00 | 12.0 | 24.0 | 32.0 | 48.0 | 144 |
|---|---|---|---|---|---|---|---|---|---|---|---|---|---|---|---|---|
| | | | \multicolumn{14}{c}{Compound A Concentration (ng/mL)} | | | | | | | | | |
| 1 | 2 | fasted | 2.05 | 4.02 | 10.1 | 14.5 | 13.8 | 9.72 | 8.27 | 6.15 | 5.75 | 7.65 | 11.7 | 9.37 | 8.66 | 4.24 |
| 2 | 1 | fasted | 0.00 | 0.00 | 10.7 | 12.7 | 11.7 | 8.61 | 8.03 | 5.08 | 6.08 | 9.05 | 8.87 | 10.8 | 6.42 | 1.95 |
| 3 | 1 | fasted | 0.00 | 0.00 | 4.66 | 9.21 | 10.9 | 10.6 | 6.93 | 3.75 | 3.62 | 4.28 | 4.28 | 5.67 | 4.74 | 2.64 |
| 4 | 1 | fasted | 0.00 | 0.00 | 33.3 | 37.1 | 29.8 | 21.4 | 15.6 | 10.2 | 8.32 | 8.62 | 9.53 | 7.60 | 7.14 | 4.21 |
| 5 | 2 | fasted | 1.82 | 2.47 | 17.4 | 11.6 | 13.9 | 11.1 | 10.5 | 8.59 | 8.97 | 8.78 | 9.83 | 8.81 | 8.19 | 3.09 |
| 6 | 1 | fasted | 0.00 | 0.00 | 12.3 | 15.7 | 19.8 | 22.4 | 17.6 | 9.46 | 7.26 | 6.25 | 11.2 | 9.30 | 8.80 | 3.16 |
| 7 | 2 | fasted | 4.45 | 4.48 | 10.3 | 15.6 | 16.2 | 16.0 | 15.4 | 9.35 | 8.65 | 10.1 | 12.3 | 12.0 | 10.1 | — |
| 8 | 1 | fasted | 0.00 | 0.00 | 8.24 | 9.62 | 10.2 | 8.21 | 7.10 | 4.16 | 3.71 | 2.71 | 6.09 | 5.09 | 4.42 | 2.06 |
| 9 | 2 | fasted | 2.44 | 2.96 | 7.62 | 11.9 | 21.1 | 15.8 | 18.0 | 12.7 | 9.97 | 13.2 | 13.0 | 11.3 | 12.1 | 5.91 |
| Number of subjects | | | 9 | 9 | 9 | 9 | 9 | 9 | 9 | 9 | 9 | 9 | 9 | 9 | 9 | 8 |
| Mean | | | 1.20 | 1.55 | 12.7 | 15.3 | 16.4 | 13.8 | 11.9 | 7.72 | 6.93 | 7.85 | 9.64 | 8.88 | 7.84 | 3.41 |
| Standard Deviation | | | 1.60 | 1.92 | 8.47 | 8.50 | 6.30 | 5.40 | 4.66 | 3.07 | 2.29 | 3.13 | 2.89 | 2.40 | 2.47 | 1.33 |
| Standard Error | | | 0.532 | 0.640 | 2.82 | 2.83 | 2.10 | 1.80 | 1.55 | 1.02 | 0.762 | 1.04 | 0.965 | 0.799 | 0.823 | 0.468 |
| Minimum | | | 0.00 | 0.00 | 4.66 | 9.21 | 10.2 | 8.21 | 6.93 | 3.75 | 3.62 | 2.71 | 4.28 | 5.09 | 4.42 | 1.95 |
| Median | | | 0.00 | 0.00 | 10.3 | 12.7 | 13.9 | 11.1 | 10.5 | 8.59 | 7.26 | 8.62 | 9.83 | 9.30 | 8.19 | 3.13 |
| Maximum | | | 4.45 | 4.48 | 33.3 | 37.1 | 29.8 | 22.4 | 18.0 | 12.7 | 9.97 | 13.2 | 13.0 | 12.0 | 12.1 | 5.91 |
| Geometric Mean | | | | | 11.0 | 14.0 | 15.5 | 12.9 | 11.1 | 7.14 | 6.54 | 7.18 | 9.16 | 8.56 | 7.48 | 3.20 |
| CV % Geometric Mean | | | | | 59.4 | 43.1 | 36.3 | 39.4 | 41.7 | 45.2 | 38.7 | 51.1 | 37.7 | 30.6 | 34.3 | 39.4 |

TABLE 9

Pharmacokinetic Parameters of Subjects Orally Receiving 20 mg of Compound A under Fed Conditions

| Subject # | Treatment Period | Condition | $T_{Max}$ (h) | $C_{max}$ (ng/mL) | $AUC_{last}$ (h × ng/mL) | $AUC_{inf}$ (h × ng/mL) | % $AUC_{ext}$ (%) | $t^{1/2}_{\lambda z}$ (h) |
|---|---|---|---|---|---|---|---|---|
| fed | 1 | fed | 4.00 | 60.0 | 1410 | 2130 | 33.9 | 98.7 |
| | 2 | fed | 4.00 | 77.5 | 1530 | 1950 | 21.2 | 77.7 |
| | 2 | fed | 3.00 | 66.1 | 1590 | 2790 | 43.0 | 135 |
| | 2 | fed | 8.00 | 52.0 | 2020 | 4710 | 57.1 | 211 |
| | 1 | fed | 3.00 | 58.5 | 1500 | 1960 | 23.7 | 80.9 |
| | 2 | fed | 3.00 | 104 | 2230 | 3560 | 37.5 | 117 |
| | 1 | fed | 3.00 | 46.1 | 1230 | 2690 | 54.3 | 190 |
| | 2 | fed | 8.00 | 39.2 | 1330 | 2500 | 46.9 | 146 |
| | 1 | fed | 3.00 | 90.3 | 2050 | 3110 | 33.9 | 106 |
| Mean | | | 4.33 | 66.0 | 1650 | 2820 | 39.1 | 129 |
| Standard Error | | | 0.707 | 7.04 | 119 | 296 | 4.16 | 15.5 |
| Minimum | | | 3.00 | 39.2 | 1230 | 1950 | 21.2 | 77.7 |
| Median | | | 3.00 | 60.0 | 1530 | 2690 | 37.5 | 117 |
| Maximum | | | 8.00 | 104 | 2230 | 4710 | 57.1 | 211 |
| Geometric Mean | | | 3.98 | 63.1 | 1620 | 2710 | 37.2 | 122 |

TABLE 10

Pharmacokinetic Parameters of Subjects Orally Receiving 20 mg of Compound A under Fasted Conditions

| Subject # | Treatment Period | Condition | $T_{max}$ (h) | $C_{max}$ (ng/mL) | $AUC_{last}$ (ng × h/mL) | $AUC_{inf}$ (ng × h/mL) | % $AUC_{ext}$ (%) | $t^{1/2}_{\lambda z}$ (h) |
|---|---|---|---|---|---|---|---|---|
| 1 | 2 | fasted | 1.50 | 14.5 | 1060 | 1640 | 35.8 | 96.2 |
| 2 | 1 | fasted | 1.50 | 12.7 | 816 | 960 | 15.0 | 51.1 |
| 3 | 1 | fasted | 2.00 | 10.9 | 593 | 995 | 40.4 | 105 |
| 4 | 1 | fasted | 1.50 | 37.1 | 1010 | 1800 | 43.7 | 129 |
| 5 | 2 | fasted | 1.00 | 17.4 | 979 | 1300 | 24.7 | 72.1 |
| 6 | 1 | fasted | 3.00 | 22.4 | 1040 | 1350 | 22.9 | 67.7 |
| 7 | 2 | fasted | 2.00 | 16.2 | 541 | 1720 | 68.5 | 80.8 |
| 8 | 1 | fasted | 2.00 | 10.2 | 547 | 803 | 31.9 | 86.3 |
| 9 | 2 | fasted | 2.00 | 21.1 | 1460 | 2410 | 39.5 | 111 |

TABLE 10-continued

Pharmacokinetic Parameters of Subjects Orally Receiving 20 mg of Compound A under Fasted Conditions

| Subject # | Treatment Period | Condition | $T_{max}$ (h) | $C_{max}$ (ng/mL) | $AUC_{last}$ (ng × h/mL) | $AUC_{inf}$ (ng × h/mL) | % $AUC_{ext}$ (%) | $t^{1/2}{}_{\lambda z}$ (h) |
|---|---|---|---|---|---|---|---|---|
| | Mean | | 1.83 | 18.1 | 894 | 1440 | 35.8 | 89.0 |
| | Standard Error | | 0.10 | 2.76 | 101 | 169 | 5.14 | 8.09 |
| | Minimum | | 1.00 | 10.2 | 541 | 803 | 15.0 | 51.1 |
| | Median | | 2.00 | 16.2 | 979 | 1350 | 35.8 | 86.3 |
| | Maximum | | 3.00 | 37.1 | 1460 | 2410 | 68.5 | 129 |
| | Geometric Mean | | 1.76 | 16.7 | 848 | 1370 | 33.0 | 85.9 |

As the pharmacokinetic results of this study demonstrated, the bioavailability and exposure of Compound A were significantly enhanced when orally administered under fed conditions as compared to the bioavailability and exposure of Compound A when orally administered under fasted conditions. These results were unexpected in view of the results of the non-human primate study as set forth above in Example 1 where no food effect was observed.

5.3. Example 3. Human SAD and MAD Study

A first-in-human study was conducted to evaluate the safety, tolerability and pharmacokinetics (PK) of single and multiple ascending doses (SAD and MAD) of oral Compound A.

5.3.1. Methods

In the SAD Phase, 32 healthy volunteers were randomized (3:1) to Compound A (5, 15, 20, 25 or 30 mg) or placebo. The study featured an adaptive design. A crossover food effect cohort (N=10) was also completed with single doses of 20 mg. A sub-set of 8 male subjects were also assessed with Transcranial Magnetic Stimulation (TMS) for effects on cortical excitability (see Examples 4 and 5).

Repeat doses of Compound A (15 mg QD) were evaluated in a fasted and fed state over 7 and 10 days, respectively. Repeat doses of Compound A (25 mg QD) were also evaluated in a fed state over 10 days.

Compound A was formulated as an immediate release capsule. Serial plasma PK samples were collected for all cohorts. Safety evaluations throughout the study included adverse event (AE) monitoring, clinical laboratory tests, vital signs, ECGs, physical examinations and Columbia-Suicide Severity Rating Scale.

5.3.2. Pharmacokinetics

Compound A displayed a PK profile suitable for once a day dosing with low peak to trough ratio. Compound A had less than dose-proportional exposure in the fasted state, with absorption enhanced by food (~1.8 fold for $AUC_{inf}$). With multiple doses in the fed state, exposure increased in proportion to dose. Apparent steady state was achieved by Day 6-9, based on the 90% CI for the successive day's exposure ratio within the range 0.8-1.25.

TABLE 11

Pharmacokinetic Parameters in Plasma (Mean ± SD) for SAD Cohort

| Parameter | Compound A 5 mg[a] (N = 3) | Compound A 15 mg[a] (N = 3) | Compound A 20 mg[a] (N = 6) | Compound A 25 mg[b] (N = 6) | Compound A 30 mg[a] (N = 6) |
|---|---|---|---|---|---|
| Tmax (h) | 3.17 ± 2.47 | 4.50 ± 2.60 | 3.69 ± 2.05 | 4.51 ± 1.22 | 3.17 ± 1.48 |
| Cmax (ng/mL) | 7.13 ± 6.12 | 27.3 ± 11.1 | 31.5 ± 21.1 | 45.8 ± 14.3 | 35.5 ± 33.5 |
| $T_{1/2}$ (h) | 49.2 ± 31.1 | 41.9 ± 31.1 | 48.9 ± 14.7 | 97.2 ± 18.0 | 63.4 ± 28.2 |
| $AUC_{0-24}$ (ng*h/mL) | 74.6 ± 50.5 | 328 ± 141 | 376 ± 220 | 482 ± 130 | 369 ± 219 |
| $AUC_{0-t}$ (ng*h/mL)[c] | 91.3 ± 54.2 | 397 ± 166 | 709 ± 337 | 1470 ± 270 | 837 ± 280 |

[a]Fasted for 8 hours prior to dosing and 1 hour after dosing.
[b]Fed a standard breakfast 30 minutes prior to dosing followed by no food for 4 hours.
[c]$t_{Last}$ was 32 h for 5 and 15 mg cohorts, 72 h for 20 and 30 mg cohorts, and 146 h for 25 mg cohort.

TABLE 12

Pharmacokinetic Parameters in Plasma (Mean ± SD) for MAD Cohort

| Parameter | Compound A 15 mg QD Fasted[a] (N = 6) | | Compound A 15 mg Fed[a] (N = 6) | | Compound A 25 mg QD Fed[a] (N = 6) | |
|---|---|---|---|---|---|---|
| Day | Day 1 | Day 7 | Day 1 | Day 10 | Day 1 | Day 10 |
| $T_{max}$ (h) | 2.68 ± 1.15 | 2.69 ± 1.19 | 4.37 ± 1.85 | 3.69 ± 0.506 | 4.38 ± 1.86 | 4.99 ± 1.69 |
| $C_{max}$ (ng/mL) | 10.5 ± 2.01 | 45.1 ± 11.4 | 35.9 ± 11.9 | 60.8 ± 11.2 | 49.6 ± 15.7 | 96.7 ± 8.6 |
| $T_{1/2}$ (h) | — | 167 ± 36.8 | — | 239 ± 179 | — | 218 ± 136 |

TABLE 12-continued

Pharmacokinetic Parameters in Plasma (Mean ± SD) for MAD Cohort

| Parameter | Compound A 15 mg QD Fasted[a] (N = 6) | | Compound A 15 mg Fed[a] (N = 6) | | Compound A 25 mg QD Fed[a] (N = 6) | |
|---|---|---|---|---|---|---|
| Day | Day 1 | Day 7 | Day 1 | Day 10 | Day 1 | Day 10 |
| $AUC_{0-24}$ (ng*h/mL) | 125 ± 32.9 | 757 ± 200 | 353 ± 105 | 1020 ± 246 | 592 ± 133 | 1720 ± 198 |
| $AUC_{0-t}$ (ng*h/mL) | — | 4260 ± 992 | — | 4950 ± 1250 | — | 8010 ± 1520 |

[a] On Days 1 and 7, fasted for 8 hours prior to dosing and 4 hours after dosing. On Days 2-6, fasted for 8 hours prior to dosing and 1 hour after dosing.
[b] Fed a standard breakfast 30 minutes prior to dosing on each dosing day followed by no food for 4 hours.

5.3.3. Safety

Single and multiple doses of Compound A were well tolerated at individual $C_{max}$ levels up to 104 ng/mL and 107 ng/mL, respectively. The majority of AEs were mild or moderate, resolved spontaneously and were consistent with antiepileptic drugs of this class (e.g., dizziness, sedation). There have been no SAEs, deaths, or clinically significant ECG or laboratory findings.

The results suggest that Compound A is safe and well-tolerated up to doses examined (single doses of up to 30 mg and multiple doses of 25 mg QD).

The PK profile (including an effective half-life >24 hours) supports a once per day dosing schedule using an immediate release formulation, with attainment of steady state in 1 week without the need for titration.

5.4. Example 4. Transcranial Magnetic Stimulation Pilot Study

Transcranial magnetic stimulation (TMS), in combination with electromyography (EMG) and electroencephalography (EEG), allows measurement of resting and active motor threshold (RMT/AMT) and TMS-evoked EEG potentials (TEPs), which may indicate drug effects on corticospinal and cortical excitability, respectively. Several antiepileptic drugs (AEDs) have been shown to significantly increase RMT values and modulate TEPs, indicating a shift towards corticospinal/cortical inhibition.

In a pilot study TMS was used to non-invasively determine whether Compound A (10, 15 and 20 mg) impacts cortical excitability. The TMS pilot study was designed to inform sample size calculation for a larger randomized, double-blind and placebo-controlled TMS cross-over study (N=20) with Compound A.

5.4.1 Methods

Eight healthy, right-handed male subjects (aged 21-35 years, 62.4-95.4 kg) from a First-in-Human Phase 1 study were enrolled in this open-label TMS pilot study. RMT, TEPs and EEGs were recorded prior to Compound A, 2 and 4 h post dose. Spectral analysis was performed on resting EEGs. Single-subject level analyses were performed via multiple independent sample t-tests to determine effects of Compound A on TEP amplitudes. Multiple comparisons were accounted for using clusterbased permutation analysis.

5.4.2. Results

Compound A, at 4 h post 20 mg (Cplasma=50±10 ng/mL), suppressed TEP amplitudes at late latencies (e.g. the peak at 180 ms (P180) after TMS by 1.92±0.03 µV, p<0.01, N=3). The 10 mg (N=2) and 15 mg (N=3) dosages, with mean plasma levels of 23.1 and 36.3 ng/mL Compound A at 4 hours, did not show significant and robust TEP modulation. At 4 h post 20 mg, RMT increased 4.3±0.6% from baseline (Poster 3.282) and theta power increased in rEEG. The 20 mg dose of Compound A was selected for use in the placebo-controlled, double-blind, TMS cross-over study.

FIG. 3 shows that Compound A increased motor thresholds (but not SICI) assessed with TMS/EMG. Black bars show effect at 2 hours post-drug intake, grey bars represent 4 hours post-drug (change from baseline as % max stimulator output, mean±SEM). N=2 for 10 mg, N=3 for 15 mg and 20 mg. Compound A 10 mg did not change AMT. N=2 for 10 mg, N=3 for 15 mg and 20 mg.

5.5. Example 5. Transcranial Magnetic Stimulation Crossover Study

A randomized, double-blind, placebo-controlled, transcranial magnetic stimulation (TMS) crossover study investigated the safety, tolerability, pharmacokinetics (PK), and pharmacodynamics (PD) of single doses of Compound A in healthy right-handed male subjects.

The objectives of the study were 1) to evaluate the safety, tolerability and pharmacokinetics of single doses of Compound A in healthy male subjects, and 2) to characterize the effects of Compound A on measures of cortical excitability assessed with TMS-electroencephalogram (EEG) and TMS-electromyogram (EMG) in comparison to placebo.

Twenty healthy right-handed male subjects were enrolled and randomized in a blinded fashion to receive a single oral dose of 20 mg Compound A or placebo (1:1 randomization ratio) on Day 1, then were crossed over to receive a single dose of the other treatment on Day 7.

Subjects were screened within 27 days prior to entering the study on Day 1. For Period 1, subjects were admitted to the study unit and dosed on Day 1, and discharged on Day 2. For Period 2, following a washout of 6 days, the same subjects were again admitted to the study unit and dosed on Day 7, and discharged on Day 8. All subjects returned to the clinical unit for an outpatient visit on Day 14, and received a follow-up telephone call on Day 37.

Subjects were dosed in a fed state, but the timing of dosing relative to meals was changed during the study, and varied between a high fat or standard meal eaten either 2 h or 30 minutes prior to dosing, and a high fat or standard meal eaten 1 h or 2.5 h after dosing.

Safety assessments included adverse events (AEs), clinical laboratory evaluations, vital signs, 12-lead ECG, physical examination, and the Columbia Suicide Severity Rating Scale (C-SSRS).

PK variables included maximal plasma concentration ($C_{max}$), time of maximal plasma concentration ($T_{max}$), terminal elimination half-life ($t_{1/2}$), elimination rate constant ($\lambda z$), area under the curve from 0 to 24 h ($AUC_{0-24\,h}$), area under the curve from time zero to the last quantifiable concentration ($AUC_{0-tlast}$), area under the curve from time zero to infinity ($AUC_{0-inf}$), the percentage of AUC that is due to extrapolation from tlast to infinity (% $AUC_{extrap}$), apparent total body clearance following oral administration (CL/F), CL/F normalized by body weight, mean residence time from time zero to the last quantifiable concentration ($MRT_{last}$), mean residence time extrapolated to infinity ($MRT_{inf}$), apparent volume of distribution during the terminal phase (Vz/F), and Vz/F normalized by body weight.

PD assessments included resting state electroencephalogram (RS-EEG); TMS-EMG measurements including resting motor threshold (RMT), active motor threshold (AMT), and short-interval intracortical inhibition (SICI); and TMS-EEG measurements.

5.5.1. Pharmacokinetic Analysis

The PK parameters for this study were summarized in two ways. Firstly, PK parameters were calculated where possible using the PK samples collected during each 24 h sampling period for Period 1 and Period 2 separately. Secondly, PK parameters were determined using samples beyond the 24 h sampling period (i.e., from Day 7/8 and/or Day 14). For subjects who received Compound A in the first period, PK samples taken prior to placebo treatment provided additional PK timepoints at >24 h. For subjects who received Compound A in the second period, there was no >24 h PK timepoint until a Day 14 PK sample was added. Thus, subjects randomized to receive Compound A in the second period who were enrolled prior to implementation of the additional PK sample at Day 14 did not have PK data beyond 24 h. The full PK profile data set consists of the 16 subjects for whom PK samples were taken at >24 h post-dose. For discussion of the PK parameters below, the full PK profile data set was generally used, because it allowed more accurate estimation of PK parameters.

Initially, subjects were dosed 2 hours after a high fat meal with a relatively high fat lunch provided 1 hour after dosing. After blinded review of the PK profiles in the initial 8 subjects, the fat content of the lunch was reduced in an attempt to reduce the time to $T_{max}$, so that the $C_{max}$ would fall within the timeframe of TMS measurements. In addition, the timing of the meal relative to dose was changed from 2 hours prior, to 30 minutes prior to dose and subsequently the fat content of the breakfast was reduced. All these changes were made in attempts to provide higher plasma levels during the TMS assessment periods. The timing and type of meal for each subject is specified in Table 13. Overall, there was no clear difference in $C_{max}$ or $T_{max}$ despite the changes in meal composition and timing relative to dose. As such the PK data is presented without categorization according to meal content, or relative timing of the meal.

TABLE 13

Type and Timing of Meals Relative to Dosing

| Subjects | Pre-dose Meal | | Post-dose Meal | |
|---|---|---|---|---|
| | Type | Time | Type | Time |
| 901, 908, 910, 907 | High fat[a] | 2 h pre-dose | High fat | 1 h post-dose |
| 912, 919, 914, 918 | High fat | 2 h pre-dose | Standard | 1 h post-dose |

TABLE 13-continued

Type and Timing of Meals Relative to Dosing

| Subjects | Pre-dose Meal | | Post-dose Meal | |
|---|---|---|---|---|
| | Type | Time | Type | Time |
| 927, 925, 928, 924 | High fat | 0.5 h pre-dose | Standard | 2.5 h post-dose |
| 930, 934, 933, 937, 938, 941, 940, 942 | Standard | 0.5 h pre-dose | Standard | 2.5 h post-dose |

[a]Except Subject 910 had standard breakfast prior to dosing

5.5.1.1. Plasma Concentrations

Compound A plasma concentrations over time for the full PK profile were recorded. At the TMS timepoints of 2 h, 4 h and 6 h the mean±SD plasma concentrations were 15.9±21.4 ng/mL, 30.2±21.1 ng/mL and 42.1±19.1 ng/mL, respectively.

There was no difference in mean $C_{max}$ or $T_{max}$ between periods (Table 14). The overall time to peak plasma concentrations ranged from 1.9 to 12 h, with a median time of 7.8 h, indicating that TMS assessments performed at 2, 4 and 6 h occurred prior to $T_{max}$ in the majority of subjects.

Subjects who received placebo in Period 2 had low but measurable Compound A levels at the start of the placebo treatment period, with a mean $C_{max}$ of 5.84 ng/mL (range 3.34-9.61 ng/mL).

TABLE 14

Pharmacokinetic Parameters by Period, Overall, and for Full PK Profile

| | | 20 mg Compound A | | | |
|---|---|---|---|---|---|
| Parameter | Statistic | Period 1 (N = 10) | Period 2 (N = 10) | Overall (N = 20) | Full PK Profile (N = 16) |
| $C_{max}$ (ng/mL) | Mean ± SD | 60.2 ± 17.3 | 58.3 ± 9.94 | 59.2 ± 13.8 | 60.1 ± 14.9 |
| | Range | 29.9-77.1 | 46.2-79.4 | 29.9-79.4 | 29.9-79.4 |
| $T_{max}$ (h) | Median | 6.94 | 7.83 | 7.83 | 6.83 |
| | Range | 1.92-12 | 1.92-8.15 | 1.92-12 | 1.92-12 |
| $AUC_{0-24}$ (ng*h/mL) | Mean ± SD | 693 ± 184 | 681 ± 142 | 687 ± 160 | 692 ± 151 |
| | Range | 383-951 | 358-869 | 358-951 | 383-951 |
| $C_{last}$ (ng/mL) | Mean ± SD | 16.4 ± 5.61 | 16.4 ± 3.87 | 16.4 ± 4.69 | 4.52 ± 1.82 |
| | Range | 10.1-27.8 | 7.1-21.3 | 7.1-27.8 | 1.33-7.67 |
| $T_{last}$ (h) | Mean ± SD | 23.8 ± 0.375 | 23.8 ± 0.213 | 23.8 ± 0.299 | 235 ± 81.5 |
| | Range | 23.1-24.3 | 23.5-24.1 | 23.1-24.3 | 142-360 |
| $T_{1/2}$ (h) | Mean ± SD | 11.4 ± 2.6 | 10.6 ± 2.9 | 11.1 ± 2.6 | 127 ± 84.6 |
| | Range | 8.46-14.9 | 8.01-14.3 | 8.01-14.9 | 48.2-306 |

5.5.1.2. Other Pharmacokinetic Parameters for Full PK Profile

A summary of other PK parameters is provided in Table 15. The mean $AUC_{last}$ was 2370 ng*h/mL, which included PK samples from follow-up visits when available. The $AUC_{inf}$ from the same data set was 3155 ng*h/mL and the median (range) extrapolated area was 19.9% (range 10.6-40.5%). This relatively high level of extrapolated area in some subjects suggests that the parameters calculated from $\lambda z$ (such as half-life, $MRT_{inf}$, clearance, and volume of distribution) should be analyzed with caution and may have higher inherent variance in their calculation.

The mean normalized volume of distribution (Vz/F) of 16.3 L/kg was well above total blood volume for the mean body weight of 72.3 kg, indicating that the drug distributes out of plasma into surrounding tissues.

Body weight normalized clearance (CL/F) was 97.5 mL/h/kg (equivalent to approximately 1.6 mL/min/kg). This value is plasma clearance, not blood clearance; however, even adjusting for hematocrit, it is well below total hepatic blood flow of 17 mL/min/kg (Carlisle et al., *Gut* 1992, 33:92-97), suggesting a low extraction drug.

TABLE 15

Pharmacokinetic Parameters (Full PK Data Set)

| | 20 mg Compound A Full PK Profile Data Set (N = 16) | |
|---|---|---|
| Parameter | Mean ± SD | Range |
| $AUC_{last}$ (ng*h/mL) | 2370 ± 680 | 1583 ± 4400 |
| $AUC_{inf}$ (ng*h/mL) | 3155 ± 1341 | 1923 ± 7393 |
| Vz/F normalized (L/kg) | 16.3 ± 9.06 | 6.4 ± 33.8 |
| $t_{1/2}$ (h) | 127 ± 84.6 | 48.2 ± 306 |
| $MRT_{last}$ (h) | 77.4 ± 23.7 | 48.2 ± 122 |
| $MRT_{inf}$ (h) | 102 ± 84.8 | 33 ± 304 |
| CL/F normalized (mL/h/kg) | 97.5 ± 25.7 | 40.3 ± 136 |

5.5.1.3. Pharmacokinetic Conclusions

Compound A was slowly absorbed after a 20 mg oral dose with median peak plasma concentrations occurring approximately 8 hours after administration. Upon absorption, it distributed out of plasma into surrounding tissues and was slowly cleared from systemic circulation at rates well below hepatic blood flow, indicating minimal hepatic extraction (metabolism). It exhibited a mean half-life of 127 h (range 48.2-306 h) and mean residence time of 102 h (range 33-304 h) which may be an underestimation since a number of subjects had % $AUC_{extrap}$ values above 20% and as high as 40%.

Washout between periods was not long enough to allow Compound A levels fall below the limit of quantitation in subjects who received placebo in Period 2 (mean 3.1 ng/mL, range 1.3-6.8 ng/mL).

5.5.2. Pharmacodynamic Analysis

All 20 subjects underwent TMS-EMG and TMS-EEG sessions prior to dosing on Days 1 and 7 and at 2 and 4 h after dosing. Due to a prolonged absorption phase for Compound A revealed by pharmacokinetic analysis, extra measurements were added at 6 hours after drug intake. For the 6 h timepoint, RMT was performed for 16 subjects, and AMT, EEG resting state, and TMS-EEG was performed for 8 subjects.

Subject 912 did not undergo any of the PD assessments at the 2 h timepoint in the Compound A treatment period due to side effects (vomiting). TMS procedures could not be completed for Subject 940 at 2 h in the placebo treatment period due to technical problems, so at 2 h this subject only underwent RMT and resting state EEG procedures.

Compound A-induced modulation of PD markers was evaluated as an effect of time (comparisons of 2, 4, and 6 h post-dose vs. pre-dose) and of concentration (using the post-dose measure taken during highest drug exposure vs. baseline).

Analyses were performed for all subjects (n=20) and for the subjects (n=16) who showed drug plasma levels higher than the highest concentration detected as the carry-over effect in the placebo arm (Table 16).

TABLE 16

Individual Compound A Plasma Concentrations Obtained 5 minutes Before TMS-EMG/EEG Measurements

| | Compound A Plasma Concentration | | | | | |
|---|---|---|---|---|---|---|
| | Compound A Treatment Period | | | Placebo Treatment Period | | |
| Subject | 2 h | 4 h | 6 h | 2 h | 4 h | 6 h |
| 901[a] | 0 | 6.08 | —[b] | 0 | 0 | —[b] |
| 908 | 64.2 | 76.5 | —[b] | 6.05 | 7 | —[b] |
| 910 | 47.2 | 38.7 | —[b] | 0 | 0 | —[b] |
| 907 | 1.55 | 8.92 | —[b] | 4.96 | 4.35 | —[b] |
| 912 | 34 | 48.4 | 49.7 | 0 | 0 | 0 |
| 919 | 0 | 16.5 | 71.2 | 5.27 | 4.48 | 5.56 |
| 914 | 55.2 | 50 | 48.5 | 6.28 | 5.51 | 5.75 |
| 918 | 10.6 | 24.5 | 47.0 | 0 | 0 | 0 |
| 927 | 47.1 | 38 | 39.1 | 3.81 | 3.6 | 3.42 |
| 925[a] | 0 | 4.91 | 37.6 | 0 | 0 | 0 |
| 928[a] | 0 | 2.54 | 4.43 | 0 | 0 | 0 |
| 924 | 3.1 | 29.8 | 51.9 | 5.74 | 5.36 | 5.61 |
| 930[a] | 1.95 | 4.06 | 6.23 | 3.94 | 3.66 | 3.44 |
| 934 | 25.7 | 60.7 | 57.6 | 0 | 0 | 0 |
| 933 | 0 | 22.3 | 53.2 | 0 | 0 | 0 |
| 937 | 2.74 | 32.7 | 54.9 | 7.44 | 6.83 | 6.67 |
| 938 | 10.7 | 52.1 | 52.2 | 0 | 0 | 0 |
| 941 | 0 | 8.77 | 25.1 | 8.04 | 8.15 | 8.22 |
| 940 | 2.52 | 41.9 | 79.4 | 0 | 0 | 0 |
| 942 | 8.01 | 35.7 | 32.8 | 3.11 | 2.77 | 2.87 |
| Mean | 15.88 | 30.15 | 42.08 | 5.46 | 5.17 | 5.28 |
| SD | 21.41 | 21.09 | 19.13 | 1.58 | 1.73 | 1.70 |

[a]Subjects who did not reach concentrations higher than the carry-over effect observed in the placebo arm (carryover effect level was 8.22 ng/mL, observed in Subject 941 at 6 h post-dose in placebo treatment period). Subjects 901, 925, 928, and 930 were not included in the concentration and time analysis for TEPs, TMS-induced oscillations and resting state EEG (n = 16). Subject 925 did reach a concentration of 37.6 ng/mL at 6 h post-dose, but only had RMT assessed at that timepoint.
[b]Subjects were treated before the protocol was amended to add the 6 h timepoint.

5.5.2.1. TMS-Evoked EGG Potentials

TMS-evoked EEG potentials (TEPs) were calculated by averaging artefact-free EEG trials in the different experimental conditions (Table 17).

TABLE 17

Number of Artefact-Free Trials

| | Number of Artefact Free EEG Trials (Mean ± SD) | | | |
|---|---|---|---|---|
| | Pre-dose | 2 h Post-dose | 4 h Post-dose | 6 h Post-dose |
| Placebo | 128 ± 13 | 121 ± 10 | 125 ± 10 | 125 ± 13 |
| Compound A | 130 ± 11 | 124 ± 11 | 123 ± 11 | 131 ± 11 |

The following TEP components (P=positive, N=negative) in accordance with the literature were studied, value in parenthesis is the time of interest (TOI): P25 (15-35 ms), N45 (35-70 ms), P70 (70-80 ms), N100 (80-145 ms), and P180 (145-230 ms). TOIs were chosen on the basis of the grand-averaged TEPs and kept identical during the analysis of pre-dose and post-dose measurements and across conditions. To analyze drug-induced modulation of TEPs, we selected a region of interest (ROI) that was composed of 27 channels over and around the stimulation site (left M1) and the corresponding contralateral site ('FC1', 'FC3', 'FC5', 'C1', 'C3', 'C5', 'CP1', 'CP3', 'CP5', 'P1', 'P3', 'P5', 'Cz', 'CPz', 'Pz', 'FC2', 'FC4', 'FC6', 'C2', 'C4', 'C6', 'CP2', 'CP4', 'CP6', 'P2', 'P4', 'P6').

To analyze significance of TEP amplitude modulations induced by Compound A, multiple dependent sample t-test comparisons (post-dose vs. pre-dose) were applied for each TOI in all the electrodes within the indicated ROI. To correct for multiple comparisons (i.e., electrodes, timepoints), we conducted a non-parametric cluster-based permutation analysis as implemented in FieldTrip.

The spatiotemporal profile of the TMS-evoked EEG potentials is in line with previous reports in literature (FIG. 4-A). Early components (N15, P25) are predominantly located at the stimulated left M1, followed by a pronounced negativity over the contralateral site corresponding to the N45 potential. Finally, the N100 and P180 components confirm their optimal topographical reproducibility over left-central and centro-frontal regions, respectively (FIG. 4-B). The comparison between pre-dose conditions (placebo versus Compound A) did not show significant differences (p>0.05). These results apply for n=20 and n=16 data sets. FIG. 4 shows that Compound A yielded significant modulation of early TEPs (N45 and P180).

Concentration analysis (N=16): The cluster-based permutation analysis was applied between post-dose and pre-dose conditions to test the effect of Compound A at the highest plasma concentration available during the TMS assessment timepoints. Although time-matched placebo did not show any significant changes, Compound A decreased the amplitude of the early TEP components measured from 15 to 35 ms (peak-to-peak amplitude of the early complex N15-P25: 4.5 vs 6.0 µV, p<0.05), at 45 ms (N45: −2.3 vs −3.0 µV, p<0.01) and at 180 ms (P180: 2.2 vs 3.0 µV, p<0.01) after the TMS pulse (FIG. 4-D, FIG. 5). FIG. 6 shows that Compound A significantly modulates TEPs and decreases cortical excitability.

Time analysis (subjects with drug exposure at time of measurement): The cluster-based permutation analysis was applied between post-dose and pre-dose conditions to test the effects of Compound A at 2 h (n=15), 4 h (n=16), and 6 h (n=7) after dosing in subjects with adequate Compound A exposure during the first 6 h. Compared to pre-dose, the first N15-P25 complex was decreased at 2 h (p=0.008) and 4 h (p=0.02). Further, at 4 h after dosing Compound A significantly suppressed the N45 (p=0.03), the N100 (p=0.04), and the P180 (p=0.004) (FIG. 7).

Other comparisons were not statistically significant (p>0.05) and placebo did not induce significant changes (p>0.05).

Time analysis (all available subjects): The cluster-based permutation analysis was applied between post-dose and pre-dose conditions to test the effects of Compound A at 2 h (n=19), 4 h (n=20), and 6 h (n=8) after dosing in all available subjects. Compared to pre-dose, the first N15-P25 complex was decreased at 2 h (p=0.006) and 4 h (p=0.01). Further, at 4 h after dosing Compound A significantly suppressed the N45 (p=0.03) and the P180 (p=0.02). This shows that Compound A modulates TEPs and decreases cortical excitability.

Other comparisons were not statistically significant (p>0.05) and placebo did not induce significant changes (p>0.05).

5.5.2.2. TMS-Induced Oscillations

Single-pulse TMS applied over the left motor cortex resulted in a series of changes in the power of ongoing oscillatory activity. Before drug intake, at baseline, TMS induced an early increase of theta/alpha power followed by a beta power decrease (de-synchronization) and a final late response of increased beta power.

The effects of the active compound on TMS-induced oscillations were then analysed by means of a cluster-based permutation analysis following the same procedure as adopted in the analysis of TEPs. Theta (4-7 Hz), alpha (8-12 Hz) and beta (13-30 Hz) TMS-induced oscillations were compared from 30 ms (the first time-frequency point considered artefact free) to 800 ms between drug conditions. This method was preferred instead of a predetermined set of time windows, given the absence of a consensus for time windows of interest to be used in the TMS induced oscillation analysis. Also, the present cluster-based statistics approach is appropriate for exploratory analyses, as it minimizes false-positives involved in testing multiple timepoints.

Concentration analysis (N=16): The cluster-based permutation analysis was applied between post-dose and pre-dose conditions to test the effect of Compound A at the highest plasma concentration present during TMS assessment. Compound A suppressed early theta TMS-induced oscillations (p<0.001; significant effects from 30 to 390 ms), alpha TMS-induced oscillations (p=0.02; significant effects from 220 to 400 ms) and increased beta TMS-induced power (p=0.04; significant effects from 220 to 310 ms)

Other comparisons were not statistically significant (p>0.05) and placebo did not induce significant changes (p>0.05).

Time analysis (subjects with drug exposure at time of measurement): The cluster-based permutation analysis was applied between post-dose and pre-dose conditions to test the effects of Compound A at 2 h (n=15), 4 h (n=16), and 6 h (n=7) after dosing. Compared to pre-dose, Compound A did not modulate oscillations registered 2 h post-dose whereas at 4 h Compound A suppressed early theta TMS-induced oscillations (p=0.03; significant effects from 30 to 180 ms), alpha TMS-induced oscillations (p=0.03; significant effects from 250 to 390 ms) and increased beta TMS-induced desynchronization (p=0.04; significant effects from 250 to 330 ms). Finally, at 6 h post-dose, results showed a significant depression of theta induced oscillations (p<0.001; significant effects from 30 to 280 ms).

Other comparisons were not statistically significant (p>0.05) and placebo did not induce significant changes (p>0.05).

Time analysis (all available subjects): The cluster-based permutation analysis was applied between post-dose and pre-dose conditions to test the effects of Compound A at 2 h (n=19), 4 h (n=20), and 6 h (n=8) after dosing. Compared to pre-dose, Compound A showed a trend to suppress theta TMS-induced oscillations at 2 h post-dose. At 4 h Compound A suppressed alpha TMS-induced oscillations (p=0.03; significant effects from 250 to 400 ms). Finally, at 6 h post-dose, results showed a significant depression of theta induced oscillations (p=0.03; significant effects from 80 to 300 ms) and a trend to suppress alpha band (trend p=0.07; 270-390 ms).

Other comparisons were not statistically significant (p>0.05) and placebo did not induce significant changes (p>0.05).

5.5.2.3. Resting State EEG

Sensor-level delta (2-4 Hz), theta (4-7 Hz), alpha (8-12 Hz) and beta (13-30 Hz) frequency activity was estimated using a Fast Fourier Transform (FFT) approach. Power of all frequencies between 2 and 30 Hz were estimated, using a frequency resolution of 0.5 Hz. A non-parametric dependent samples t-test based on a permutation approach (1500 permutations) was used to test differences between drug conditions on all EEG sensors.

Concentration analysis (N=16): During high Compound A plasma exposure, resting state oscillatory activity was significantly modulated showing an increase in power at delta (p<0.001), theta (p=0.01) and beta (p=0.005). Placebo induced an increase in theta power (p=0.001) and all other comparisons showed no significant results.

Computed differences between post-dose and pre-dose states within each drug condition, and then statistically compared the calculated differences (post-dose minus pre-dose) between Compound A and placebo. Compared to placebo, Compound A induced an overall increase of power for delta (p<0.001), theta (p=0.02), and beta (p=0.003) (FIG. 8).

Time analysis (subjects with drug exposure at time of measurement): The cluster-based permutation analysis was applied between post-dose and pre-dose conditions to test the effects of Compound A at 2 h (n=15), 4 h (n=16), and 6 h (n=7) after dosing.

Compared to the pre-dose state, Compound A significantly increased the power of low frequency oscillations (2 h post-dose versus pre-dose: delta, p=0.001; theta, p=0.01; 4 h post-dose versus pre-dose: delta, p<0.001; theta, p=0.01) and of beta band (2 h post-dose versus pre-dose: p=0.01; 4 h post-dose versus pre-dose: p<0.001) (FIG. 9).

Placebo caused an increase in theta band 4 hours after drug intake (p=0.003) whereas all other comparisons were not statistically significant (p>0.05).

Time analysis (all available subjects): The cluster-based permutation analysis was applied between post-dose and pre-dose conditions to test the effects of Compound A at 2 h (n=19), 4 h (n=20), and 6 h (n=8) after dosing.

Compared to the pre-dose state, Compound A significantly increased the power of low frequency oscillations (2 h post-dose versus pre-dose: delta, p<0.001; theta, p=0.006; 4 h postdose versus pre-dose: delta, p<0.001; theta, two clusters at p=0.008 and p=0.03) and of beta band (2 h post-dose versus pre-dose: p=0.005; 4 h post-dose versus pre-dose: p<0.001; 6 post-dose versus pre-dose: p=0.009).

Placebo caused an increase in delta (2 h post-dose versus pre-dose: two clusters p=0.02 and p=0.04; 4 h post-dose versus pre-dose: two clusters p=0.004 and p=0.01; 6 h post-dose versus pre-dose: p=0.05) and theta band power (4 h post-dose versus pre-dose: p<0.001; 6 h post-dose versus pre-dose: p=0.009), alpha band (6 h post-dose versus pre-dose: p=0.04) and beta band (6 h post-dose versus pre-dose: p=0.04), whereas all other comparisons were not statistically significant (p>0.05).

5.5.2.4. TMS-EMG

RMT and AMT values are reported as percentages of maximum stimulator output (% MSO). Drug-induced modulation of TMS-EMG parameters were evaluated over the 3 timepoints (2, 4, and 6 h) and for the timepoint with the highest drug exposure.

5.5.2.4.1. Resting Motor Threshold

Individual and averaged RMT values at baseline and change each timepoint for Compound A and placebo for all 20 subjects are presented in Table 18. Four subjects (901, 925, 928, and 930) did not have high drug exposure during TMS measurements. In addition, RMT could not be registered for Subject 912 at 2 hours after Compound A intake.

TABLE 18

Resting Motor Threshold (% MSO) Before and After Treatment

| | Resting Motor Threshold (% MSO) | | | | | | | |
|---|---|---|---|---|---|---|---|---|
| | Placebo | | | | Compound A | | | |
| | Pre-dose | Post-dose Change from Baseline | | | Pre-dose | Post-dose Change from Baseline | | |
| Subject | Value | 2 h | 4 h | 6 h | Value | 2 h | 4 h | 6 h |
| 901[a] | 47 | 0 | 0 | —[b] | 47 | 0 | 1 | —[b] |
| 908 | 49 | −1 | −1 | —[b] | 51 | 3 | 7 | —[b] |
| 910 | 44 | −3 | −3 | —[b] | 41 | 1 | 1 | —[b] |
| 907 | 62 | 1 | 3 | —[b] | 62 | 0 | 0 | —[b] |
| 912 | 63 | 0 | 0 | 0 | 61 | —[c] | 6 | 8 |
| 919 | 65 | 0 | 0 | 1 | 66 | 0 | 0 | 4 |
| 914 | 39 | 0 | 0 | 0 | 38 | 2 | 3 | 4 |
| 918 | 52 | 2 | 3 | 2 | 52 | 3 | 5 | 6 |
| 927 | 78 | 1 | 1 | 1 | 77 | 3 | 10 | 10 |
| 925[a] | 49 | −1 | 0 | 0 | 48 | 1 | 1 | 4 |
| 928[a] | 52 | 4 | 5 | 3 | 52 | 2 | 1 | 1 |
| 924 | 47 | 2 | 3 | 2 | 47 | 1 | 2 | 1 |
| 930[a] | 48 | 1 | 1 | 1 | 49 | 0 | 0 | 0 |
| 934 | 45 | 0 | 2 | 2 | 46 | 3 | 3 | 7 |
| 933 | 48 | 0 | 0 | 0 | 48 | 0 | 0 | 3 |
| 937 | 66 | 0 | 0 | 2 | 63 | 0 | 2 | 7 |
| 938 | 57 | 0 | 0 | 1 | 55 | 0 | 3 | 3 |
| 941 | 79 | 0 | 0 | 0 | 77 | 6 | 6 | 6 |
| 940 | 39 | 0 | −1 | −1 | 39 | 2 | 4 | 8 |
| 942 | 54 | 1 | 1 | 2 | 54 | 1 | 7 | 7 |
| Mean | 54.2 | 0.4 | 0.7 | 0.9 | 53.7 | 1.5 | 3.1 | 4.9 |
| SD | 11.4 | 1.4 | 1.8 | 1.1 | 11.1 | 1.6 | 2.9 | 2.8 |

[a]Subjects who had low plasma levels of Compound A during TMS assessments, as shown in Table 16.
[b]Subjects were treated prior to addition of 6 h timepoint.
[c]RMT could not be registered for Subject 912 at this timepoint.

There were no significant differences between baseline values in either group. Compound A treatment resulted in a significant increase in RMT indicating reduced corticospinal excitability (FIGS. 10 and 11). There was a strong relationship between the PD effect and the mean Compound A plasma concentrations, with an effect on RMT of >4% at 6 h post-dose. FIG. 8 shows that RMT increased in proportion to Compound A plasma concentration with a mean±SEM increase of 4.9±0.7% at 6 h. This significant increase in RMT indicates reduced corticospinal excitability and thus represents a strong PK-PD relationship.

5.5.2.4.2. Active Motor Threshold

AMT was recorded while subjects squeezed a manometer at 20% of each individual's maximum contraction force. Table 19 shows individual and averaged AMT values at each timepoint for Compound A and placebo. AMT could not be registered for Subjects 912 and 940 at 2 hours after Compound A and placebo intake, respectively.

There were no significant differences between baseline values in either group. AMT increased following Compound A treatment. The change from baseline in AMT for Compound A was significantly different from placebo at 6 h post-dose (p<0.01).

TABLE 19

Active Motor Threshold (% MSO) Before and After Dosing

| | Active Motor Threshold (% MSO) | | | | | | | |
|---|---|---|---|---|---|---|---|---|
| | Placebo | | | | Compound A | | | |
| | Pre-dose | Post-dose Change from Baseline | | | Pre-dose | Post-dose Change from Baseline | | |
| Subject | Value | 2 h | 4 h | 6 h | Value | 2 h | 4 h | 6 h |
| 901[a] | 37 | 0 | 0 | —[b] | 38 | 0 | 0 | —[b] |
| 908 | 39 | 1 | 1 | —[b] | 40 | 2 | 2 | —[b] |
| 910 | 34 | 0 | 0 | —[b] | 31 | 4 | 4 | —[b] |
| 907 | 46 | −1 | −1 | —[b] | 46 | 0 | 0 | —[b] |
| 912 | 52 | −4 | −12 | −12 | 45 | —[c] | 0 | 0 |
| 919 | 50 | 0 | 0 | 0 | 50 | 0 | 0 | 0 |
| 914 | 30 | 1 | 1 | 1 | 29 | 3 | 3 | 6 |
| 918 | 42 | 1 | 1 | 0 | 41 | 1 | 1 | 1 |
| 927 | 55 | 0 | 0 | 0 | 57 | 2 | 3 | 0 |
| 925[a] | 37 | 0 | 0 | 0 | 37 | 1 | 0 | 0 |
| 928[a] | 37 | 5 | 5 | 5 | 38 | 0 | 0 | 2 |
| 924 | 37 | 0 | 2 | 1 | 35 | 1 | 3 | 3 |
| 930[a] | 39 | 0 | 0 | 0 | 40 | 0 | 0 | 1 |
| 934 | 36 | 1 | 1 | 1 | 36 | 0 | 2 | 3 |
| 933 | 36 | 0 | 1 | 1 | 36 | 0 | 0 | 4 |
| 937 | 53 | −1 | −1 | −1 | 51 | 0 | 0 | 1 |
| 938 | 43 | 0 | 0 | 0 | 41 | 0 | 2 | 3 |
| 941 | 55 | 0 | 0 | 0 | 56 | 1 | 1 | 2 |
| 940 | 33 | —[c] | −1 | −1 | 35 | 2 | 2 | 3 |
| 942 | 42 | 0 | 0 | 0 | 41 | 1 | 3 | 3 |
| Mean | 41.7 | 0.2 | −0.2 | −0.3 | 41.2 | 0.9 | 1.3 | 2.0 |
| SD | 7.7 | 1.6 | 3.1 | 3.3 | 7.6 | 1.2 | 1.4 | 1.7 |

[a]Subjects who had low plasma levels of Compound A during TMS assessments, as shown in Table 16.
[b]Subjects were treated prior to addition of 6 h timepoint.
[c]AMT could not be registered at this timepoint.

5.5.2.4.3. Short Interval Intracortical Inhibition

Short-interval intracortical inhibition (SICI) was measured using 15 conditioning-test stimuli pairs given in a random order at an interstimulus interval (ISI) of 2 ms. The conditioning stimulus was set at 80% of AMT and the suprathreshold stimulus 120% RMT.

The calculation of SICI utilized custom scripts to measure the amplitudes of conditioned and unconditioned motor evoked potentials (MEPs) and to express SICI as the ratio of mean conditioned MEPs over mean unconditioned MEPs.

SICI values (mean conditioned MEPs/mean unconditioned MEPs) are reported for each individual, experimental session and Compound A dose (Table 20). Average and SD are also reported for each condition. There were no significant findings.

TABLE 20

SICI Values Before and After Dosing

| | Short Intracortical Inhibition (Mean Conditioned MEP/Mean Unconditioned MEP) | | | | | |
|---|---|---|---|---|---|---|
| | Placebo | | | Compound A | | |
| Subject | Pre-dose | 2 h | 4 h | Pre-dose | 2 h | 4 h |
| 901[a] | 1.32 | 1.18 | 0.91 | 1.56 | 0.85 | 1.07 |
| 908 | 0.79 | 0.76 | 0.54 | 0.53 | 0.67 | 1.02 |
| 910 | 1.11 | 0.83 | 0.86 | 0.90 | 0.71 | 1.03 |
| 907 | 0.90 | 0.98 | 0.86 | 0.75 | 0.72 | 0.93 |
| 912 | 1.12 | 0.96 | 0.91 | 1.15 | —[b] | —[b] |
| 919 | 1.09 | 1.33 | 0.82 | 0.94 | 1.29 | 0.54 |
| 914 | 1.03 | 1.04 | 1.08 | 1.48 | 0.91 | 1.20 |
| 918 | 1.02 | 0.83 | 0.75 | 0.79 | 0.94 | 1.68 |
| 927 | 1.10 | 0.59 | 0.93 | 1.18 | 1.11 | 1.64 |
| 925[a] | 1.17 | 1.22 | 0.85 | 1.20 | 0.96 | 0.86 |
| 928[a] | 1.13 | 1.20 | 0.78 | 1.22 | 1.18 | 0.61 |
| 924 | 1.38 | 1.14 | 1.18 | 0.79 | 2.68 | 1.01 |
| 930[a] | 1.02 | 1.00 | 1.22 | 0.84 | 0.92 | 1.53 |
| 934 | 1.13 | 0.77 | 1.05 | 1.32 | 0.91 | 1.04 |
| 933 | 0.83 | 1.22 | 0.91 | 1.18 | 0.92 | 1.03 |
| 937 | 0.63 | 1.08 | 2.03 | 1.20 | 0.97 | 1.17 |
| 938 | 0.62 | 1.34 | 1.06 | 1.13 | 1.12 | 0.89 |
| 941 | 0.53 | 0.86 | 0.87 | 1.47 | 1.31 | 1.27 |
| 940 | 1.29 | —[b] | —[b] | 0.78 | 1.09 | 0.87 |
| 942 | 1.18 | 0.71 | 1.00 | 1.65 | 1.03 | 0.75 |
| Mean | 1.02 | 1.00 | 0.98 | 1.05 | 1.07 | 1.06 |
| SD | 0.23 | 0.22 | 0.30 | 0.29 | 0.43 | 0.31 |

[a]Subjects who had low plasma levels of Compound A during TMS assessments, as shown in Table 16.
[b]Data not available for this timepoint.

5.5.2.5. Pharmacodynamic Conclusions

Pharmacodynamic assessments were performed to determine the acute effects of the potassium channel opener Compound A on corticospinal and cortical excitability as measured with TMS-EMG and TMS-EEG, respectively.

5.5.3. TMS-EMG Measures

The motor threshold (at rest and under active muscular contraction) has been linked to ion channel conductivity, and hence to neural membrane excitability, as it was increased by several antiepileptic drugs (AEDs) acting on sodium channels (i.e. lamotrigine, carbamazepine; Ziemann et al., *J. Int. Fed. Clin. Neurophys.* 2015, 126:1847-1868) and potassium channels (i.e. retigabine; Ossemann et al., *Epilepsy Res.* 2016, 126:78-82).

In addition, intracortical inhibition can be tested by SICI, a well-established TMS paired pulse paradigm. SICI can assess synaptic excitability of interneurons within the stimulated motor cortex and it has been associated to GABA-A receptor mediated neurotransmission.

Results showed that Compound A significantly impacted the motor threshold indicating a reduced corticospinal excitability. The RMT was particularly modulated in a time and plasma concentration dependent manner in comparison to placebo. At 2, 4, and 6 h post-dose, a single 20 mg dose of Compound A increased RMT from baseline compared to time matched placebo. Further, the increases in RMT at each timepoint correlated with the increase in Compound A systemic exposure.

The AMT was modulated to a lower extent and was significantly different from placebo only at 6 h post-dose. The nature of the discrepancy between RMT and AMT results is not known, however it is in line with other AEDs (Ziemann et al., *Ann. Neuro.* 1996, 40:367-378). During voluntary muscle activation, a decrease in motor threshold is believed to occur through an increased excitability of the corticospinal output or spinal motor neurons or both. Subthreshold activation of the former elements, which are probably also targeted by TMS, explains why AMT increases less than RMT by drugs acting on membrane ion channels. During voluntary muscular activation, many physiological and anatomical elements in addition to what is directly activated by TMS play a role and this would explain why the drug-induced modulation of the AMT is more limited than RMT. Finally, the lack of an effect on SICI indicates that Compound A does not alter GABA-A receptor mediated intracortical inhibition. This result is in line with TMS-EMG report of retigabine (Ossemann et al., 2016) and sodium channel blockers (Ziemann et al., 1996).

5.5.4. TMS-EEG Measures

Compound A significantly modulated TMS-EEG and resting state EEG output showing a unique fingerprint at the highest drug plasma concentration. In addition, the drug-induced modulation followed drug plasma exposure with strongest effects at 4 hours after drug intake (Table 21).

TABLE 21

Compound A Induced Modulation of TEPs, TMS-induced Oscillations and Resting State EEG Bands

| | Compound A Induced Modulation | | |
|---|---|---|---|
| | At Highest Compound A Plasma Concentration | At Time After Dosing | |
| | | 2 h | 4 h |
| TEPs | ↓ N15-P25 | ↓ N15-P25 | ↓ N15-P25 |
| | ↓ N45 | Not significant | ↓ N45 |
| | ↓ P180 | Not significant | ↓ P180 |
| TMS-induced oscillations | ↓ Theta 30-390 ms | Not significant | ↓ Theta 30-180 ms |
| | ↓ Alpha 220-400 ms | Not significant | ↓ Alpha 250-390 ms |
| | ↑ Beta 210-310 ms | Not significant | ↑ Beta 250-330 ms |
| Resting state EEG | ↑ Delta | ↑ Delta | ↑ Delta |
| | ↑ Theta | ↑ Theta | ↑ Theta |
| | ↑ Beta | | ↑ Beta |

Additional measures of cortical excitability including global mean field power were similarly impacted. Global mean field power (GMFP) shows the overall amount of electrical activity induced by TMS. FIG. 12 shows that Compound A causes reduction of cortical excitability over time with prolonged absorption. Compound A also shifted the power spectra of resting state EEGs toward lower frequencies.

TMS-EEG allows measurement of the pharmacological effect of drugs acting in the brain. This aspect is particularly appealing for epilepsy research where despite the wide range of AEDs, seizures are refractory to treatment in 30% of cases and long-term therapeutic outcome cannot be predicted (Kwan and Brodie, *N. Engl. J. Med.* 2000, 342:314-319). Lamotrigine and levetiracetam, two of the most prescribed AEDs, were previously evaluated with TMS-EEG. Lamotrigine is a voltage-gated Na+ channel blocker, whereas levetiracetam binds to synaptic vesicles protein 2A (SV2A) to inhibit the release of excitatory neurotransmitter (Rogawski and Löscher, *Nat. Rev. Neurosci.* 2004, 5:553-564). At the system level, both drugs increased the amplitude of the N45 and suppressed the P180 component (Premoli et al., *Epilepsia* 2016, 58:42-50).

In the TMS-EEG portion of the study, 20 mg of Compound A produced statistically significant modulations of TEPs in a manner consistent with reductions in cortical excitability. Relative to time-matched placebo, at the time of the highest plasma levels during TMS assessments Compound A decreased the amplitude of the first N15-P25 complex, the N45 and the P180 potentials offering a unique fingerprint. The N15 component is generated in the ipsilateral premotor cortex whereas the origin of P25 is less clear, but may reflect activity around ipsilateral sensorimotor/premotor cortex border, in the superior wall of the ipsilateral cingulate gyrus or supplementary motor area, and in the contralateral cortex (Maki and Ilmoniemi, *Neurosci. Lett.* 2010, 478:24-28). The N15-P25 complex has been inversely correlated with MEP amplitude, thus providing information about the excitability of the stimulated area. Following this interpretation, the reduction of the peak-to-peak amplitude of these early components may reflect the drug-induced reduction of cortical excitability. Over time, Compound A suppressed the N45 amplitude which has been linked to GABA-A receptor mediated neurotransmission by trials that manipulated TEPs with benzodiazepines as GABAergic positive modulators (Premoli et al., *J. Neurosci.: J. Soc. Neurosci.* 2014, 34:5603-5612; Darmani et al., *J. Neurosci.: J. Soc. Neurosci.* 2016, 36:12312-12320). The reduction of the N45 could reflect less GABA-A receptor mediated inhibition due to activation of pre-synaptic GABA-A receptor which decreases GABA release into the synaptic cleft. As an alternative explanation, the TMS response did not propagate to the contralateral hemisphere given the overall increase in cortical inhibition and this implies a reduction of the N45 amplitude over distant sites. Finally, the reduction of the P180 component is in line with the observation from other AEDs (Premoli et al., 2016).

In addition to TEPs, brain responses to TMS can be investigated by applying a time-frequency analysis at single trial level removing the evoked (i.e. TEP) component from the signal. TMS-induced oscillations are the result of this analytical approach and they provide non-phase locked neural information (Premoli et al., *Neuroimage* 2017, 163: 1-12). The impact of compounds acting towards GABAergic neurotransmission on TMS-induced oscillations showed that the early α-synchronization was increased by the GABA-Aergic drugs and decreased by the GABA-Bergic drug, the late α-desynchronization was increased by the GABA-Bergic drug, and the late (3-desynchronization was increased by GABA-Aergic and GABA-Bergic drugs.

Compound A showed a unique profile of modulation of induced responses consisting of suppression of theta and alpha TMS-induced power and further increase of beta TMS-induced desynchronization. In the absence of TMS stimulation, during rest, the spontaneous brain oscillatory activity is modulated showing a power increase for delta, theta and beta bands.

TMS-EMG and TMS-EEG results show that 20 mg of Compound A, once across the blood brain barrier, impacts cortical excitability as demonstrated by the modulation of the array of PD markers. The intrinsic neuronal membrane properties and the level of cortical excitation and inhibition are relevant points in epileptogenesis. Therefore, these study endpoints may play a crucial role when determining the therapeutic effects of Compound A in epilepsy patients. For instance, the RMT is lower in drug-naïve patients compared to healthy controls and the intracortical inhibition is impaired. For this specific compound, changes in RMT and other PD markers before and after treatment can be used to assess Compound A therapeutic responsiveness.

All of the U.S. patents, U.S. patent application publications, U.S. patent applications, foreign patents, foreign patent applications, and non-patent publications referred to in this specification are incorporated herein by reference in their entireties, including U.S. provisional application No. 62/670,253, filed May 11, 2018.

Although the foregoing compositions, methods, and uses have been described in some detail to facilitate understanding, it will be apparent that certain changes and modifications may be practiced within the scope of the appended claims. Accordingly, the described embodiments are to be considered as illustrative and not restrictive, and the claimed invention is not to be limited to the details given herein, but may be modified within the scope and equivalents of the appended claims.

What is claimed is:

1. A method of orally administering Compound A to a human in need thereof, wherein Compound A is N-[4-(6-fluoro-3,4-dihydro-1H-isoquinolin-2-yl)-2,6-dimethylphenyl]-3,3-dimethylbutanamide;
   wherein the improvement comprises orally administering an amount of Compound A to the human from between 30 minutes prior to consuming food until 2 hours after consuming food.

2. The method of claim 1, wherein the method increases one or more of the $C_{max}$, $AUC_{inf}$, $T_{max}$, or $t\frac{1}{2}_{\lambda z}$ of Compound A as compared to when the same amount of Compound A is orally administered to the human under fasted conditions.

3. A method of increasing one or more of the $C_{max}$, $AUC_{inf}$, $T_{max}$, or $t\frac{1}{2}_{\lambda z}$ of Compound A in a human receiving an oral administration of Compound A, comprising orally administering an amount of Compound A to the human from between 30 minutes prior to consuming food until 2 hours after consuming food;
   wherein Compound A is N-[4-(6-fluoro-3,4-dihydro-1H-isoquinolin-2-yl)-2,6-dimethylphenyl]-3,3-dimethylbutanamide;
   wherein the method increases the one or more of $C_{max}$, $AUC_{inf}$, $T_{max}$, or $t\frac{1}{2}_{\lambda z}$ as compared to when the same amount of Compound A is orally administered to the human under fasted conditions.

4. A method of reducing a dose of Compound A that is orally administered to a human in need thereof as part of a treatment regimen, comprising orally administering a reduced amount of Compound A to the human from between 30 minutes prior to consuming food until 2 hours after consuming food;
   wherein Compound A is N-[4-(6-fluoro-3,4-dihydro-1H-isoquinolin-2-yl)-2,6-dimethylphenyl]-3,3-dimethylbutanamide; and
   wherein the reduced amount is a dose lower than would be needed to achieve one or more of the same $C_{max}$, $AUC_{inf}$, $T_{max}$, or $t\frac{1}{2}_{\lambda z}$ of Compound A when orally administered to the human under fasted conditions.

5. The method of claim 4, wherein the oral administration of Compound A to the human increases one or more of the $C_{max}$, $AUC_{inf}$, $T_{max}$, or $t\frac{1}{2}_{\lambda z}$ of Compound A as compared to when the same amount of Compound A is orally administered to the human under fasted conditions.

6. A method of treating a seizure disorder in a human in need thereof, comprising orally administering an amount of Compound A to the human from between 30 minutes prior to consuming food until 2 hours after consuming food;
   wherein Compound A is N-[4-(6-fluoro-3,4-dihydro-1H-isoquinolin-2-yl)-2,6-dimethylphenyl]-3,3-dimethylbutanamide; and
   wherein the amount of Compound A is sufficient to treat the seizure disorder in the human.

7. The method of claim 6, wherein the method increases one or more of the $C_{max}$, $AUC_{inf}$, $T_{max}$, or $t\frac{1}{2}_{\lambda z}$ of Compound A as compared to when the same amount of Compound A is orally administered to the human under fasted conditions.

8. The method of any one of claim 2, 3, 5 or 7, wherein the oral administration of Compound A to the human increases the $C_{max}$ of Compound A as compared to when the same amount of Compound A is orally administered to the human under fasted conditions.

9. The method of claim 8, wherein the increase of the $C_{max}$ of Compound A is at least 50%.

10. The method of any one of claim 2, 3, 5 or 7, wherein the oral administration of Compound A to the human increases the $AUC_{inf}$ of Compound A as compared to when the same amount of Compound A is orally administered to the human under fasted conditions.

11. The method of claim 10, wherein the increase of the $AUC_{inf}$ of Compound A is at least 50%.

12. The method of any one of claim 2, 3, 5 or 7, wherein the oral administration of Compound A to the human increases the $T_{max}$ of Compound A as compared to when the same amount of Compound A is orally administered to the human under fasted conditions.

13. The method of claim 12, wherein the increase of the $T_{max}$ of Compound A is at least 50%.

14. The method of any one of claim 2, 3, 5 or 7, wherein the oral administration of Compound A to the human increases the $t\frac{1}{2}_{\lambda z}$ of Compound A as compared to when the same amount of Compound A is orally administered to the human under fasted conditions.

15. The method of claim 14, wherein the increase of the $t\frac{1}{2}_{\lambda z}$ of Compound A is at least 20%.

16. The method of any one of claims 1, 3, 4 or 6, wherein the amount of Compound A is from 2 to 200 mg.

17. The method of claim 16, wherein the amount of Compound A is from 2 to 100 mg.

18. The method of claim 17, wherein the amount of Compound A is from 5 to 50 mg.

19. The method of claim 18, wherein the amount of Compound A is 10, 20, or 25 mg.

20. The method of any one of claim 1, 3, 4 or 6, wherein the amount of Compound A is 5-500 mg per day.

21. The method of claim 20, wherein the amount of Compound A is 20-150 mg per day.

22. The method of any one of claim 1, 3, 4 or 6, wherein the amount of Compound A is 0.05-2.0 mg/kg.

23. The method of claim 22, wherein the amount of Compound A is 0.2-0.5 mg/kg.

24. The method of or claim 6, wherein the seizure disorder is focal onset epilepsy.

25. The method of any one of claim 1, 3, 4 or 6, wherein Compound A is administered to the human once-a-day.

26. The method of claim 25, wherein the Compound A is administered using an immediate release formulation comprising Compound A.

* * * * *